(12) United States Patent
Tanaka et al.

(10) Patent No.: US 7,408,100 B2
(45) Date of Patent: Aug. 5, 2008

(54) METHOD OF CONTROLLING CHARACTER OF MONOCOTYLEDON BY MODIFICATION AND/OR OVEREXPRESSION OF CYTOCHROME P450 MONOOXYGENASE GENE INVOLVED IN BRASSINOSTEROID BIOSYNTHESIS AND MONOCOTYLEDON MODIFIED BY THE GENE

(75) Inventors: Hiroshi Tanaka, Tsukuba (JP); Toshiaki Kayano, Tsukuba (JP); Makoto Matsuoka, Nagoya (JP); Tomoaki Sakamoto, Nishitokyo (JP); Shuichi Iwahori, Ryugasaki (JP)

(73) Assignees: National Institute of Agrobiological Sciences, Ibaraki (JP); Bio-Oriented Technology Research Advancement Institution, Saitama (JP)

( * ) Notice: Subject to any disclaimer, the term of this patent is extended or adjusted under 35 U.S.C. 154(b) by 209 days.

(21) Appl. No.: 10/395,463

(22) Filed: Mar. 20, 2003

(65) Prior Publication Data

US 2004/0060079 A1 Mar. 25, 2004

(30) Foreign Application Priority Data

Sep. 20, 2002 (JP) ............................. 2002-276398

(51) Int. Cl.
*C12N 15/82* (2006.01)
*C12N 5/04* (2006.01)
*A01H 5/00* (2006.01)
*A01H 5/10* (2006.01)

(52) U.S. Cl. .................... 800/320.2; 800/278; 800/286; 800/298; 800/290; 435/419

(58) Field of Classification Search ................ 800/278, 800/290, 298, 320.2, 286; 435/468, 419
See application file for complete search history.

(56) References Cited

U.S. PATENT DOCUMENTS 6,545,200 B1 * 4/2003 Cahoon et al. ............... 800/278

FOREIGN PATENT DOCUMENTS

| JP | 60-116537 | 5/1985 |
| JP | 62-262881 | 10/1987 |
| JP | 06-225830 | 8/1994 |
| WO | WO 97/35986 | 3/1997 |

OTHER PUBLICATIONS

Colliver et al (1997, Plant Mol. Biol. 35:509-522).*
Emery et al (2003, Current Biology 13:1768-1774).*
Brucker et al (Planta (2005) 220:864-874).*
Babiychuk et al (1997 Proc. Natl. Acad. Sci. 94:12722-12727).*
Yamamuro et al (2000, The Plant Cell 12:1591-1605).*
Kapoor et al (2005, The Plant Journal 43:649-661).*
Choe, S., et al., "The *DWF4* Gene of *Arabidopsis* Encodes a Cytochrome P450 That Mediates Multiple 22α-Hydroxylation Steps in Brassinosteroid Biosynthesis," *The Plant Cell*, vol. 10, pp. 231-243, Feb. 1998.
Choe, S., et al., "Overexpression of *DWARF4* in the brassinosteroid biosynthetic pathways results in increased vegetative growth and seed yield in *Arabidopsis*," *The Plant Journal*, vol. 26, No. 6, pp. 573-582, 2001.
Clouse, S. D., et al., "A Brasssinosteroid-Insensitive Mutant in *Arabidopsis thaliana* Exhibits Multiple Defects in Growth and Development," *Plant Physiology*, vol. 111, pp. 671-678, 1996.
Hong, Z., et al., "Loss-of-function of a rice brassinosteroid biosynthetic enzyme, C-6 oxidase, prevents the organized arrangement and polar elongation of cells in the leaves and stem," *The Plant Journal*, vol. 32, pp. 495-508, 2002.
Koes, R., et al., "Targeted gene inactivation in petunia by PCR-based selection of transposon insertion mutants," *Proc. Natl. Acad. Sci. USA*, vol. 92, pp. 8149-8153, Aug. 1995.
Kyozuka, J., et al., "Down-regulation of *RFL*, the *FLO/LFY* homolog of rice, accompanied with panicle branch initiation," *Proc. Natl. Acad. Sci. USA*, vol. 95, pp. 1979-1982, Mar. 1998.
Li, J., et al. "A Putative Leucine-Rich Repeat Receptor Kinase Involved in Brassinosteroid Signal Transduction," *Cell.*, vol. 90, pp. 929-938, Sep. 5, 1997.
Sakamoto, T., et al., "Expression of a Gibberellin 2-Oxidase Gene around the Shoot Apex Is Related to Phase Transition in Rice," *Plant Physiology*, vol. 125, pp. 1508-1516, Mar. 2001.
Thomas, S. G., et al., "Molecular cloning and functional expression of gibberellin 2-oxidases, multifunctional enzymes involved in gibberellin deactivation," *Proc. Natl. Acad. Sci. USA*, vol. 96, pp. 4698-4703, Apr. 1999.
Mori, M., et al., "Isolation and Characterization of a Rice Dwarf Mutant with a Defect in Brassinosteroid Biosynthesis," *Plant Physiology*, vol. 130, pp. 1152-1161, Nov. 2002.
Yamamuro, C., et al., "Loss of Function of a Rice *brassinosteroid insensitive1* Homolog Prevents Internode Elongation and Bending of the Lamina Joint," *The Plant Cell*, vol. 12, pp. 1591-1605, Sep. 2000.
Cloutier, S., et al., GenBank Accession No. BQ620306, TaLr117C08R TaLr1 Triticum aestivum cDNA clone, (2001).
Müssig, C., et al., *Plant Physiology* 129:1241-1251, (2002).
Sato, K., et al., GenBank Accession No. BJ474344, (2002).

* cited by examiner

*Primary Examiner*—Stuart F. Baum
(74) *Attorney, Agent, or Firm*—Susan J. Myers Fitch; Peter J. Dehlinger; King & Spalding LLP

(57) ABSTRACT

A method of producing a modified monocotyledonous plant having a desired character is provided. The method comprises isolating a gene containing a nucleic acid hybridizable to a nucleic acid indicated by SEQ ID NO. 1 under stringent conditions, and inhibiting expression of the isolated gene.

5 Claims, 10 Drawing Sheets

FIG. 1
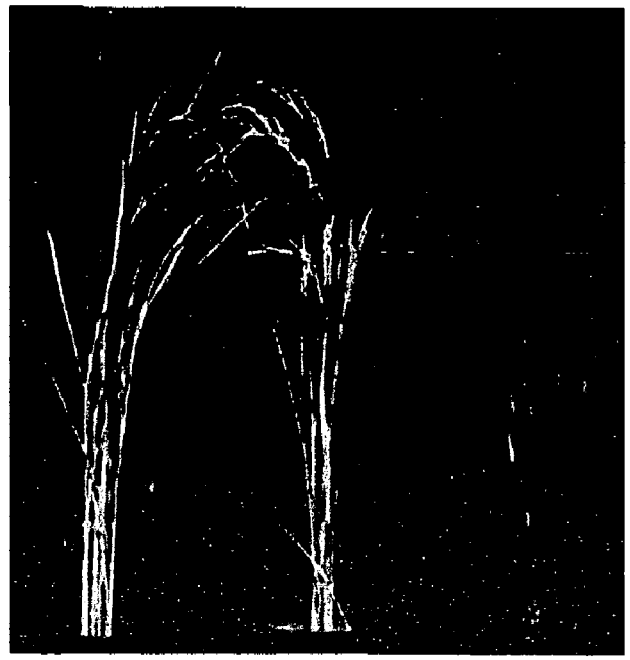
WT        d61
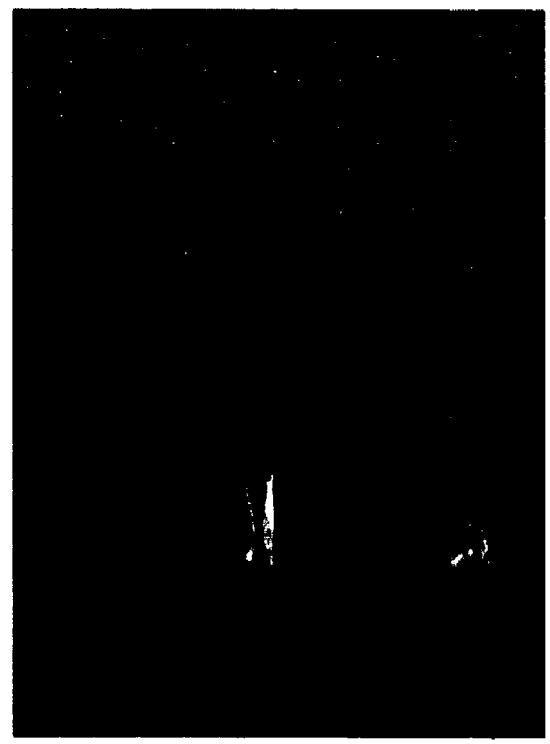
WT        d61
Phenotype of rice d61 mutant Phenotype of novel mutant (Tos2091) similar to that of d61

Locus of a causative gene for a novel mutant
(Tos2091) having a phenotype similar to that of d61

FIG. 4

| Sequence | | |
|---|---|---|
| ATGGCCGCCATGATGGCGTCCATAACCAGCGAGCTGCTCTTCTTTCTCCCCTTCATCCTC | 60 |
| M  A  A  M  M  A  S  I  T  S  E  L  L  F  F  L  P  F  I  L | 20 |
| CTTGCCCTGCTCACGTTCTACACCACCACCGTGGCCAAATGCCACGGCGGGCACTGGTGG | 120 |
| L  A  L  L  T  F  Y  T  T  T  V  A  K  C  H  G  G  H  W  W | 40 |
| CGAGGTGGGACGACGCCGGCGAAGAGGAAGCGGATGAACCTGCCGCCCGGCGCCGCCGGG | 180 |
| R  G  G  T  T  P  A  K  R  K  R  M  N  L  P  P  G  A  A  G | 60 |
| TGGCCGCTCGTCGGCGAGACGTTCGGCTACCTCCGCGCCCACCCCGCCACCTCCGTCGGC | 240 |
| W  P  L  V  G  E  T  F  G  Y  L  R  A  H  P  A  T  S  V  G | 80 |
| CGCTTCATGGAGCAGCACATCGCACGGTACGGGAAGATATACCGGTCGAGCCTGTTCGGG | 300 |
| R  F  M  E  Q  H  I  A  R  Y  G  K  I  Y  R  S  S  L  F  G | 100 |
| GAGCGGACGGTGGTGTCGGCGGACGCGGGGCTCAACCGGTACATCCTGCAGAACGAGGGG | 360 |
| E  R  T  V  V  S  A  D  A  G  L  N  R  Y  I  L  Q  N  E  G | 120 |
| AGGCTGTTCGAGTGCAGCTACCCGCGCAGCATCGGCGGCATCCTGGGCAAGTGGTCCATG | 420 |
| R  L  F  E  C  S  Y  P  R  S  I  G  G  I  L  G  K  W  S  M | 140 |
| CTGGTCCTCGTCGGGGACCCGCACCGCGAGATGCGCGCCATCTCCCTCAACTTCCTCTCC | 480 |
| L  V  L  V  G  D  P  H  R  E  M  R  A  I  S  L  N  F  L  S | 160 |
| TCCGTCCGCCTCCGCGCCGTCCTCCTCCCCGAGGTCGAGCGCCACACCCTCCTCGTCCTC | 540 |
| S  V  R  L  R  A  V  L  L  P  E  V  E  R  H  T  L  L  V  L | 180 |
| CGCGCCTGGCCCCCTTCCTCCACCTTCTCCGCTCAGCACCAAGCCAAGAAGTTCACGTTC | 600 |
| R  A  W  P  P  S  S  T  F  S  A  Q  H  Q  A  K  K  F  T  F | 200 |
| AACCTGATGGCGAAGAACATAATGAGCATGGACCCGGGGGAGGAAGAGACGGAGCGGCTG | 660 |
| N  L  M  A  K  N  I  M  S  M  D  P  G  E  E  E  T  E  R  L | 220 |
| CGGCGGGAGTACATCACCTTCATGAAGGGCGTGGTCTCCGCGCCGCTCAACCTGCCCGGG | 720 |
| R  R  E  Y  I  T  F  M  K  G  V  V  S  A  P  L  N  L  P  G | 240 |
| ACGCCCTACTGGAAGGCTCTCAAGTCGCGTGCTGCCATTCTCGGAGTAATAGAGAGGAAA | 780 |
| T  P  Y  W  K  A  L  K  S  R  A  A  I  L  G  V  I  E  R  K | 260 |
| ATGGAAGAGCGGGTTGAGAAGCTGAGCAAGGAGGATGCAAGCGTAGAGCAAGACGATCTT | 840 |
| M  E  E  R  V  E  K  L  S  K  E  D  A  S  V  E  Q  D  D  L | 280 |
| CTCGGATGGGCTCTGAAACAATCTAACCTTTCAAAAGAGCAAATCCTGGACCTCTTGCTG | 900 |
| L  G  W  A  L  K  Q  S  N  L  S  K  E  Q  I  L  D  L  L  L | 300 |
| AGCTTGCTCTTCGCCGGGCACGAGACGTCGTCCATGGCGCTCGCCCTCGCCATCTTCTTC | 960 |
| S  L  L  F  A  G  E  E  T  S  S  M  A  L  A  L  A  I  F  F | 320 |
| CTTGAAGGCTGCCCCAAGGCTGTCCAAGAACTGAGGGAGGAGCATCTTGGGATTGCAAGG | 1020 |
| L  E  G  C  P  K  A  V  Q  E  L  R  E  E  H  L  G  I  A  R | 340 |
| AGACAAAGGCTAAGAGGGGAGTGCAAATTGAGCTGGGAAGACTACAAAGAGATGGTTTTC | 1080 |
| R  Q  R  L  R  G  E  C  K  L  S  W  E  D  Y  K  E  M  V  F | 360 |
| ACGCAATGTGTCATAAACGAGACGTTGCGGCTAGGAAACGTGGTCAGGTTCCTGCACCGG | 1140 |
| T  Q  C  V  I  N  E  T  L  R  L  G  N  V  V  R  F  L  H  R | 380 |
| AAGGTCATCAAGGACGTGCACTACAAGGGTTATGACATTCCAAGCGGATGGAAGATCCTG | 1200 |
| K  V  I  K  D  V  H  Y  K  G  Y  D  I  P  S  G  W  K  I  L | 400 |
| CCGGTGTTAGCCGCGGTGCATCTGGACTCGTCCCTGTACGAGGACCCCCAGCGCTTCAAT | 1260 |
| P  V  L  A  A  V  H  L  D  S  S  L  Y  E  D  P  Q  R  F  N | 420 |
| CCCTGGAGATGGAAGAGTAGCGGATCATCCGGCGGCTTGGCTCAGAGCAGCAGCTTCATG | 1320 |
| P  W  R  W  K  S  S  G  S  S  G  G  L  A  Q  S  S  S  F  M | 440 |
| CCGTACGGCGGCGGGACGCGGCTGTGCGCCGGGTCGGAGCTCGCGAAGCTGGAGATGGCC | 1380 |
| P  Y  G  G  G  T  R  L  C  A  G  S  E  L  A  K  L  E  M  A | 460 |
| GTGTTCTTGCACCACCTGGTGCTCAACTTCAGGTGGGAGCTCGCCGAGCCGGACCAAGCC | 1440 |
| V  F  L  H  H  L  V  L  N  F  R  W  E  L  A  E  P  D  Q  A | 480 |
| TTCGTCTTCCCCTTCGTCGACTTCCCCAAGGGCCTTCCCATTAGGGTTCATAGAATTGCA | 1500 |
| F  V  F  P  F  V  D  F  P  K  G  L  P  I  R  V  H  R  I  A | 500 |
| CAGGATGATGAGCAGGAGTAA | 1521 |
| Q  D  D  E  Q  E  * | 506 |

Base sequence of OsDWF4 and its putative amino acid sequence

FIG. 5

```
ATGGCCGCCATGATGGCGTCCATAACCAGCGAGCTGCTCTTCTTTCTCCCCTTCATCCTCCTTGCCCTGCTCACGTTCTA    80
ATGTTCGAAACAG-AGCATC-ATA-------------CTCTCTTACCTCTTCTTC-TTCTCC---CATCGCTTTTGTCTCT    62
*** **  *   ** ** ***             ****  * **** * ****   ** ***   ******
CACCACCACCGTGGCCAAATGCCACGGCGGGCACTGGTGGCGAGGTGGGACGACGCCGGCGAAGAGGAAGCGGATG-AAC   159
TCTTCTCTTCTTGATT--------------CTCT--TGAAGAGAAGAAAT-----------AGAAAAACCAGATTCAAT   114
 *  * **                      *  ** **  ***  *              *** ** * *** **
CTGCCGCCCGGCGCCGCCGGGTGGCCGCTCGTCGGCGAGACGTTCGGCTACCTCCGCGCCCACCCCGCCACCTCCGTCGG   239
CTACCTCCGGGTAAATCCGGTTGGCCATTTCTTGGTGAAACCATCGGTTATCTTAAACCGTACACCGCCACAACACTCGG   194
** ** **    **** *****  * ** ** ** **      **  ** ******** * *****
CCGCTTCATGGAGCAGCACATCGCACGGTACGGGAAGATATACCGGTCGAGCCTGTTCGGGGAGCGGACGGTGGTGTCGG   319
TGACTTCATGCAACAACATGTCTCCAAGTATGGTAAGATATATAGATCGAACTTGTTTGGAGAACCAACGATCGTATCAG   274
 ******** *  **  **  *   *** ** ******* *  **** **** *** *** * * *** * ** ** *
CGGACGCGGGGCTCAACCGGTACATCCTGCAGAACGAGGGGAGGCTGTTCGAGTGCAGCTACCCGCGCAGCATCGGCGGC   399
CTGATGCTGGACTTAATAGATTCATATTACAAAACGAAGGAAGGCTCTTTGAATGTAGTTATCCTAGAAGTATAGGTGGG   354
  **  **  **  ** ** ** *  ***    *  ** **  ***** ****   *  ** *   ***  **  ** *
ATCCTGGGCAAGTGGTCCATGCTGGTCCTCGTCGGGGACCCGCACCGCGAGATGCGCGCCATCTCCCTCAACTTCCTCTC   479
ATTCTTGGGAAATGGTCGATGCTTGTTCTTGTTGGTGACATGCATAGAGATATGAGAAGTATCTCGCTTAACTTCTTAAG   434
 * ** *** ** ****   **** ** ** ** **   **    *** *** ** **  **  **** **  *   *
CTCCGTCCGCCTCCGCGCCGTCCTCCTCCCCGAGGTCGAGCGCCACACCCTCCTCGTCCTCCGCGCCTGGCCCCCCTTCCT   559
TCACGCACGTCTTAGAACTATTCTACTTAAAGATGTTGAGAGACATACTTTGTTTGTTCTTGATTCTTGGCAACAAAACT    514
 ** ** **  *   *  ** ** *  *  ** ***  *** **  ** *  ***  ** ** *    ** ** **
CCACCTTCTCCGCTCAGCACCAAGCCAAGAAGTTCACGTTCAACCTGATGGCGAAGAACATAATGAGCATGGACCCGGGG   639
CTATTTTCTCTGCTCAAGACGAGGCCAAAAAGTTTACGTTTAATCTAATGGCGAAGCATATAATGAGTATGGATCCTGGA   594
* *  *****  ****  **   * **** **** ****** ** ** *********  * ****** ****** ** **
GAGGAAGAGACGGAGCGGCTGCGGCGGGAGTACATCACCTTCATGAAGGGCGTGGTCTCCGCGCCGCTCAACCTGCCCGG   719
GAAGAAGAAACAGAGCAATTAAAGAAAGAGTATGTAACTTTCATGAAAGGAGTTGTCTCTGCTCCTCTAAATCTACCAGG   674
** ***** ** ****  *    * **** ****   * * ********  **  ****** ** ** ** ** ** **
GACGCCCTACTGGAAGGCTCTCAAGTCGCGTGCTGCCATTCTCGGAGTAATAGAGAGGAAAATGGAAGAG-------CGG   792
AACTGCTTATCATAAAGCTCTTCAGTCACGAGCAACGATATTGAAGTTCATTGAGAGGAAAATGGAAGAGAGAAAATTGG   754
 **  * **   * * *****  **** **  * *  ** ** ** * **  *** ** ***************   **
GT--------------------------TGA-----------GAAGC-----TGAGCAAGGAGGAT-------GC        818
ATATCAAGGAAGAAGATCAAGAAGAAGAAGAAGTGAAAACAGAGGATGAAGCAGAGATGAGTAAGAGTGATCATGTTAGG   834
 *                         ***       *****   ****  **** ***     **  *
AAGCGTAGAGCAA-GACGATCTTCTCGGATGGGCTCTGAAACAATCTAACCTTTCAAAAGAGCAAATCCTGGACCTCTTG   897
AACAAAGAACAGACGATGATCTTTTGGGATGGGTTTTGAAACATTCGAATTTATCGACGGAGCAAATTCTCGATCTCATT   915
**     *  *   ** ***** *  ******* ** ******  *  ** * **  ******  ** ** *****
CTGAGCTTGCTCTTCGCGGGCACGAGACGTCGTCCATGGCGCTCGCCCTCGCCATCTTCTTCTTGAAGGCTGCCCCAA    977
CTTAGTTTGTTATTTGCCGGACATGAGACTTCTTCTGTAGCCATTGCTCTCGCTATCTTCTTCTTGCAAGCTTGCCCTAA   995
**  * *** *  *  * ***** ********  *  * * *   * * ** ** ******** * **** ****
GGCTGTCCAAGAACTCAGGGAGGAGCATCTTGGGATTGCAAGGAGACAAAGGCTAAGAGGGGAGTGCAAATTGAGCTGGG   1057
AGCCGTTGAAGAGCTTAGGGAAGAGCATCTTGAGATCGCGAGGGCCAAGAAGGAACTAGGAGAGTCAGAATTAAATTGGG   1075
 ** ** ****  ** ***** **********  *** ** ***    *   *    *** *****  **** *****
AAGACTACAAAGAGATGGTTTTCACGCAATGTGTCATAAACGAGACGTTGCGGCTAGGAAACGTGGTCAGGTTCCTGCAC   1137
ATGATTACAAGAAAATGGACTTTACTCAATGTGTTATAAATGAAACTCTTCGATTGGGAAATGTAGTTAGGTTTTTGCAT   1155
* ** ***** *  **** * **** ********  *  ****** *  **  * ***** ** ** *****  ****
CGGAAGGTCATCAAGGACGTGCACTACAAGGGTTATGACATTCCAAGCGGATGGAAGATCCTGCCGGTGTTAGCCGCGGT   1217
CGCAAAGCACTCAAAGATGTTCGGTACAAAGGATACGATATCCCTAGTGGGTGGAAAGTGTTACCGGTGATCTCAGCCGT   1235
**  * *  ** **    ** *  ***** **  * ** ** *   * *****  * ** ** ***** * *    **
GCATCTGGACTCGTCCCTGTACGAGGACCCCCAGCGCTTCAATCCCTGGAGATGGAAG------AGTAGCGGA----TCAT   1288
ACATTTGGATAATTCTCGTTATGACCAACCTAATCTCTTTAATCCTTGGAGATGGCAACAGCAAAACAACGGAGCGTCAT   1315
 *** **** *  ** * ** *  * * **  ** ***  ****** ******* *       *  ** ***    ***
C----------CGGCGGCTT----GGCTCAGAGCAGCAGCTTCATGCCGTACGGCGGCGGGACGCGGCTGTGCGCCGGGTCG   1356
CGTCAGGAAGTGGTAGTTTTTCGACGTGGGGAAACAACTACATGCCGTTTGGAGGAGGGCCAAGGCTATGTGCTGGTTCA   1395
*          * *      *      *  ** * ** ***** * *** ** **   *  **  *** ***  * **
GAGCTCGCGAAGCTGGAGATGCCGTGTTCTTGCACCACCTGGTGCTCAACTTCAGGTGGGAGCTCGCCGAGCCGGACCA   1436
GAGCTAGCCAAGTTAGAAATGGCAGTGTTTATTCATCATCTAGTTCTTAAATTCAATTGGGAATTAGCAGAAGATGATCA   1475
*****  ** ***  * * *** *  **** *  * * * ** *  **  ****    **  * ***  *  * * **
AGCCTTCGTCTTCCCCTTCGTCGACTTCCCCAAGGGCCTTCCCATTAGGGTTCATAGAATTGCACAGGATGATGAGCAGG   1516
ACCATTTGCTTTTCCTTTTGTTGATTTTCCTAACGGTTTTGCCTATTAGGGTTTCTCGTATTCT-----------   1538
 ** *  *  ** ** **  *   ** ** ** ** **  ** ** ****** *    * ***
AGTAA   1521
-GTAA   1542
 ****
```

Comparison of base sequence between OsDWF4
and Arabidopsis thaliana DWF4

FIG. 6

```
MAAMMASITSELLFFLPFILLALLTFYTTTVAKCHGGHWWRGGTTPAKRK        50
MFETEHHTLLPLLL-LP-SLLSLLLFLILLKRR---------------NRKT     35
 *         **  **  ** **  *

RMNLPPGAAGWPLVGETFGYLRAHPATSVGRFMEQHIARYGKIYRSSLFGERTVVSADAG   110
RFNLPPGKSGWPFLGETIGYLKPYTATTLGDFMQQHVSKYGKIYRSNLFGEPTIVSADAG    95
* *****  ***  *** ***     **  *  ** **      ******* ****** ******

LNRYILQNEGRLFECSYPRSIGGILGKWSMLVLVGDPHREMRAISLNFLSSVRLRAVLLP   170
LNRFILQNEGRLFECSYPRSIGGILGKWSMLVLVGDMHRDMRSISLNFLSHARLRTILLK   155
*** ***************************** **  ** *******  *** **

EVERHTLLVLRAWPPSSTFSAQHQAKKFTFNLMAKNIMSMDPGEEETERLRREYITFMKG   230
DVERHTLFVLDSWQQNSIFSAQDEAKKFTFNLMAKHIMSMDPGEEETEQLKKEYVTFMKG   215
 ****** **   *    * ****   *********** ************   **  *****

VVSAPLNLPGTPYWKALKSRAAILGVIERKMEERVEKLSKEDASVEQ-------------   277
VVSAPLNLPGTAYHKALQSRATILKFIERKMEERKLDIKEEDQEEEEVKTEDEAEMSKSD   275
***********  *  ***  *** ********   **     *

--------DDLLGWALKQSNLSKEQILDLLLSLLFAGHETSSMALALAIFFLEGCPKAVQE   330
HVRKQRTDDDLLGWVLKHSNLSTEQILDLILSLLFAGHETSSVAIALAIFFLQACPKAVEE   336
        ****** ** **** ****** ********** *  ** ****** ** *****  *

LREEHLGIARRQRLRGECKLSWEDYKEMVFTQCVINETLRLGNVVRFLHRKVIKDVHYKGY   391
LREEHLEIARAKKELGESELNWDDYKKMDFTQCVINETLRLGNVVRFLHRKALKDVRYKGY   397
******  ***    **  * *  ***  * ************************  *** ****

DIPSGWKILPVLAAVHLDSSLYEDPQRFNPWRWK------SSGSSGGLAQ-SSSFMPYGGG   445
DIPSGWKVLPVISAVHLDNSRYDQPNLFNPWRWQQQNNGASSSGSGSFSTWGNNYMPFGGG   454
******* ***  ***** * *  * ******      **  **         ** ***

TRLCAGSELAKLEMAVFLHHLVLNFRWELAEPDQAFVFPFVDFPKGLPIRVHRIAQDDEQE   506
PRLCAGSELAKLEMAVFIHHLVLKFNWELAEDDQPFAFPFVDFPNGLPIRVSRIL        509
 **************** ***** * ***** ** * ******* ******  **
```

Comparison of putative amino acid sequence
between OsDWF4 and Arabidopsis thaliana DWF4

Analysis of expression of OsDWF4 by RT-PCR

Tos17 insertion site of novel mutant (NE7040) in which Tos17 is inserted in OsDWF4

FIG. 9
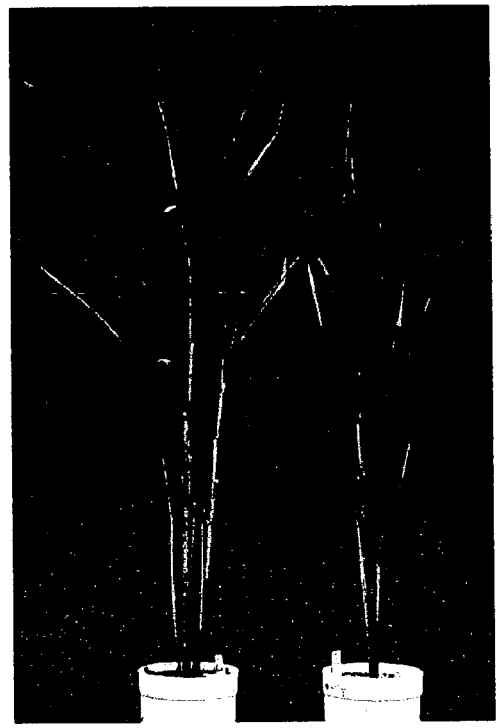
+/+, +/-  -/-
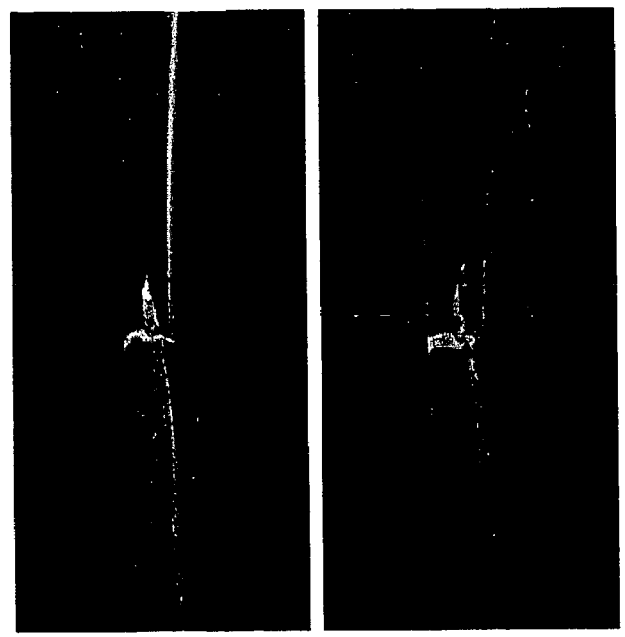
+/+, +/-  -/-
Phenotype of novel mutant (NE7040) in which Tos17 is inserted in OsDWF4

Structure of chimeric gene for overexpression of OsDWF4

SEQUENCE LISTING

```
<160> NUMBER OF SEQ ID NOS: 38

<210> SEQ ID NO 1
<211> LENGTH: 1521
<212> TYPE: DNA
<213> ORGANISM: Oryza sativa
<220> FEATURE:
<221> NAME/KEY: CDS
<222> LOCATION: (1)..(1518)
<223> OTHER INFORMATION:

<400> SEQUENCE: 1 atg gcc gcc atg atg gcg tcc ata acc agc gag ctg ctc ttc ttt ctc      48
Met Ala Ala Met Met Ala Ser Ile Thr Ser Glu Leu Leu Phe Phe Leu
1               5                   10                  15 ccc ttc atc ctc ctt gcc ctg ctc acg ttc tac acc acc acc gtg gcc      96
Pro Phe Ile Leu Leu Ala Leu Leu Thr Phe Tyr Thr Thr Thr Val Ala
```

-continued

```
                 20                  25                  30
aaa tgc cac ggc ggg cac tgg tgg cga ggt ggg acg acg ccg gcg aag    144
Lys Cys His Gly Gly His Trp Trp Arg Gly Gly Thr Thr Pro Ala Lys
        35                  40                  45 agg aag cgg atg aac ctg ccg ccc ggc gcc gcc ggg tgg ccg ctc gtc    192
Arg Lys Arg Met Asn Leu Pro Pro Gly Ala Ala Gly Trp Pro Leu Val
 50                  55                  60 ggc gag acg ttc ggc tac ctc cgc gcc cac ccc gcc acc tcc gtc ggc    240
Gly Glu Thr Phe Gly Tyr Leu Arg Ala His Pro Ala Thr Ser Val Gly
 65                  70                  75                  80 cgc ttc atg gag cag cac atc gca cgg tac ggg aag ata tac cgg tcg    288
Arg Phe Met Glu Gln His Ile Ala Arg Tyr Gly Lys Ile Tyr Arg Ser
                 85                  90                  95 agc ctg ttc ggg gag cgg acg gtg gtg tcg gcg gac gcg ggc ctc aac    336
Ser Leu Phe Gly Glu Arg Thr Val Val Ser Ala Asp Ala Gly Leu Asn
            100                 105                 110 cgg tac atc ctg cag aac gag ggg agg ctg ttc gag tgc agc tac ccg    384
Arg Tyr Ile Leu Gln Asn Glu Gly Arg Leu Phe Glu Cys Ser Tyr Pro
        115                 120                 125 cgc agc atc ggc ggc atc ctg ggc aag tgg tcc atg ctg gtc ctc gtc    432
Arg Ser Ile Gly Gly Ile Leu Gly Lys Trp Ser Met Leu Val Leu Val
130                 135                 140 ggg gac ccg cac cgc gag atg cgc gcc atc tcc ctc aac ttc ctc tcc    480
Gly Asp Pro His Arg Glu Met Arg Ala Ile Ser Leu Asn Phe Leu Ser
145                 150                 155                 160 tcc gtc cgc ctc cgc gcc gtc ctc ctc ccc gag gtc gag cgc cac acc    528
Ser Val Arg Leu Arg Ala Val Leu Leu Pro Glu Val Glu Arg His Thr
                165                 170                 175 ctc ctc gtc ctc cgc gcc tgg ccc cct tcc tcc acc ttc tcc gct cag    576
Leu Leu Val Leu Arg Ala Trp Pro Pro Ser Ser Thr Phe Ser Ala Gln
            180                 185                 190 cac caa gcc aag aag ttc acg ttc aac ctg atg gcg aag aac ata atg    624
His Gln Ala Lys Lys Phe Thr Phe Asn Leu Met Ala Lys Asn Ile Met
        195                 200                 205 agc atg gac ccg ggg gag gaa gag acg gag cgg ctg cgg cgg gag tac    672
Ser Met Asp Pro Gly Glu Glu Glu Thr Glu Arg Leu Arg Arg Glu Tyr
210                 215                 220 atc acc ttc atg aag ggc gtg gtc tcc gcg ccg ctc aac ctg ccc ggg    720
Ile Thr Phe Met Lys Gly Val Val Ser Ala Pro Leu Asn Leu Pro Gly
225                 230                 235                 240 acg ccc tac tgg aag gct ctc aag tcg cgt gct gcc att ctc gga gta    768
Thr Pro Tyr Trp Lys Ala Leu Lys Ser Arg Ala Ala Ile Leu Gly Val
                245                 250                 255 ata gag agg aaa atg gaa gag cgg gtt gag aag ctg agc aag gag gat    816
Ile Glu Arg Lys Met Glu Glu Arg Val Glu Lys Leu Ser Lys Glu Asp
            260                 265                 270 gca agc gta gag caa gac gat ctt ctc gga tgg gct ctg aaa caa tct    864
Ala Ser Val Glu Gln Asp Asp Leu Leu Gly Trp Ala Leu Lys Gln Ser
        275                 280                 285 aac ctt tca aaa gag caa atc ctg gac ctc ttg ctg agc ttg ctc ttc    912
Asn Leu Ser Lys Glu Gln Ile Leu Asp Leu Leu Leu Ser Leu Leu Phe
290                 295                 300 gcc ggg cac gag acg tcg tcc atg gcg ctc gcc ctc gcc atc ttc ttc    960
Ala Gly His Glu Thr Ser Ser Met Ala Leu Ala Leu Ala Ile Phe Phe
305                 310                 315                 320 ctt gaa ggc tgc ccc aag gct gtc caa gaa ctg agg gag gag cat ctt   1008
Leu Glu Gly Cys Pro Lys Ala Val Gln Glu Leu Arg Glu Glu His Leu
                325                 330                 335 ggg att gca agg aga caa agg cta aga ggg gag tgc aaa ttg agc tgg   1056
```

-continued

```
Gly Ile Ala Arg Arg Gln Arg Leu Arg Gly Glu Cys Lys Leu Ser Trp
                340                 345                 350 gaa gac tac aaa gag atg gtt ttc acg caa tgt gtc ata aac gag acg      1104
Glu Asp Tyr Lys Glu Met Val Phe Thr Gln Cys Val Ile Asn Glu Thr
            355                 360                 365 ttg cgg cta gga aac gtg gtc agg ttc ctg cac cgg aag gtc atc aag      1152
Leu Arg Leu Gly Asn Val Val Arg Phe Leu His Arg Lys Val Ile Lys
    370                 375                 380 gac gtg cac tac aag ggt tat gac att cca agc gga tgg aag atc ctg      1200
Asp Val His Tyr Lys Gly Tyr Asp Ile Pro Ser Gly Trp Lys Ile Leu
385                 390                 395                 400 ccg gtg tta gcc gcg gtg cat ctg gac tcg tcc ctg tac gag gac ccc      1248
Pro Val Leu Ala Ala Val His Leu Asp Ser Ser Leu Tyr Glu Asp Pro
                405                 410                 415 cag cgc ttc aat ccc tgg aga tgg aag agt agc gga tca tcc ggc ggc      1296
Gln Arg Phe Asn Pro Trp Arg Trp Lys Ser Ser Gly Ser Ser Gly Gly
            420                 425                 430 ttg gct cag agc agc agc ttc atg ccg tac ggc ggg acg cgg ctg          1344
Leu Ala Gln Ser Ser Ser Phe Met Pro Tyr Gly Gly Gly Thr Arg Leu
    435                 440                 445 tgc gcc ggg tcg gag ctc gcg aag ctg gag atg gcc gtg ttc ttg cac      1392
Cys Ala Gly Ser Glu Leu Ala Lys Leu Glu Met Ala Val Phe Leu His
450                 455                 460 cac ctg gtg ctc aac ttc agg tgg gag ctc gcc gag ccg gac caa gcc      1440
His Leu Val Leu Asn Phe Arg Trp Glu Leu Ala Glu Pro Asp Gln Ala
                470                 475                 480 ttc gtc ttc ccc ttc gtc gac ttc ccc aag ggc ctt ccc att agg gtt      1488
Phe Val Phe Pro Phe Val Asp Phe Pro Lys Gly Leu Pro Ile Arg Val
            485                 490                 495 cat aga att gca cag gat gat gag cag gag taa                          1521
His Arg Ile Ala Gln Asp Asp Glu Gln Glu
    500                 505

<210> SEQ ID NO 2
<211> LENGTH: 506
<212> TYPE: PRT
<213> ORGANISM: Oryza sativa

<400> SEQUENCE: 2

Met Ala Ala Met Met Ala Ser Ile Thr Ser Glu Leu Leu Phe Phe Leu
1               5                   10                  15

Pro Phe Ile Leu Leu Ala Leu Leu Thr Phe Tyr Thr Thr Thr Val Ala
            20                  25                  30

Lys Cys His Gly Gly His Trp Trp Arg Gly Gly Thr Thr Pro Ala Lys
        35                  40                  45

Arg Lys Arg Met Asn Leu Pro Pro Gly Ala Ala Gly Trp Pro Leu Val
    50                  55                  60

Gly Glu Thr Phe Gly Tyr Leu Arg Ala His Pro Ala Thr Ser Val Gly
65                  70                  75                  80

Arg Phe Met Glu Gln His Ile Ala Arg Tyr Gly Lys Ile Tyr Arg Ser
                85                  90                  95

Ser Leu Phe Gly Glu Arg Thr Val Val Ser Ala Asp Ala Gly Leu Asn
            100                 105                 110

Arg Tyr Ile Leu Gln Asn Glu Gly Arg Leu Phe Glu Cys Ser Tyr Pro
        115                 120                 125

Arg Ser Ile Gly Gly Ile Leu Gly Lys Trp Ser Met Leu Val Leu Val
    130                 135                 140

Gly Asp Pro His Arg Glu Met Arg Ala Ile Ser Leu Asn Phe Leu Ser
```

```
                145                 150                 155                 160
Ser Val Arg Leu Arg Ala Val Leu Leu Pro Glu Val Glu Arg His Thr
                165                 170                 175

Leu Leu Val Leu Arg Ala Trp Pro Pro Ser Ser Thr Phe Ser Ala Gln
            180                 185                 190

His Gln Ala Lys Lys Phe Thr Phe Asn Leu Met Ala Lys Asn Ile Met
        195                 200                 205

Ser Met Asp Pro Gly Glu Glu Glu Thr Glu Arg Leu Arg Arg Glu Tyr
    210                 215                 220

Ile Thr Phe Met Lys Gly Val Val Ser Ala Pro Leu Asn Leu Pro Gly
225                 230                 235                 240

Thr Pro Tyr Trp Lys Ala Leu Lys Ser Arg Ala Ala Ile Leu Gly Val
                245                 250                 255

Ile Glu Arg Lys Met Glu Glu Arg Val Glu Lys Leu Ser Lys Glu Asp
            260                 265                 270

Ala Ser Val Glu Gln Asp Leu Leu Gly Trp Ala Leu Lys Gln Ser
        275                 280                 285

Asn Leu Ser Lys Glu Gln Ile Leu Asp Leu Leu Ser Leu Leu Phe
    290                 295                 300

Ala Gly His Glu Thr Ser Ser Met Ala Leu Ala Leu Ala Ile Phe Phe
305                 310                 315                 320

Leu Glu Gly Cys Pro Lys Ala Val Gln Glu Leu Arg Glu Glu His Leu
                325                 330                 335

Gly Ile Ala Arg Arg Gln Arg Leu Arg Gly Glu Cys Lys Leu Ser Trp
            340                 345                 350

Glu Asp Tyr Lys Glu Met Val Phe Thr Gln Cys Val Ile Asn Glu Thr
        355                 360                 365

Leu Arg Leu Gly Asn Val Val Arg Phe Leu His Arg Lys Val Ile Lys
    370                 375                 380

Asp Val His Tyr Lys Gly Tyr Asp Ile Pro Ser Gly Trp Lys Ile Leu
385                 390                 395                 400

Pro Val Leu Ala Ala Val His Leu Asp Ser Ser Leu Tyr Glu Asp Pro
                405                 410                 415

Gln Arg Phe Asn Pro Trp Arg Trp Lys Ser Gly Ser Ser Gly Gly
            420                 425                 430

Leu Ala Gln Ser Ser Ser Phe Met Pro Tyr Gly Gly Thr Arg Leu
        435                 440                 445

Cys Ala Gly Ser Glu Leu Ala Lys Leu Glu Met Ala Val Phe Leu His
    450                 455                 460

His Leu Val Leu Asn Phe Arg Trp Glu Leu Ala Glu Pro Asp Gln Ala
465                 470                 475                 480

Phe Val Phe Pro Phe Val Asp Phe Pro Lys Gly Leu Pro Ile Arg Val
                485                 490                 495

His Arg Ile Ala Gln Asp Asp Glu Gln Glu
            500                 505

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gaaacgtggt caggttcctg ca                                                  22
```

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tgaagctgct gctctgagcc aa                                              22

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ggtgtatagc tagcttgctt gcag                                            24

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gagagccttc cagtagggcg                                                 20

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
actgtatagt tggcccatgt ccag                                            24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
taatcctact gcgactgacc ttcc                                            24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
tgtggtggta tcagataaag gagc                                            24

<210> SEQ ID NO 10
<211> LENGTH: 24
<212> TYPE: DNA
<213> ORGANISM: Artificial Sequence
<220> FEATURE:

```
<223> OTHER INFORMATION: primer

<400> SEQUENCE: 10
taatcctact gcgactgacc ttcc                                              24

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
accacttcag agattgtgtg gttgc                                             25

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
cagcaacgat gtagatggtc aagc                                              24

<210> SEQ ID NO 13
<211> LENGTH: 25
<212> TYPE: DNA
<213> ORGANISM: Artificial Sequence
<220> FEATURE:
<223> OTHER INFORMATION: Dprimer

<400> SEQUENCE: 13
gacaacaccg gagctataca aatcg                                             25

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
aggaggttgc ttagcagtga aacg                                              24

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ctgtatagtt ggcccatgtc c                                                 21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atggactgga catccgatgg                                                   20
```

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tgaagcatcg gtctcagcta                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtaggttggg agggttgtga                                              20

<210> SEQ ID NO 19
<211> LENGTH: 1683
<212> TYPE: DNA
<213> ORGANISM: Oryza sativa
<220> FEATURE:
<221> NAME/KEY: CDS
<222> LOCATION: (1)..(1683)
<223> OTHER INFORMATION:

<400> SEQUENCE: 19

| atg gca gat ctg cag gag ccc ctc gtt cgt ccg aag agg aag aag gtt | 48 |
| Met Ala Asp Leu Gln Glu Pro Leu Val Arg Pro Lys Arg Lys Lys Val | |
| 1               5                  10                  15      | |

| ttg gtg gac tac ttg gta aag ttc cga tgg att ctg gtg atc ttt gtg | 96 |
| Leu Val Asp Tyr Leu Val Lys Phe Arg Trp Ile Leu Val Ile Phe Val | |
|                 20                  25                  30     | |

| gtg ctc ccc att tcc gct ctg atc tac ttc aat atc tat ttg ggc gat | 144 |
| Val Leu Pro Ile Ser Ala Leu Ile Tyr Phe Asn Ile Tyr Leu Gly Asp | |
|             35                  40                  45         | |

| gtc tgg tct gcc atg aaa tct gag aaa cgt cgc cag aag gaa cat gat | 192 |
| Val Trp Ser Ala Met Lys Ser Glu Lys Arg Arg Gln Lys Glu His Asp | |
|         50                  55                  60             | |

| gac aat gtg caa aaa gtt gtg aag cgg ctc aag cag agg aac cca aag | 240 |
| Asp Asn Val Gln Lys Val Val Lys Arg Leu Lys Gln Arg Asn Pro Lys | |
| 65                  70                  75                  80 | |

| aag gat ggc ctt gtt tgc aca gct agg aag ccc tgg att gct gtt ggc | 288 |
| Lys Asp Gly Leu Val Cys Thr Ala Arg Lys Pro Trp Ile Ala Val Gly | |
|                 85                  90                  95     | |

| atg cgc aat gta gac tac aag cgt gct agg cat ttt gag gtt gac ctt | 336 |
| Met Arg Asn Val Asp Tyr Lys Arg Ala Arg His Phe Glu Val Asp Leu | |
|             100                 105                 110        | |

| tcc gcc ttc agg aac att ctt gag att gac aga gag aga atg gtt gcc | 384 |
| Ser Ala Phe Arg Asn Ile Leu Glu Ile Asp Arg Glu Arg Met Val Ala | |
|         115                 120                 125            | |

| aag gtt gag cct ctt gtc aac atg ggc cag ata acc aga gct aca tgc | 432 |
| Lys Val Glu Pro Leu Val Asn Met Gly Gln Ile Thr Arg Ala Thr Cys | |
| 130                 135                 140                    | |

| cca atg aac ctt gcc ctt gca gtt gtt gct gag ctt gat gac ctt act | 480 |
| Pro Met Asn Leu Ala Leu Ala Val Val Ala Glu Leu Asp Asp Leu Thr | |
| 145                 150                 155                 160 | |

| gtt ggg gga ctg atc aat ggg tat ggt att gaa ggg agc tct cac ctc | 528 |
| Val Gly Gly Leu Ile Asn Gly Tyr Gly Ile Glu Gly Ser Ser His Leu | |
|                 165                 170                 175    | |

-continued

| | | |
|---|---|---|
| tat ggt ctt ttc tct gac act gtt gtc gcc gtg gaa gtt gtt ctt gca<br>Tyr Gly Leu Phe Ser Asp Thr Val Val Ala Val Glu Val Val Leu Ala<br>             180                        185                       190 | 576 |
| gac ggt cga gtt gtt aga gcc act aag gat aat gag tac tct gac ctt<br>Asp Gly Arg Val Val Arg Ala Thr Lys Asp Asn Glu Tyr Ser Asp Leu<br>         195                       200                       205 | 624 |
| ttc tat ggc att ccc tgg tcc cag gga aca ctt ggg ttt ctt gtt tcc<br>Phe Tyr Gly Ile Pro Trp Ser Gln Gly Thr Leu Gly Phe Leu Val Ser<br>210                     215                     220 | 672 |
| gct gag atc aaa ctc att ccc atc aag gaa tac atg agg ctc aca tat<br>Ala Glu Ile Lys Leu Ile Pro Ile Lys Glu Tyr Met Arg Leu Thr Tyr<br>225                   230                    235               240 | 720 |
| act cca gtt aaa ggg tca ctg aag gag ata gca caa ggt tat tgt gat<br>Thr Pro Val Lys Gly Ser Leu Lys Glu Ile Ala Gln Gly Tyr Cys Asp<br>                   245                     250                   255 | 768 |
| tcg ttt gca cca cga gat ggt gat cct gca aag gtc cca gac ttc gtt<br>Ser Phe Ala Pro Arg Asp Gly Asp Pro Ala Lys Val Pro Asp Phe Val<br>             260                     265                     270 | 816 |
| gag gga atg gtg tac aca gaa aat gag ggt gtc atg atg act ggt gtt<br>Glu Gly Met Val Tyr Thr Glu Asn Glu Gly Val Met Met Thr Gly Val<br>         275                       280                       285 | 864 |
| tat gct tcc aaa gaa gag gca aag aag aag ggc aat aag atc aac tgt<br>Tyr Ala Ser Lys Glu Glu Ala Lys Lys Lys Gly Asn Lys Ile Asn Cys<br>290                   295                    300 | 912 |
| gtc ggg tgg tgg ttc aag cct tgg ttt tac caa cat gct cag aca gca<br>Val Gly Trp Trp Phe Lys Pro Trp Phe Tyr Gln His Ala Gln Thr Ala<br>305                   310                    315               320 | 960 |
| ctc aag aag ggt gag ttt gtg gag tac att cca aca aga gag tac tac<br>Leu Lys Lys Gly Glu Phe Val Glu Tyr Ile Pro Thr Arg Glu Tyr Tyr<br>                   325                     330                   335 | 1008 |
| cac cgt cac acc cgg tgt ctg tac tgg gag ggg aag ctg atc ttg cca<br>His Arg His Thr Arg Cys Leu Tyr Trp Glu Gly Lys Leu Ile Leu Pro<br>             340                     345                     350 | 1056 |
| ttc ggc gac caa ttc tgg ttc agg ttc ctc ttg ggc tgg ctg atg cca<br>Phe Gly Asp Gln Phe Trp Phe Arg Phe Leu Leu Gly Trp Leu Met Pro<br>         355                       360                       365 | 1104 |
| cca aag gtg tct ctg ctc aag gcc aca cag ggt gaa tct atc agg aat<br>Pro Lys Val Ser Leu Leu Lys Ala Thr Gln Gly Glu Ser Ile Arg Asn<br>370                     375                     380 | 1152 |
| tac tac cat gac aac cat gtg att caa gac atg ctg gtt ccc ttg tac<br>Tyr Tyr His Asp Asn His Val Ile Gln Asp Met Leu Val Pro Leu Tyr<br>385                   390                    395               400 | 1200 |
| aaa gtt gga gat gct ctt gag ttt gtt cac aag gaa atg gag gtt tat<br>Lys Val Gly Asp Ala Leu Glu Phe Val His Lys Glu Met Glu Val Tyr<br>                   405                     410                   415 | 1248 |
| cca ctg tgg ctg tgc ccg cac cgg ctc tac aag ctc cct gtg aaa acc<br>Pro Leu Trp Leu Cys Pro His Arg Leu Tyr Lys Leu Pro Val Lys Thr<br>             420                     425                     430 | 1296 |
| atg gtg tac cca gag cct ggc ttt gag cac cac cac agg caa ggt gac<br>Met Val Tyr Pro Glu Pro Gly Phe Glu His His His Arg Gln Gly Asp<br>         435                       440                       445 | 1344 |
| act agc tat gcc cag atg ttc acc gat gtt ggt gta tat gct cct<br>Thr Ser Tyr Ala Gln Met Phe Thr Asp Val Gly Val Tyr Tyr Ala Pro<br>450                   455                    460 | 1392 |
| ggt gct gtc ctg agg ggc gag gag ttc aat ggc gct cta gct gtc cac<br>Gly Ala Val Leu Arg Gly Glu Glu Phe Asn Gly Ala Leu Ala Val His<br>465                   470                    475               480 | 1440 |
| agg ctg gag cag tgg ctg att gag aac cac agc tac cag cca cag tac<br>Arg Leu Glu Gln Trp Leu Ile Glu Asn His Ser Tyr Gln Pro Gln Tyr<br>                   485                     490                   495 | 1488 |

```
gct gta tct gag ctc aac gag aag gac ttc tgg agg atg ttt gat gct    1536
Ala Val Ser Glu Leu Asn Glu Lys Asp Phe Trp Arg Met Phe Asp Ala
        500                 505                 510 tct cac tac gag cat tgc cgc caa aag tat ggt gcc gtc ggt acc ttt    1584
Ser His Tyr Glu His Cys Arg Gln Lys Tyr Gly Ala Val Gly Thr Phe
    515                 520                 525 atg agc gtc tac tac aag tcc aag aag gga agg aag act gag aag gag    1632
Met Ser Val Tyr Tyr Lys Ser Lys Lys Gly Arg Lys Thr Glu Lys Glu
530                 535                 540 gtg cag gaa gcc gag gcc gcc atc ctc gag cca gcc tac gct gat gag    1680
Val Gln Glu Ala Glu Ala Ala Ile Leu Glu Pro Ala Tyr Ala Asp Glu
545                 550                 555                 560 gcg                                                                 1683
Ala

<210> SEQ ID NO 20
<211> LENGTH: 561
<212> TYPE: PRT
<213> ORGANISM: Oryza sativa

<400> SEQUENCE: 20

Met Ala Asp Leu Gln Glu Pro Leu Val Arg Pro Lys Arg Lys Lys Val
1               5                   10                  15

Leu Val Asp Tyr Leu Val Lys Phe Arg Trp Ile Leu Val Ile Phe Val
                20                  25                  30

Val Leu Pro Ile Ser Ala Leu Ile Tyr Phe Asn Ile Tyr Leu Gly Asp
            35                  40                  45

Val Trp Ser Ala Met Lys Ser Glu Lys Arg Arg Gln Lys Glu His Asp
        50                  55                  60

Asp Asn Val Gln Lys Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
                100                 105                 110

Ser Ala Phe Arg Asn Ile Leu Glu Ile Asp Arg Glu Arg Met Val Ala
            115                 120                 125

Lys Val Glu Pro Leu Val Asn Met Gly Gln Ile Thr Arg Ala Thr Cys
        130                 135                 140

Pro Met Asn Leu Ala Leu Ala Val Val Ala Glu Leu Asp Asp Leu Thr
145                 150                 155                 160

Val Gly Gly Leu Ile Asn Gly Tyr Gly Ile Glu Gly Ser Ser His Leu
                165                 170                 175

Tyr Gly Leu Phe Ser Asp Thr Val Ala Val Glu Val Val Leu Ala
            180                 185                 190

Asp Gly Arg Val Val Arg Ala Thr Lys Asp Asn Glu Tyr Ser Asp Leu
        195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Arg Leu Thr Tyr
225                 230                 235                 240

Thr Pro Val Lys Gly Ser Leu Lys Glu Ile Ala Gln Gly Tyr Cys Asp
                245                 250                 255

Ser Phe Ala Pro Arg Asp Gly Asp Pro Ala Lys Val Pro Asp Phe Val
            260                 265                 270
```

```
Glu Gly Met Val Tyr Thr Glu Asn Glu Gly Val Met Met Thr Gly Val
        275                 280                 285

Tyr Ala Ser Lys Glu Glu Ala Lys Lys Lys Gly Asn Lys Ile Asn Cys
        290                 295                 300

Val Gly Trp Trp Phe Lys Pro Trp Phe Tyr Gln His Ala Gln Thr Ala
305                 310                 315                 320

Leu Lys Lys Gly Glu Phe Val Glu Tyr Ile Pro Thr Arg Glu Tyr Tyr
                325                 330                 335

His Arg His Thr Arg Cys Leu Tyr Trp Glu Gly Lys Leu Ile Leu Pro
            340                 345                 350

Phe Gly Asp Gln Phe Trp Phe Arg Phe Leu Leu Gly Trp Leu Met Pro
        355                 360                 365

Pro Lys Val Ser Leu Leu Lys Ala Thr Gln Gly Glu Ser Ile Arg Asn
370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His Lys Glu Met Glu Val Tyr
                405                 410                 415

Pro Leu Trp Leu Cys Pro His Arg Leu Tyr Lys Leu Pro Val Lys Thr
            420                 425                 430

Met Val Tyr Pro Glu Pro Gly Phe Glu His His Arg Gln Gly Asp
        435                 440                 445

Thr Ser Tyr Ala Gln Met Phe Thr Asp Val Gly Val Tyr Tyr Ala Pro
    450                 455                 460

Gly Ala Val Leu Arg Gly Glu Glu Phe Asn Gly Ala Leu Ala Val His
465                 470                 475                 480

Arg Leu Glu Gln Trp Leu Ile Glu Asn His Ser Tyr Gln Pro Gln Tyr
                485                 490                 495

Ala Val Ser Glu Leu Asn Glu Lys Asp Phe Trp Arg Met Phe Asp Ala
            500                 505                 510

Ser His Tyr Glu His Cys Arg Gln Lys Tyr Gly Ala Val Gly Thr Phe
        515                 520                 525

Met Ser Val Tyr Tyr Lys Ser Lys Lys Gly Arg Lys Thr Glu Lys Glu
    530                 535                 540

Val Gln Glu Ala Glu Ala Ala Ile Leu Glu Pro Ala Tyr Ala Asp Glu
545                 550                 555                 560

Ala

<210> SEQ ID NO 21
<211> LENGTH: 320
<212> TYPE: DNA
<213> ORGANISM: Oryza sativa
<220> FEATURE:
<221> NAME/KEY: CDS
<222> LOCATION: (1)..(318)
<223> OTHER INFORMATION:

<400> SEQUENCE: 21 cgc tgc ctc gtc ggg cta gcc ctc ttc gcg tgg ggg atg cgg acc aac    48
Arg Cys Leu Val Gly Leu Ala Leu Phe Ala Trp Gly Met Arg Thr Asn
1               5                   10                  15 atc gcg gcg gac aag gcg ctc ctg agg ctg aag gag gcc ggg aaa ggg    96
Ile Ala Ala Asp Lys Ala Leu Leu Arg Leu Lys Glu Ala Gly Lys Gly
            20                  25                  30 tac cag att ccc cgc ggc ggg ctg ttc gac gtg gtc acc tgc ccc aac   144
Tyr Gln Ile Pro Arg Gly Gly Leu Phe Asp Val Val Thr Cys Pro Asn
        35                  40                  45
```

```
tac ttc ggc gag gcc gtg gag tgg ctc ggc tac gcg ctg gtg gcg tgg      192
Tyr Phe Gly Glu Ala Val Glu Trp Leu Gly Tyr Ala Leu Val Ala Trp
    50                  55                  60 acg ccg gcg gcc tgg gcc ttc ttc ctc tac acc tgc tcc aac ctc ggg      240
Thr Pro Ala Ala Trp Ala Phe Phe Leu Tyr Thr Cys Ser Asn Leu Gly
65                  70                  75                  80 ccg agg gcc agg gat cac cgc cgg tgg tac gtc ggc aag ttc ggc gac      288
Pro Arg Ala Arg Asp His Arg Arg Trp Tyr Val Gly Lys Phe Gly Asp
                85                  90                  95 aag tac ccg gcg tcg cgc aag gcg ttc gtc cc                           320
Lys Tyr Pro Ala Ser Arg Lys Ala Phe Val
            100                 105

<210> SEQ ID NO 22
<211> LENGTH: 106
<212> TYPE: PRT
<213> ORGANISM: Oryza sativa

<400> SEQUENCE: 22

Arg Cys Leu Val Gly Leu Ala Leu Phe Ala Trp Gly Met Arg Thr Asn
1               5                   10                  15

Ile Ala Ala Asp Lys Ala Leu Leu Arg Leu Lys Glu Ala Gly Lys Gly
            20                  25                  30

Tyr Gln Ile Pro Arg Gly Gly Leu Phe Asp Val Val Thr Cys Pro Asn
        35                  40                  45

Tyr Phe Gly Glu Ala Val Glu Trp Leu Gly Tyr Ala Leu Val Ala Trp
    50                  55                  60

Thr Pro Ala Ala Trp Ala Phe Phe Leu Tyr Thr Cys Ser Asn Leu Gly
65                  70                  75                  80

Pro Arg Ala Arg Asp His Arg Arg Trp Tyr Val Gly Lys Phe Gly Asp
                85                  90                  95

Lys Tyr Pro Ala Ser Arg Lys Ala Phe Val
            100                 105

<210> SEQ ID NO 23
<211> LENGTH: 1506
<212> TYPE: DNA
<213> ORGANISM: Oryza sativa
<220> FEATURE:
<221> NAME/KEY: CDS
<222> LOCATION: (1)..(1506)
<223> OTHER INFORMATION:

<400> SEQUENCE: 23 atg gcc gcg gcc ccg gtg ctc ctc ctc gcc gcg gcc gcc gtc gtc           48
Met Ala Ala Ala Pro Val Leu Leu Leu Ala Ala Ala Ala Val Val
1               5                   10                  15 gtg gtt gcc atg gtg ctc aga tgg ctc ctc ctc ctc ggg ggc ccc gcc       96
Val Val Ala Met Val Leu Arg Trp Leu Leu Leu Leu Gly Gly Pro Ala
            20                  25                  30 gcc ggg agg ctg ggg aag agg gcg ctg atg ccg ccg ggg agc acg ggc      144
Ala Gly Arg Leu Gly Lys Arg Ala Leu Met Pro Pro Gly Ser Thr Gly
        35                  40                  45 ctg ccg ctg att ggc gag acg ctg cgg ctc atc tcg gcg tac aag acg      192
Leu Pro Leu Ile Gly Glu Thr Leu Arg Leu Ile Ser Ala Tyr Lys Thr
    50                  55                  60 ccc aac ccg gag ccg ttc atc gac gag cgc gtg gcg cgc cac ggc ggc      240
Pro Asn Pro Glu Pro Phe Ile Asp Glu Arg Val Ala Arg His Gly Gly
65                  70                  75                  80 gtg ttc acc acc cac gtc ttc ggc gag cgc acc gtg ttc tcc gcc gac      288
```

```
Val Phe Thr Thr His Val Phe Gly Glu Arg Thr Val Phe Ser Ala Asp
            85                  90                  95 ccg gcc ttc aac cgc ctc ctc ctc gcc gcc gag ggc cgc gcc gtc cac      336
Pro Ala Phe Asn Arg Leu Leu Leu Ala Ala Glu Gly Arg Ala Val His
            100                 105                 110 tcc agc tac ccg tcc tcc atc gcc acg ctc ctc ggc gcg cgc tcc ctg      384
Ser Ser Tyr Pro Ser Ser Ile Ala Thr Leu Leu Gly Ala Arg Ser Leu
            115                 120                 125 ctc ctc acc cgc ggc gcc gcg cac aag cgg ctc cac tcc ctc acc ctc      432
Leu Leu Thr Arg Gly Ala Ala His Lys Arg Leu His Ser Leu Thr Leu
        130                 135                 140 acc cgc ctc ggc cgc ccc gcg tcg ccg ccc ctc ctc gcg cac atc gac      480
Thr Arg Leu Gly Arg Pro Ala Ser Pro Pro Leu Leu Ala His Ile Asp
145                 150                 155                 160 cgc ctc gtg ctc gcc acc atg cgc cag tgg gag ccc gcc gcc acc gtg      528
Arg Leu Val Leu Ala Thr Met Arg Gln Trp Glu Pro Ala Ala Thr Val
            165                 170                 175 cgc ctc atg gac gag gcc aag aaa atc acc ttc aac ctc acc gtc aag      576
Arg Leu Met Asp Glu Ala Lys Lys Ile Thr Phe Asn Leu Thr Val Lys
            180                 185                 190 cag ctc gtc agc atc gag ccg gga ccg tgg acc gag agc ctc cgc cgc      624
Gln Leu Val Ser Ile Glu Pro Gly Pro Trp Thr Glu Ser Leu Arg Arg
            195                 200                 205 gag tac gtc aag ctc atc gac ggc ttc ttc tcc atc ccc ttt cct ctc      672
Glu Tyr Val Lys Leu Ile Asp Gly Phe Phe Ser Ile Pro Phe Pro Leu
210                 215                 220 gcc aac ctc ctc cct ttt acc acc tac ggc cag gcc ctc aag gcg agg      720
Ala Asn Leu Leu Pro Phe Thr Thr Tyr Gly Gln Ala Leu Lys Ala Arg
225                 230                 235                 240 aag aag gtg gcc ggt gca ctg cgg gag gtg ata aag aag agg atg gag      768
Lys Lys Val Ala Gly Ala Leu Arg Glu Val Ile Lys Lys Arg Met Glu
            245                 250                 255 gag aaa gcg gag aat ggt ggc tcc att ggg gat gat gag ggg aag aag      816
Glu Lys Ala Glu Asn Gly Gly Ser Ile Gly Asp Asp Glu Gly Lys Lys
            260                 265                 270 gag aag aag gac atg gtt gag gag ctt ctt gag gcg gag ggt ggc agc      864
Glu Lys Lys Asp Met Val Glu Glu Leu Leu Glu Ala Glu Gly Gly Ser
            275                 280                 285 ttc tcg gag gaa gag atg gtg gat ttc tgc ctt tct ctg ctg gtg gct      912
Phe Ser Glu Glu Glu Met Val Asp Phe Cys Leu Ser Leu Leu Val Ala
            290                 295                 300 ggg tat gag act acg tcc atg ctc atg acg ctc gcg gtc aag ttc ctc      960
Gly Tyr Glu Thr Thr Ser Met Leu Met Thr Leu Ala Val Lys Phe Leu
305                 310                 315                 320 act gag acg cct gct gcg cta gct gag ctc aag gaa gag cat gcc aat     1008
Thr Glu Thr Pro Ala Ala Leu Ala Glu Leu Lys Glu Glu His Ala Asn
            325                 330                 335 atc agg gat atg aaa ggg aaa aaa caa cca cta gag tgg agc gat tac     1056
Ile Arg Asp Met Lys Gly Lys Lys Gln Pro Leu Glu Trp Ser Asp Tyr
            340                 345                 350 aag tcc atg cca ttt act caa tgt gtg ata aat gag aca ctc cgt gtg     1104
Lys Ser Met Pro Phe Thr Gln Cys Val Ile Asn Glu Thr Leu Arg Val
            355                 360                 365 ggt aac att att agt gga gta ttc agg cga gca aac act gat att cat     1152
Gly Asn Ile Ile Ser Gly Val Phe Arg Arg Ala Asn Thr Asp Ile His
            370                 375                 380 tat aaa gat tac aca att cca aag gga tgc aag att ttt gct tca ttc     1200
Tyr Lys Asp Tyr Thr Ile Pro Lys Gly Cys Lys Ile Phe Ala Ser Phe
385                 390                 395                 400
```

-continued

```
cga gct gtg cac ctt aat aat gaa cac tac gag aat gct cgg aca ttt    1248
Arg Ala Val His Leu Asn Asn Glu His Tyr Glu Asn Ala Arg Thr Phe
            405                 410                 415 aac cct tgg aga tgg cag atc aac aat aaa ctt cag aat gcg gta ggg    1296
Asn Pro Trp Arg Trp Gln Ile Asn Asn Lys Leu Gln Asn Ala Val Gly
        420                 425                 430 gcc aat ata ttt act cca ttt ggc ggt gga ccc cgg ttg tgt cct ggc    1344
Ala Asn Ile Phe Thr Pro Phe Gly Gly Gly Pro Arg Leu Cys Pro Gly
    435                 440                 445 tat gag ctt gcc cgg gtt gtc gtt tct atc ttc ctc cat cat ctt gta    1392
Tyr Glu Leu Ala Arg Val Val Val Ser Ile Phe Leu His His Leu Val
450                 455                 460 acg cgc ttt agc tgg gaa gaa acc gaa gaa gat aga ctt gtc ttc ttc    1440
Thr Arg Phe Ser Trp Glu Glu Thr Glu Glu Asp Arg Leu Val Phe Phe
465                 470                 475                 480 ccc acc aca cga act ctc aaa gga tac cct atc aat ctt cgg ctg ctt    1488
Pro Thr Thr Arg Thr Leu Lys Gly Tyr Pro Ile Asn Leu Arg Leu Leu
                485                 490                 495 tca gaa tca att tgc tga                                            1506
Ser Glu Ser Ile Cys
            500

<210> SEQ ID NO 24
<211> LENGTH: 501
<212> TYPE: PRT
<213> ORGANISM: Oryza sativa

<400> SEQUENCE: 24

Met Ala Ala Ala Pro Val Leu Leu Ala Ala Ala Ala Val Val
1               5                   10                  15

Val Val Ala Met Val Leu Arg Trp Leu Leu Leu Gly Gly Pro Ala
            20                  25                  30

Ala Gly Arg Leu Gly Lys Arg Ala Leu Met Pro Pro Gly Ser Thr Gly
        35                  40                  45

Leu Pro Leu Ile Gly Glu Thr Leu Arg Leu Ile Ser Ala Tyr Lys Thr
    50                  55                  60

Pro Asn Pro Glu Pro Phe Ile Asp Glu Arg Val Ala Arg His Gly Gly
65                  70                  75                  80

Val Phe Thr Thr His Val Phe Gly Glu Arg Thr Val Phe Ser Ala Asp
                85                  90                  95

Pro Ala Phe Asn Arg Leu Leu Leu Ala Ala Glu Gly Arg Ala Val His
            100                 105                 110

Ser Ser Tyr Pro Ser Ser Ile Ala Thr Leu Leu Gly Ala Arg Ser Leu
        115                 120                 125

Leu Leu Thr Arg Gly Ala Ala His Lys Arg Leu His Ser Leu Thr Leu
    130                 135                 140

Thr Arg Leu Gly Arg Pro Ala Ser Pro Pro Leu Leu Ala His Ile Asp
145                 150                 155                 160

Arg Leu Val Leu Ala Thr Met Arg Gln Trp Glu Pro Ala Ala Thr Val
                165                 170                 175

Arg Leu Met Asp Glu Ala Lys Lys Ile Thr Phe Asn Leu Thr Val Lys
            180                 185                 190

Gln Leu Val Ser Ile Glu Pro Gly Pro Trp Thr Glu Ser Leu Arg Arg
        195                 200                 205

Glu Tyr Val Lys Leu Ile Asp Gly Phe Phe Ser Ile Pro Phe Pro Leu
    210                 215                 220

Ala Asn Leu Leu Pro Phe Thr Thr Tyr Gly Gln Ala Leu Lys Ala Arg
```

-continued

```
                225                 230                 235                 240
Lys Lys Val Ala Gly Ala Leu Arg Glu Val Ile Lys Lys Arg Met Glu
                    245                 250                 255
Glu Lys Ala Glu Asn Gly Gly Ser Ile Gly Asp Asp Glu Gly Lys Lys
                260                 265                 270
Glu Lys Lys Asp Met Val Glu Leu Leu Glu Ala Glu Gly Gly Ser
            275                 280                 285
Phe Ser Glu Glu Glu Met Val Asp Phe Cys Leu Ser Leu Leu Val Ala
        290                 295                 300
Gly Tyr Glu Thr Thr Ser Met Leu Met Thr Leu Ala Val Lys Phe Leu
305                 310                 315                 320
Thr Glu Thr Pro Ala Ala Leu Ala Glu Leu Lys Glu Glu His Ala Asn
                    325                 330                 335
Ile Arg Asp Met Lys Gly Lys Lys Gln Pro Leu Glu Trp Ser Asp Tyr
                340                 345                 350
Lys Ser Met Pro Phe Thr Gln Cys Val Ile Asn Glu Thr Leu Arg Val
            355                 360                 365
Gly Asn Ile Ile Ser Gly Val Phe Arg Arg Ala Asn Thr Asp Ile His
        370                 375                 380
Tyr Lys Asp Tyr Thr Ile Pro Lys Gly Cys Lys Ile Phe Ala Ser Phe
385                 390                 395                 400
Arg Ala Val His Leu Asn Asn Glu His Tyr Glu Asn Ala Arg Thr Phe
                    405                 410                 415
Asn Pro Trp Arg Trp Gln Ile Asn Asn Lys Leu Gln Asn Ala Val Gly
                420                 425                 430
Ala Asn Ile Phe Thr Pro Phe Gly Gly Pro Arg Leu Cys Pro Gly
            435                 440                 445
Tyr Glu Leu Ala Arg Val Val Ser Ile Phe Leu His His Leu Val
        450                 455                 460
Thr Arg Phe Ser Trp Glu Thr Glu Glu Asp Arg Leu Val Phe Phe
465                 470                 475                 480
Pro Thr Thr Arg Thr Leu Lys Gly Tyr Pro Ile Asn Leu Arg Leu Leu
                    485                 490                 495
Ser Glu Ser Ile Cys
            500

<210> SEQ ID NO 25
<211> LENGTH: 573
<212> TYPE: DNA
<213> ORGANISM: Oryza sativa
<220> FEATURE:
<221> NAME/KEY: CDS
<222> LOCATION: (1)..(573)
<223> OTHER INFORMATION:

<400> SEQUENCE: 25 ctc atg acg ctc gcg gtc aag ttc ctc act gag acg cct gct gcg cta      48
Leu Met Thr Leu Ala Val Lys Phe Leu Thr Glu Thr Pro Ala Ala Leu
1               5                   10                  15 gct gag ctc aag gaa gag cat gcc aat atc agg gat atg aaa ggg aaa      96
Ala Glu Leu Lys Glu Glu His Ala Asn Ile Arg Asp Met Lys Gly Lys
            20                  25                  30 aaa caa cca cta gag tgg agc gat tac aag tcc atg cca ttt act caa     144
Lys Gln Pro Leu Glu Trp Ser Asp Tyr Lys Ser Met Pro Phe Thr Gln
        35                  40                  45 tgt gtg ata aat gag aca ctc cgt gtg ggt aac att att agt gga gta     192
Cys Val Ile Asn Glu Thr Leu Arg Val Gly Asn Ile Ile Ser Gly Val
```

-continued

```
                50                  55                  60
ttc agg cga gca aac act gat att cat tat aaa gat tac aca att cca      240
Phe Arg Arg Ala Asn Thr Asp Ile His Tyr Lys Asp Tyr Thr Ile Pro
 65                  70                  75                  80 aag gga tgc aag att ttt gct tca ttc cga gct gtg cac ctt aat aat      288
Lys Gly Cys Lys Ile Phe Ala Ser Phe Arg Ala Val His Leu Asn Asn
                 85                  90                  95 gaa cac tac gag aat gct cgg aca ttt aac cct tgg aga tgg cag atc      336
Glu His Tyr Glu Asn Ala Arg Thr Phe Asn Pro Trp Arg Trp Gln Ile
            100                 105                 110 aac aat aaa ctt cag aat gcg gta ggg gcc aat ata ttt act cca ttt      384
Asn Asn Lys Leu Gln Asn Ala Val Gly Ala Asn Ile Phe Thr Pro Phe
        115                 120                 125 ggc ggt gga ccc cgg ttg tgt cct ggc tat gag ctt gcc cgg gtt gtc      432
Gly Gly Gly Pro Arg Leu Cys Pro Gly Tyr Glu Leu Ala Arg Val Val
    130                 135                 140 gtt tct atc ttc ctc cat cat ctt gta acg cgc ttt agc tgg gaa gaa      480
Val Ser Ile Phe Leu His His Leu Val Thr Arg Phe Ser Trp Glu Glu
145                 150                 155                 160 acc gaa gaa gat aga ctt gtc ttc ttc ccc acc aca cga act ctc aaa      528
Thr Glu Glu Asp Arg Leu Val Phe Phe Pro Thr Thr Arg Thr Leu Lys
                165                 170                 175 gga tac cct atc aat ctt cgg ctg ctt tca gaa tca att tgc tga           573
Gly Tyr Pro Ile Asn Leu Arg Leu Leu Ser Glu Ser Ile Cys
                180                 185                 190

<210> SEQ ID NO 26
<211> LENGTH: 190
<212> TYPE: PRT
<213> ORGANISM: Oryza sativa

<400> SEQUENCE: 26

Leu Met Thr Leu Ala Val Lys Phe Leu Thr Glu Thr Pro Ala Ala Leu
  1               5                  10                  15

Ala Glu Leu Lys Glu Glu His Ala Asn Ile Arg Asp Met Lys Gly Lys
                 20                  25                  30

Lys Gln Pro Leu Glu Trp Ser Asp Tyr Lys Ser Met Pro Phe Thr Gln
             35                  40                  45

Cys Val Ile Asn Glu Thr Leu Arg Val Gly Asn Ile Ile Ser Gly Val
         50                  55                  60

Phe Arg Arg Ala Asn Thr Asp Ile His Tyr Lys Asp Tyr Thr Ile Pro
 65                  70                  75                  80

Lys Gly Cys Lys Ile Phe Ala Ser Phe Arg Ala Val His Leu Asn Asn
                 85                  90                  95

Glu His Tyr Glu Asn Ala Arg Thr Phe Asn Pro Trp Arg Trp Gln Ile
            100                 105                 110

Asn Asn Lys Leu Gln Asn Ala Val Gly Ala Asn Ile Phe Thr Pro Phe
        115                 120                 125

Gly Gly Gly Pro Arg Leu Cys Pro Gly Tyr Glu Leu Ala Arg Val Val
    130                 135                 140

Val Ser Ile Phe Leu His His Leu Val Thr Arg Phe Ser Trp Glu Glu
145                 150                 155                 160

Thr Glu Glu Asp Arg Leu Val Phe Phe Pro Thr Thr Arg Thr Leu Lys
                165                 170                 175

Gly Tyr Pro Ile Asn Leu Arg Leu Leu Ser Glu Ser Ile Cys
            180                 185                 190
```

```
<210> SEQ ID NO 27
<211> LENGTH: 315
<212> TYPE: DNA
<213> ORGANISM: Oryza sativa
<220> FEATURE:
<221> NAME/KEY: CDS
<222> LOCATION: (1)..(315)
<223> OTHER INFORMATION:

<400> SEQUENCE: 27 gct tca ttc cga gct gtg cac ctt aat aat gaa cac tac gag aat gct        48
Ala Ser Phe Arg Ala Val His Leu Asn Asn Glu His Tyr Glu Asn Ala
1               5                   10                  15 cgg aca ttt aac cct tgg aga tgg cag atc aac aat aaa ctt cag aat        96
Arg Thr Phe Asn Pro Trp Arg Trp Gln Ile Asn Asn Lys Leu Gln Asn
            20                  25                  30 gcg gta ggg gcc aat ata ttt act cca ttt ggt ggt gga cct cgg ttg       144
Ala Val Gly Ala Asn Ile Phe Thr Pro Phe Gly Gly Gly Pro Arg Leu
        35                  40                  45 tgt cct ggc tat gag ctt gcc cgg gtt gtc gtt tct atc ttc ctc cat       192
Cys Pro Gly Tyr Glu Leu Ala Arg Val Val Val Ser Ile Phe Leu His
    50                  55                  60 cat ctt gta acg cgc ttt agc tgg gaa gaa acc gaa gaa gat aga ctt       240
His Leu Val Thr Arg Phe Ser Trp Glu Glu Thr Glu Glu Asp Arg Leu
65                  70                  75                  80 gtc ttc ttc ccc acc aca cga act ctc aaa gga tac cct atc aat ctt       288
Val Phe Phe Pro Thr Thr Arg Thr Leu Lys Gly Tyr Pro Ile Asn Leu
                85                  90                  95 cgg ctg ctt tca gaa tca att tgc tga                                   315
Arg Leu Leu Ser Glu Ser Ile Cys
            100

<210> SEQ ID NO 28
<211> LENGTH: 104
<212> TYPE: PRT
<213> ORGANISM: Oryza sativa

<400> SEQUENCE: 28

Ala Ser Phe Arg Ala Val His Leu Asn Asn Glu His Tyr Glu Asn Ala
1               5                   10                  15

Arg Thr Phe Asn Pro Trp Arg Trp Gln Ile Asn Asn Lys Leu Gln Asn
            20                  25                  30

Ala Val Gly Ala Asn Ile Phe Thr Pro Phe Gly Gly Gly Pro Arg Leu
        35                  40                  45

Cys Pro Gly Tyr Glu Leu Ala Arg Val Val Val Ser Ile Phe Leu His
    50                  55                  60

His Leu Val Thr Arg Phe Ser Trp Glu Glu Thr Glu Glu Asp Arg Leu
65                  70                  75                  80

Val Phe Phe Pro Thr Thr Arg Thr Leu Lys Gly Tyr Pro Ile Asn Leu
                85                  90                  95

Arg Leu Leu Ser Glu Ser Ile Cys
            100

<210> SEQ ID NO 29
<211> LENGTH: 1410
<212> TYPE: DNA
<213> ORGANISM: Oryza sativa
<220> FEATURE:
<221> NAME/KEY: CDS
<222> LOCATION: (1)..(1410)
<223> OTHER INFORMATION:

<400> SEQUENCE: 29
```

-continued

| | |
|---|---|
| atg gtg ttg gtg gcg att ggg gtg gtt gtg gcg gcg gcg gtg gtg gtg<br>Met Val Leu Val Ala Ile Gly Val Val Val Ala Ala Ala Val Val Val<br>1               5                   10                  15 | 48 |
| agc agc ctg ctg ctg cgg tgg aac gag gtg cgg tac agc cgg aag cgc<br>Ser Ser Leu Leu Leu Arg Trp Asn Glu Val Arg Tyr Ser Arg Lys Arg<br>            20                  25                  30 | 96 |
| ggc ctg ccg ccg ggg aca atg ggg tgg ccg ctc ttc ggc gag acc acc<br>Gly Leu Pro Pro Gly Thr Met Gly Trp Pro Leu Phe Gly Glu Thr Thr<br>        35                  40                  45 | 144 |
| gag ttc ctc aag cag gga ccc agt ttc atg aag gcc cgg agg ctc agg<br>Glu Phe Leu Lys Gln Gly Pro Ser Phe Met Lys Ala Arg Arg Leu Arg<br>50                  55                  60 | 192 |
| tac ggg agc gtg ttc agg acg cac atc ctg ggg tgc ccg acg gtg gtg<br>Tyr Gly Ser Val Phe Arg Thr His Ile Leu Gly Cys Pro Thr Val Val<br>65                  70                  75                  80 | 240 |
| tgt atg gag gcg gag ctg aac cgg cgg gcg ctg gcc agc gaa ggg cgc<br>Cys Met Glu Ala Glu Leu Asn Arg Arg Ala Leu Ala Ser Glu Gly Arg<br>                85                  90                  95 | 288 |
| ggg ttc gtc ccg ggc tac ccg cag tcg atg ctg gac atc ctg ggg cgg<br>Gly Phe Val Pro Gly Tyr Pro Gln Ser Met Leu Asp Ile Leu Gly Arg<br>            100                 105                 110 | 336 |
| aac aac atc gcc gcc gtg cag ggc ccc ctc cac cgc gcc atg cgc ggc<br>Asn Asn Ile Ala Ala Val Gln Gly Pro Leu His Arg Ala Met Arg Gly<br>        115                 120                 125 | 384 |
| gcc atg ctc tcc ctc gtc cgc ccc gcc atg atc cgc tcc tcc ctc ctc<br>Ala Met Leu Ser Leu Val Arg Pro Ala Met Ile Arg Ser Ser Leu Leu<br>130                 135                 140 | 432 |
| ccc aag atc gac gcc ttc atg cgc tcc cac ctc gcc gcc tgg tcc tcc<br>Pro Lys Ile Asp Ala Phe Met Arg Ser His Leu Ala Ala Trp Ser Ser<br>145                 150                 155                 160 | 480 |
| tcc tcc tcc tcc gcc gtc gtc gac atc cag gcc aag acc aag gag atg<br>Ser Ser Ser Ser Ala Val Val Asp Ile Gln Ala Lys Thr Lys Glu Met<br>                165                 170                 175 | 528 |
| gcc ttg cta tct gca ctc agg cag att gcc ggc gtc tcc gct ggc cca<br>Ala Leu Leu Ser Ala Leu Arg Gln Ile Ala Gly Val Ser Ala Gly Pro<br>            180                 185                 190 | 576 |
| ctc tct gac gct ctc aag gca gag ctc tac acc ctt gtg ctt ggc acc<br>Leu Ser Asp Ala Leu Lys Ala Glu Leu Tyr Thr Leu Val Leu Gly Thr<br>        195                 200                 205 | 624 |
| atc tcc ctg ccc atc aac ctt cct gga acc aac tac tac caa ggc ttc<br>Ile Ser Leu Pro Ile Asn Leu Pro Gly Thr Asn Tyr Tyr Gln Gly Phe<br>210                 215                 220 | 672 |
| aag gca agg aag aag ctt gtt gca atg cta gag cag atg atc gcg gaa<br>Lys Ala Arg Lys Lys Leu Val Ala Met Leu Glu Gln Met Ile Ala Glu<br>225                 230                 235                 240 | 720 |
| cgg cga tcc tcc ggt cag gta cac gac gac atg ctg gat gcg ctc ttg<br>Arg Arg Ser Ser Gly Gln Val His Asp Asp Met Leu Asp Ala Leu Leu<br>                245                 250                 255 | 768 |
| acc ggt gtc gag ggc acc agg gag aag ctc aca gat gag cag atc att<br>Thr Gly Val Glu Gly Thr Arg Glu Lys Leu Thr Asp Glu Gln Ile Ile<br>            260                 265                 270 | 816 |
| gac ctg atc atc acc ctt ata tac tct gga tat gaa acc atg tcg acg<br>Asp Leu Ile Ile Thr Leu Ile Tyr Ser Gly Tyr Glu Thr Met Ser Thr<br>        275                 280                 285 | 864 |
| acc tcg atg atg gct gtc aag tac ctg tca gac cat ccc aaa gct ctt<br>Thr Ser Met Met Ala Val Lys Tyr Leu Ser Asp His Pro Lys Ala Leu<br>290                 295                 300 | 912 |
| gag caa ctc agg aaa gaa cat ttt gat atc agg aaa ggt aaa gcg ccc<br>Glu Gln Leu Arg Lys Glu His Phe Asp Ile Arg Lys Gly Lys Ala Pro | 960 |

-continued

```
                305                 310                 315                 320
gaa gat gcc atc gac tgg aat gat ttc aag tcc atg acc ttc act cga        1008
Glu Asp Ala Ile Asp Trp Asn Asp Phe Lys Ser Met Thr Phe Thr Arg
                    325                 330                 335 gct gtt atc ttc gag aca tta aga tta gct aca gtt gtg aat ggg ctg        1056
Ala Val Ile Phe Glu Thr Leu Arg Leu Ala Thr Val Val Asn Gly Leu
                340                 345                 350 ctg agg aaa act acc caa gat gtt gaa atg aat ggg tat gtt atc cca        1104
Leu Arg Lys Thr Thr Gln Asp Val Glu Met Asn Gly Tyr Val Ile Pro
            355                 360                 365 aaa ggt tgg aga ata tat gtt tac aca agg gaa ata aat tat gat cca        1152
Lys Gly Trp Arg Ile Tyr Val Tyr Thr Arg Glu Ile Asn Tyr Asp Pro
        370                 375                 380 ttc ctg tac cct gat ccc atg aca ttc aat cca tgg agg tgg ctg gag        1200
Phe Leu Tyr Pro Asp Pro Met Thr Phe Asn Pro Trp Arg Trp Leu Glu
385                 390                 395                 400 aag aac atg gaa tca cat cca cac ttc atg ctg ttt gga gga ggt agt        1248
Lys Asn Met Glu Ser His Pro His Phe Met Leu Phe Gly Gly Gly Ser
                405                 410                 415 cga atg tgc ccg ggg aag gaa gta ggc acc gta gaa att gca aca ttc        1296
Arg Met Cys Pro Gly Lys Glu Val Gly Thr Val Glu Ile Ala Thr Phe
            420                 425                 430 ctt cac tat ttc gtg act caa tac aga tgg gag gaa gaa ggt aac aac        1344
Leu His Tyr Phe Val Thr Gln Tyr Arg Trp Glu Glu Glu Gly Asn Asn
        435                 440                 445 aca ata ttg aag ttc ccc cga gtt gaa gct ccc aac ggg tta cat atc        1392
Thr Ile Leu Lys Phe Pro Arg Val Glu Ala Pro Asn Gly Leu His Ile
    450                 455                 460 cgc gtt caa gat tac tga                                                 1410
Arg Val Gln Asp Tyr
465

<210> SEQ ID NO 30
<211> LENGTH: 469
<212> TYPE: PRT
<213> ORGANISM: Oryza sativa

<400> SEQUENCE: 30

Met Val Leu Val Ala Ile Gly Val Val Ala Ala Val Val
1               5                   10              15

Ser Ser Leu Leu Leu Arg Trp Asn Glu Val Arg Tyr Ser Arg Lys Arg
                20                  25                  30

Gly Leu Pro Pro Gly Thr Met Gly Trp Pro Leu Phe Gly Glu Thr Thr
            35                  40                  45

Glu Phe Leu Lys Gln Gly Pro Ser Phe Met Lys Ala Arg Arg Leu Arg
        50                  55                  60

Tyr Gly Ser Val Phe Arg Thr His Ile Leu Gly Cys Pro Thr Val Val
65                  70                  75                  80

Cys Met Glu Ala Glu Leu Asn Arg Arg Ala Leu Ala Ser Glu Gly Arg
                85                  90                  95

Gly Phe Val Pro Gly Tyr Pro Gln Ser Met Leu Asp Ile Leu Gly Arg
            100                 105                 110

Asn Asn Ile Ala Ala Val Gln Gly Pro Leu His Arg Ala Met Arg Gly
        115                 120                 125

Ala Met Leu Ser Leu Val Arg Pro Ala Met Ile Arg Ser Ser Leu Leu
    130                 135                 140

Pro Lys Ile Asp Ala Phe Met Arg Ser His Leu Ala Ala Trp Ser Ser
145                 150                 155                 160
```

```
Ser Ser Ser Ser Ala Val Val Asp Ile Gln Ala Lys Thr Lys Glu Met
            165                 170                 175

Ala Leu Leu Ser Ala Leu Arg Gln Ile Ala Gly Val Ser Ala Gly Pro
            180                 185                 190

Leu Ser Asp Ala Leu Lys Ala Glu Leu Tyr Thr Leu Val Leu Gly Thr
            195                 200                 205

Ile Ser Leu Pro Ile Asn Leu Pro Gly Thr Asn Tyr Tyr Gln Gly Phe
            210                 215                 220

Lys Ala Arg Lys Lys Leu Val Ala Met Leu Glu Gln Met Ile Ala Glu
225                 230                 235                 240

Arg Arg Ser Ser Gly Gln Val His Asp Asp Met Leu Asp Ala Leu Leu
            245                 250                 255

Thr Gly Val Glu Gly Thr Arg Glu Lys Leu Thr Asp Glu Gln Ile Ile
            260                 265                 270

Asp Leu Ile Ile Thr Leu Ile Tyr Ser Gly Tyr Glu Thr Met Ser Thr
            275                 280                 285

Thr Ser Met Met Ala Val Lys Tyr Leu Ser Asp His Pro Lys Ala Leu
            290                 295                 300

Glu Gln Leu Arg Lys Glu His Phe Asp Ile Arg Lys Gly Lys Ala Pro
305                 310                 315                 320

Glu Asp Ala Ile Asp Trp Asn Asp Phe Lys Ser Met Thr Phe Thr Arg
            325                 330                 335

Ala Val Ile Phe Glu Thr Leu Arg Leu Ala Thr Val Val Asn Gly Leu
            340                 345                 350

Leu Arg Lys Thr Thr Gln Asp Val Glu Met Asn Gly Tyr Val Ile Pro
            355                 360                 365

Lys Gly Trp Arg Ile Tyr Val Tyr Thr Arg Glu Ile Asn Tyr Asp Pro
            370                 375                 380

Phe Leu Tyr Pro Asp Pro Met Thr Phe Asn Pro Trp Arg Trp Leu Glu
385                 390                 395                 400

Lys Asn Met Glu Ser His Pro His Phe Met Leu Phe Gly Gly Gly Ser
            405                 410                 415

Arg Met Cys Pro Gly Lys Glu Val Gly Thr Val Glu Ile Ala Thr Phe
            420                 425                 430

Leu His Tyr Phe Val Thr Gln Tyr Arg Trp Glu Glu Gly Asn Asn
            435                 440                 445

Thr Ile Leu Lys Phe Pro Arg Val Glu Ala Pro Asn Gly Leu His Ile
450                 455                 460

Arg Val Gln Asp Tyr
465

<210> SEQ ID NO 31
<211> LENGTH: 923
<212> TYPE: DNA
<213> ORGANISM: Oryza sativa
<220> FEATURE:
<221> NAME/KEY: CDS
<222> LOCATION: (1)..(921)
<223> OTHER INFORMATION:

<400> SEQUENCE: 31 gca aat ggc tta caa gca tat gca gtg acc ttg ata aca tac ctg agc     48
Ala Asn Gly Leu Gln Ala Tyr Ala Val Thr Leu Ile Thr Tyr Leu Ser
1               5                   10                  15 ctg tgg tgg ttt gga att ttt aac cct gca ata gta tac gat cac ttg     96
Leu Trp Trp Phe Gly Ile Phe Asn Pro Ala Ile Val Tyr Asp His Leu
```

```
                20              25              30
ggg gaa ata tac tct gct ctt gta ttt gga agc ttt gtg ttc tgt att      144
Gly Glu Ile Tyr Ser Ala Leu Val Phe Gly Ser Phe Val Phe Cys Ile
         35              40              45 ttt ctg tac ata aag ggt cat ctt gct cca tct tca tct gat tct gga      192
Phe Leu Tyr Ile Lys Gly His Leu Ala Pro Ser Ser Ser Asp Ser Gly
 50              55              60 tcc tca ggg aat gtg ata att gat ttc tac tgg gga atg gaa cta tat      240
Ser Ser Gly Asn Val Ile Ile Asp Phe Tyr Trp Gly Met Glu Leu Tyr
 65              70              75              80 cct cgc att ggt aag cac ttt gat atc aaa gtg ttc aca aac tgc cgt      288
Pro Arg Ile Gly Lys His Phe Asp Ile Lys Val Phe Thr Asn Cys Arg
             85              90              95 ttt ggg atg atg tcc tgg gct gtt ctt gct gta acc tac tgc ata aag      336
Phe Gly Met Met Ser Trp Ala Val Leu Ala Val Thr Tyr Cys Ile Lys
            100             105             110 cag tat gaa atg aat ggc cga gtt gca gat tca atg ctt gtg aat act      384
Gln Tyr Glu Met Asn Gly Arg Val Ala Asp Ser Met Leu Val Asn Thr
        115             120             125 gca ttg atg ttg atc tat gtc acc aag ttc ttc tgg tgg gaa tct gga      432
Ala Leu Met Leu Ile Tyr Val Thr Lys Phe Phe Trp Trp Glu Ser Gly
130             135             140 tac tgg tgc act atg gac att gct cat gat aga gct ggt ttc tac att      480
Tyr Trp Cys Thr Met Asp Ile Ala His Asp Arg Ala Gly Phe Tyr Ile
145             150             155             160 tgc tgg gga tgc ttg gta tgg gtt cca tca ata tac acc tct cct gga      528
Cys Trp Gly Cys Leu Val Trp Val Pro Ser Ile Tyr Thr Ser Pro Gly
            165             170             175 atg tac ctt gtc aac cac cct gtg aat ttg ggt ccc cag tta cca ttt      576
Met Tyr Leu Val Asn His Pro Val Asn Leu Gly Pro Gln Leu Pro Phe
        180             185             190 tca ttt ttc ctg gtt gga ata tgg tgc ata tat ata aac tat gac tgt      624
Ser Phe Phe Leu Val Gly Ile Trp Cys Ile Tyr Ile Asn Tyr Asp Cys
    195             200             205 gtt cgt cag cgc caa gaa ttc cgt cgg aca aat ggg aaa tgc tca ata      672
Val Arg Gln Arg Gln Glu Phe Arg Arg Thr Asn Gly Lys Cys Ser Ile
210             215             220 tgg ggc aaa gct cca tct aag att gtt gct tcc tat cag act aca aat      720
Trp Gly Lys Ala Pro Ser Lys Ile Val Ala Ser Tyr Gln Thr Thr Asn
225             230             235             240 gga gaa aca aaa agc agt ctt ctc ttg act tct gga tgg tgg ggc ttg      768
Gly Glu Thr Lys Ser Ser Leu Leu Leu Thr Ser Gly Trp Trp Gly Leu
            245             250             255 tct cgt cat ttt cac tat gtt cca gag att cta tct gct ttt ttc tgg      816
Ser Arg His Phe His Tyr Val Pro Glu Ile Leu Ser Ala Phe Phe Trp
        260             265             270 aca gtt cca gct ctt ttt gat cat ttc ctg ccg tac ttc tat gtg atc      864
Thr Val Pro Ala Leu Phe Asp His Phe Leu Pro Tyr Phe Tyr Val Ile
    275             280             285 ttt ctg acc ata ttg ctg ttc gac cga gct aaa agg gat gat gac cga      912
Phe Leu Thr Ile Leu Leu Phe Asp Arg Ala Lys Arg Asp Asp Asp Arg
290             295             300 tgc tca tca aa                                                       923
Cys Ser Ser
305

<210> SEQ ID NO 32
<211> LENGTH: 307
<212> TYPE: PRT
<213> ORGANISM: Oryza sativa
```

<400> SEQUENCE: 32

```
Ala Asn Gly Leu Gln Ala Tyr Ala Val Thr Leu Ile Thr Tyr Leu Ser
  1               5                  10                  15
Leu Trp Trp Phe Gly Ile Phe Asn Pro Ala Ile Val Tyr Asp His Leu
             20                  25                  30
Gly Glu Ile Tyr Ser Ala Leu Val Phe Gly Ser Phe Val Phe Cys Ile
         35                  40                  45
Phe Leu Tyr Ile Lys Gly His Leu Ala Pro Ser Ser Asp Ser Gly
     50                  55                  60
Ser Ser Gly Asn Val Ile Ile Asp Phe Tyr Trp Gly Met Glu Leu Tyr
 65                  70                  75                  80
Pro Arg Ile Gly Lys His Phe Asp Ile Lys Val Phe Thr Asn Cys Arg
                 85                  90                  95
Phe Gly Met Met Ser Trp Ala Val Leu Ala Val Thr Tyr Cys Ile Lys
             100                 105                 110
Gln Tyr Glu Met Asn Gly Arg Val Ala Asp Ser Met Leu Val Asn Thr
         115                 120                 125
Ala Leu Met Leu Ile Tyr Val Thr Lys Phe Phe Trp Trp Glu Ser Gly
    130                 135                 140
Tyr Trp Cys Thr Met Asp Ile Ala His Asp Arg Ala Gly Phe Tyr Ile
145                 150                 155                 160
Cys Trp Gly Cys Leu Val Trp Val Pro Ser Ile Tyr Thr Ser Pro Gly
                165                 170                 175
Met Tyr Leu Val Asn His Pro Val Asn Leu Gly Pro Gln Leu Pro Phe
            180                 185                 190
Ser Phe Phe Leu Val Gly Ile Trp Cys Ile Tyr Ile Asn Tyr Asp Cys
        195                 200                 205
Val Arg Gln Arg Gln Glu Phe Arg Arg Thr Asn Gly Lys Cys Ser Ile
    210                 215                 220
Trp Gly Lys Ala Pro Ser Lys Ile Val Ala Ser Tyr Gln Thr Thr Asn
225                 230                 235                 240
Gly Glu Thr Lys Ser Ser Leu Leu Leu Thr Ser Gly Trp Trp Gly Leu
                245                 250                 255
Ser Arg His Phe His Tyr Val Pro Glu Ile Leu Ser Ala Phe Phe Trp
            260                 265                 270
Thr Val Pro Ala Leu Phe Asp His Phe Leu Pro Tyr Phe Tyr Val Ile
        275                 280                 285
Phe Leu Thr Ile Leu Leu Phe Asp Arg Ala Lys Arg Asp Asp Asp Arg
    290                 295                 300
Cys Ser Ser
305
```

<210> SEQ ID NO 33
<211> LENGTH: 825
<212> TYPE: DNA
<213> ORGANISM: Oryza sativa
<220> FEATURE:
<221> NAME/KEY: CDS
<222> LOCATION: (1)..(825)
<223> OTHER INFORMATION:

<400> SEQUENCE: 33

```
atg gcg ggc ggc ggc ggc gag tac ctg cgc cag ttc gtc gag gag acg    48
Met Ala Gly Gly Gly Gly Glu Tyr Leu Arg Gln Phe Val Glu Glu Thr
  1               5                  10                  15
```

| | | |
|---|---|---|
| gcc tgg tac aac gag atc ttc ctc agc cat gtg gtc ccg ggc gac tgg<br>Ala Trp Tyr Asn Glu Ile Phe Leu Ser His Val Val Pro Gly Asp Trp<br>20 25 30 | | 96 |
| tgg cgc gcc ctc ccc cac ccg ctc cag tcg tgg ctc cgc aac ggc ctc<br>Trp Arg Ala Leu Pro His Pro Leu Gln Ser Trp Leu Arg Asn Gly Leu<br>35 40 45 | | 144 |
| ggc ggc tac ctc atc tac ttc gcc tgc ggc ttc ctc tgg tgc ttc gtc<br>Gly Gly Tyr Leu Ile Tyr Phe Ala Cys Gly Phe Leu Trp Cys Phe Val<br>50 55 60 | | 192 |
| atc tac tac tgg aag cgc cac gcc tac atc ccc aaa gat tct ata cct<br>Ile Tyr Tyr Trp Lys Arg His Ala Tyr Ile Pro Lys Asp Ser Ile Pro<br>65 70 75 80 | | 240 |
| aca atc gaa gct atg aag aag caa ata att gtt gca tca aag gct atg<br>Thr Ile Glu Ala Met Lys Lys Gln Ile Ile Val Ala Ser Lys Ala Met<br>85 90 95 | | 288 |
| cct ctc tat tgt gcc ctt cca acc tta tct gag tac atg gtt gag aat<br>Pro Leu Tyr Cys Ala Leu Pro Thr Leu Ser Glu Tyr Met Val Glu Asn<br>100 105 110 | | 336 |
| gga tgg aca cag tgt tat gtt aat atc agt gaa gtt ggt tgg cca atg<br>Gly Trp Thr Gln Cys Tyr Val Asn Ile Ser Glu Val Gly Trp Pro Met<br>115 120 125 | | 384 |
| tac ctg gtt tat ctg gct tta tat ctt atc ttt gtt gag ttt gga att<br>Tyr Leu Val Tyr Leu Ala Leu Tyr Leu Ile Phe Val Glu Phe Gly Ile<br>130 135 140 | | 432 |
| tac tgg atg cac aga gag ttg cat gac ata aag cca ttg tac aag tac<br>Tyr Trp Met His Arg Glu Leu His Asp Ile Lys Pro Leu Tyr Lys Tyr<br>145 150 155 160 | | 480 |
| ctg cac aca tac cac cat att tac aac aag gag aat acc cta tca cca<br>Leu His Thr Tyr His His Ile Tyr Asn Lys Glu Asn Thr Leu Ser Pro<br>165 170 175 | | 528 |
| ttt gca gga cta gca ttc cat cca ctg gat ggg att ttg caa gcc ata<br>Phe Ala Gly Leu Ala Phe His Pro Leu Asp Gly Ile Leu Gln Ala Ile<br>180 185 190 | | 576 |
| ccg cat gtg ttt gcg ctc tac ctt atc cca aca cac ttc agg aca cac<br>Pro His Val Phe Ala Leu Tyr Leu Ile Pro Thr His Phe Arg Thr His<br>195 200 205 | | 624 |
| att gct ctc ttg ttc ata gag gcc gtg tgg aca act aac atc cat gac<br>Ile Ala Leu Leu Phe Ile Glu Ala Val Trp Thr Thr Asn Ile His Asp<br>210 215 220 | | 672 |
| tgc att cac ggc aag gtt tgg ccg gtc atg ggt gct ggc tat cac acc<br>Cys Ile His Gly Lys Val Trp Pro Val Met Gly Ala Gly Tyr His Thr<br>225 230 235 240 | | 720 |
| att cac cat aca aca tac cgt cac aac tat ggc cac tac acc gtg tgg<br>Ile His His Thr Thr Tyr Arg His Asn Tyr Gly His Tyr Thr Val Trp<br>245 250 255 | | 768 |
| atg gac tgg atg ttc ggc acc ctt cga gag cca gaa gat atc ttg aag<br>Met Asp Trp Met Phe Gly Thr Leu Arg Glu Pro Glu Asp Ile Leu Lys<br>260 265 270 | | 816 |
| aag gat tag<br>Lys Asp | | 825 |

<210> SEQ ID NO 34
<211> LENGTH: 274
<212> TYPE: PRT
<213> ORGANISM: Oryza sativa

<400> SEQUENCE: 34

Met Ala Gly Gly Gly Glu Tyr Leu Arg Gln Phe Val Glu Glu Thr
1               5                   10                  15

Ala Trp Tyr Asn Glu Ile Phe Leu Ser His Val Val Pro Gly Asp Trp

-continued

```
                    20                  25                  30
Trp Arg Ala Leu Pro His Pro Leu Gln Ser Trp Leu Arg Asn Gly Leu
                35                  40                  45
Gly Gly Tyr Leu Ile Tyr Phe Ala Cys Gly Phe Leu Trp Cys Phe Val
         50                  55                  60
Ile Tyr Tyr Trp Lys Arg His Ala Tyr Ile Pro Lys Asp Ser Ile Pro
 65                  70                  75                  80
Thr Ile Glu Ala Met Lys Lys Gln Ile Ile Val Ala Ser Lys Ala Met
                 85                  90                  95
Pro Leu Tyr Cys Ala Leu Pro Thr Leu Ser Glu Tyr Met Val Glu Asn
            100                 105                 110
Gly Trp Thr Gln Cys Tyr Val Asn Ile Ser Glu Val Gly Trp Pro Met
        115                 120                 125
Tyr Leu Val Tyr Leu Ala Leu Tyr Leu Ile Phe Val Glu Phe Gly Ile
    130                 135                 140
Tyr Trp Met His Arg Glu Leu His Asp Ile Lys Pro Leu Tyr Lys Tyr
145                 150                 155                 160
Leu His Thr Tyr His His Ile Tyr Asn Lys Glu Asn Thr Leu Ser Pro
                165                 170                 175
Phe Ala Gly Leu Ala Phe His Pro Leu Asp Gly Ile Leu Gln Ala Ile
            180                 185                 190
Pro His Val Phe Ala Leu Tyr Leu Ile Pro Thr His Phe Arg Thr His
        195                 200                 205
Ile Ala Leu Leu Phe Ile Glu Ala Val Trp Thr Thr Asn Ile His Asp
    210                 215                 220
Cys Ile His Gly Lys Val Trp Pro Val Met Gly Ala Gly Tyr His Thr
225                 230                 235                 240
Ile His His Thr Thr Tyr Arg His Asn Tyr Gly His Tyr Thr Val Trp
                245                 250                 255
Met Asp Trp Met Phe Gly Thr Leu Arg Glu Pro Glu Asp Ile Leu Lys
            260                 265                 270
Lys Asp

<210> SEQ ID NO 35
<211> LENGTH: 147
<212> TYPE: DNA
<213> ORGANISM: Oryza sativa
<220> FEATURE:
<221> NAME/KEY: CDS
<222> LOCATION: (1)..(147)
<223> OTHER INFORMATION:

<400> SEQUENCE: 35 ctg gaa gct tcc atc ttc ctt cac cac ttg gtc acc agc ttc agg tgg      48
Leu Glu Ala Ser Ile Phe Leu His His Leu Val Thr Ser Phe Arg Trp
 1               5                  10                  15 gtg gcg gag gag gac cac atc gtc aac ttc ccc acc gtg cgg ctc aag      96
Val Ala Glu Glu Asp His Ile Val Asn Phe Pro Thr Val Arg Leu Lys
                20                  25                  30 cgg ggc atg ccc atc agg gtc acc gca agg agg acg acg act agc cac     144
Arg Gly Met Pro Ile Arg Val Thr Ala Arg Arg Thr Thr Thr Ser His
            35                  40                  45 tag                                                                 147

<210> SEQ ID NO 36
<211> LENGTH: 48
<212> TYPE: PRT
```

<213> ORGANISM: Oryza sativa

<400> SEQUENCE: 36

| Leu | Glu | Ala | Ser | Ile | Phe | Leu | His | His | Leu | Val | Thr | Ser | Phe | Arg | Trp |
|---|---|---|---|---|---|---|---|---|---|---|---|---|---|---|---|
| 1 | | | | 5 | | | | | 10 | | | | | 15 | |

| Val | Ala | Glu | Glu | Asp | His | Ile | Val | Asn | Phe | Pro | Thr | Val | Arg | Leu | Lys |
|---|---|---|---|---|---|---|---|---|---|---|---|---|---|---|---|
| | | | 20 | | | | | 25 | | | | | 30 | | |

| Arg | Gly | Met | Pro | Ile | Arg | Val | Thr | Ala | Arg | Arg | Thr | Thr | Thr | Ser | His |
|---|---|---|---|---|---|---|---|---|---|---|---|---|---|---|---|
| | | | 35 | | | | 40 | | | | | 45 | | | |

<210> SEQ ID NO 37
<211> LENGTH: 645
<212> TYPE: DNA
<213> ORGANISM: Oryza sativa
<220> FEATURE:
<221> NAME/KEY: CDS
<222> LOCATION: (1)..(645)
<223> OTHER INFORMATION:

<400> SEQUENCE: 37

```
gtc att gct gac cgt gga atc gag ctg ttg tct aca acc ttc att ttt      48
Val Ile Ala Asp Arg Gly Ile Glu Leu Leu Ser Thr Thr Phe Ile Phe
 1               5                  10                  15 agt gtt att gtt acc ttc tta ctg tat tat tca gga tta agg tcc cat      96
Ser Val Ile Val Thr Phe Leu Leu Tyr Tyr Ser Gly Leu Arg Ser His
             20                  25                  30 cat aaa agt tct tcc ttg aaa ccg cat atc act ggg aac ttc ata caa     144
His Lys Ser Ser Ser Leu Lys Pro His Ile Thr Gly Asn Phe Ile Gln
         35                  40                  45 gat tgg tgg ttg gga gtg cag ctc aat cct cat ttc atg gga gtt gac     192
Asp Trp Trp Leu Gly Val Gln Leu Asn Pro His Phe Met Gly Val Asp
     50                  55                  60 ctc aag ttc ttt ttt gtg aga gct ggg atg atg gca tgg tta ttt atc     240
Leu Lys Phe Phe Phe Val Arg Ala Gly Met Met Ala Trp Leu Phe Ile
 65                  70                  75                  80 aac cta tct ttg ttt gca aag agc tac cta gct ggt tca gcc aat ctt     288
Asn Leu Ser Leu Phe Ala Lys Ser Tyr Leu Ala Gly Ser Ala Asn Leu
                 85                  90                  95 tca gtc att ctc tac caa ttc ttt tgt gcg tgg tat att gta gat tac     336
Ser Val Ile Leu Tyr Gln Phe Phe Cys Ala Trp Tyr Ile Val Asp Tyr
            100                 105                 110 ttc gtt cat gaa gaa ttc atg act tca aca tgg gac att att gcg gaa     384
Phe Val His Glu Glu Phe Met Thr Ser Thr Trp Asp Ile Ile Ala Glu
        115                 120                 125 agg ctg ggt ttc atg ctg gtc ttt ggt gat cta gtg ttc att cca ttt     432
Arg Leu Gly Phe Met Leu Val Phe Gly Asp Leu Val Phe Ile Pro Phe
    130                 135                 140 acc ttc acc att cag gga tgg tgg ctt ttg aga aac aaa gtg gag ctg     480
Thr Phe Thr Ile Gln Gly Trp Trp Leu Leu Arg Asn Lys Val Glu Leu
145                 150                 155                 160 tcc ctt ttg gct gct gta gtt aac tgc ttc att ttc gtt att ggc tat     528
Ser Leu Leu Ala Ala Val Val Asn Cys Phe Ile Phe Val Ile Gly Tyr
                165                 170                 175 ctt gtg ttc aga gga gcc aac aaa caa aaa cat atc ttc aag aag aac     576
Leu Val Phe Arg Gly Ala Asn Lys Gln Lys His Ile Phe Lys Lys Asn
            180                 185                 190 cct aaa gct ctt att tgg ggt aaa cct ccc aaa ctt gtc ggg ggg aag     624
Pro Lys Ala Leu Ile Trp Gly Lys Pro Pro Lys Leu Val Gly Gly Lys
        195                 200                 205 cta ctt gta tct ggc tac tgg                                          645
Leu Leu Val Ser Gly Tyr Trp
```

-continued

```
                 210                 215

<210> SEQ ID NO 38
<211> LENGTH: 215
<212> TYPE: PRT
<213> ORGANISM: Oryza sativa

<400> SEQUENCE: 38

Val Ile Ala Asp Arg Gly Ile Glu Leu Leu Ser Thr Thr Phe Ile Phe
1               5                   10                  15

Ser Val Ile Val Thr Phe Leu Leu Tyr Tyr Ser Gly Leu Arg Ser His
            20                  25                  30

His Lys Ser Ser Ser Leu Lys Pro His Ile Thr Gly Asn Phe Ile Gln
            35                  40                  45

Asp Trp Trp Leu Gly Val Gln Leu Asn Pro His Phe Met Gly Val Asp
        50                  55                  60

Leu Lys Phe Phe Phe Val Arg Ala Gly Met Met Ala Trp Leu Phe Ile
65                  70                  75                  80

Asn Leu Ser Leu Phe Ala Lys Ser Tyr Leu Ala Gly Ser Ala Asn Leu
                85                  90                  95

Ser Val Ile Leu Tyr Gln Phe Phe Cys Ala Trp Tyr Ile Val Asp Tyr
            100                 105                 110

Phe Val His Glu Glu Phe Met Thr Ser Thr Trp Asp Ile Ile Ala Glu
            115                 120                 125

Arg Leu Gly Phe Met Leu Val Phe Gly Asp Leu Val Phe Ile Pro Phe
        130                 135                 140

Thr Phe Thr Ile Gln Gly Trp Trp Leu Leu Arg Asn Lys Val Glu Leu
145                 150                 155                 160

Ser Leu Leu Ala Ala Val Val Asn Cys Phe Ile Phe Val Ile Gly Tyr
                165                 170                 175

Leu Val Phe Arg Gly Ala Asn Lys Gln Lys His Ile Phe Lys Lys Asn
            180                 185                 190

Pro Lys Ala Leu Ile Trp Gly Lys Pro Pro Lys Leu Val Gly Gly Lys
            195                 200                 205

Leu Leu Val Ser Gly Tyr Trp
            210                 215
```

US 7,408,100 B2

METHOD OF CONTROLLING CHARACTER OF MONOCOTYLEDON BY MODIFICATION AND/OR OVEREXPRESSION OF CYTOCHROME P450 MONOOXYGENASE GENE INVOLVED IN BRASSINOSTEROID BIOSYNTHESIS AND MONOCOTYLEDON MODIFIED BY THE GENE

This application claims priority to Japanese application no. 2002-276398 filed Sep. 20, 2002, which is incorporated herein by reference.

BACKGROUND OF THE INVENTION

1. Field of the Invention

The present invention relates to a method for controlling a character (e.g., a morphology and a yield) of monocotyledonous plants, and a transformed plant produced by controlling a character thereof.

2. Description of the Related Art

A technique of producing plants, particularly major cereals, having a desired character (e.g., a desired morphology and an increased yield) by controlling a character (e.g., a morphology) of the plant, is considerably useful in the agriculture field.

For example, if rice is modified into a short culm (semidwarf) morphology, abnormal elongation of stems or leaves of the plant due to supply of a fertilizer is suppressed. In this case, resistance to lodging due to physical force, such as wind or the like, is improved, resulting in resistance to a high level of fertilizer. Further, the proportion of fertilizers or anabolites distributed to stems and leaves is relatively decreased in association with the suppression of elongation, while the proportion of fertilizers or anabolites distributed to the growth of spikes is relatively increased. As a result, the growth of spikes is promoted in the modified plant, thereby increasing the yield. Alternatively, a variant of rice, which is modified to have erected leaves, has an improved level of light interception as compared to wild type rice. For such a variant rice, an area under an individual plant required for receiving a necessary amount of sun light can be reduced. As a result, the amount of cultivation per unit area can be increased.

However, when conventional methods are used to produce plants having such a morphology as erected leaf, short culm, and the like, the growth of spikes of the plant is inhibited, resulting in a reduction in yield.

To date, no method for producing a useful variety having a desired character, such as a beneficial morphology (erected leaf, short culm, or the like), no reduction in yields, and the like, has been known. Therefore, there is a demand for a method for producing useful plant varieties having a desired character, and plants, seeds, plant cells, and whole plants produced by the method.

As a plant hormone relating to control of the morphology of plants, brassinosteroid is well known. Brassinosteroid is a general term for plant growth regulatory hormones having a steroid lactone structure, including brassinolide.

In 1979, brassinolide was isolated as a novel plant growth-promoting factor from the pollen of rape (*Brassica napus*) and identified as a novel type of steroid lactone. It was thereafter found that brassinolide-like steroid compounds (referred to as brassinosteroid) occur at very low concentrations in all plant species examined (for review, see Mandava, Ann. Rev. Plant Physiol. Plant Mol. Biol. 39 (1988), 23-52). Initial studies of the physiological action of brassinosteroid showed that this particular factor (i) accelerated the germination and growth of plant seedlings at low temperatures, (ii) promoted the increase of cell size and elongation by induction of a longitudinal arrangement of cortical microtubule and cellulose microfilaments on the surface of cells, (iii) promoted xylem differentiation by amplifying the tracheal elements, (iv) resulted in significant increase in the dry weight of plants and their fruits, (v) promoted leaf unrolling and enlargement, (vi) induced $H^+$ export and membrane hyperpolarization characteristic for auxin induced cell growth, (vii) inhibited the division of crown-gall tumor cells and radial growth of stems, (viii) repressed anthocyanin production in light-grown plants, (ix) inhibited the de-etiolation induced, e.g. by cytokinin in the dark, (x) promoted tissue senescence in the dark, but prolonged the life-span of plants in the light, and (xi) induced plant pathogen resistance responses to numerous bacterial and fungal species (Mandava, Ann. Rev. Plant Physiol. Plant Mol. Biol. 39 (1988), 23-52).

Following the initial isolation of and physiological studies with brassinolides, numerous brassinosteroid compounds, representing putative biosynthetic intermediates, were identified in different plant species. Because the in vivo concentration of these compounds was found to be extremely low, efforts had been made to develop methods for chemical synthesis of these compounds (for review, see: Adam and Marquardt, Phytochem. 25 (1986), 1787-1799).

In order to be able to demonstrate that brassinosteroids can indeed be used as potential growth regulators of plants and to exploit the possible advantages and potentials of these substances, genes involved in synthesis and signal transduction of brassinosteroid have been isolated and analyzed.

For example, a d61 mutant lacking OsBRI1, which is a brassinosteroid receptor-like gene, was isolated from rice. Useful characters, such as erected leaf, semidwarf, and the like, were observed for the d61 mutant or plants in which the function of OSBRI1 is suppressed by an antisense nucleic acid, though the number of grains per spike was reduced and the size of grains was reduced, and the like, i.e., adverse effects on yield was confirmed (FIG. 1).

It might be possible that mutation relating to synthesis and/or signal transduction of brassinosteroid can be compensated for by exogenous brassinosteroid (e.g., by spraying or applying brassinosteroid) to avoid the adverse effects of the mutation. However, since d61 has a mutation in OsBRI1 (a brassinosteroid receptor-like gene), it is not possible to compensate for the phenotype thereof with exogenous brassinosteroid.

As a modified plant responsive to exogenous brassinosteroid, for example, plants having a mutation in a gene for a brassinosteroid synthesis system may be illustrated. However, plants having a mutation in a gene for a brassinosteroid synthesis system have been believed to not be able to be used to produce a good character according to previous findings described below.

For example, the cpd gene encoding a cytochrome P450 protein involved in brassinosteroid synthesis in plants has been identified for *Arabidopsis* (WO97/35986). It was reported that when grown in soil under white light, the size of cpd mutant plants, which have mutation in the cpd gene, was 20 to 30-fold smaller than that of the same age wild type plants. It was also reported that exposure to light induced greening and chloroplast differentiation in the periderm of mutant roots and resulted in a further inhibition of cell elongation, leading to an overall reduction of the length of petioles, leaves, inflorescence-stems and flower organs.

Choe et al. reported that the size of *Arabidopsis* plants having a mutation in DWF4, which is a cytochrome P450 monooxygenase enzyme involved in brassinosteroid biosynthesis, was several-fold smaller than that of wild type plants, i.e., superdwarfism, and that the plants are infertile (Sunghwa Choe et al., The Plant Cell, vol. 10, 231-243, February, 1998).

Choe et al. (The Plant Journal, vol. 26, 573-582, June, 2001) reported that the ratio of seed yield to plant height was not improved in the transgenic *Arabidopsis* overexpressing the DWF4 gene. Therefore, according to the above-described results for *Arabidopsis*, it has not been believed that modification and/or overexpression of DWF4 can be used in order to produce modified plants having a useful character.

Hong et al. (Hong Zhi et al., Proceedings of the 2002 Annual Meeting of the Japanese Society of Plant Physiologists, p. 224) and Mori et al. (Masaki Mori et al., Proceedings of the 2002 Annual Meeting of the Japanese Society of Plant Physiologists, p. 225) reported that substantially no leaf sheath was formed in rice plants having a mutation in OsDWARF which catalyzes oxidation activity at position C-6 of brassinosteroid, i.e., superdwarfism was shown along with extreme deformity. Therefore, similar to *Arabidopsis*, it has not been believed that modification and/or overexpression of a gene for a brassinosteroid biosynthesis or signal transduction system can be used in order to produce modified rice plants having a useful character.

Accordingly, although brassinosteroid was known as a plant hormone for controlling the morphology of plants, no method for using a gene for a brassinosteroid synthesis system was developed to produce plants having a useful character.

The present invention provides a method of producing a plant having a useful character using modification and/or overexpression of a gene for a brassinosteroid synthesis system, contrary to previous findings. The present invention also provides a plant, a plant seed, a plant cell and plant tissue produced by the method.

An object of the present invention is to provide a method of producing a useful plant variety having a desired morphology, and a plant, a seed, a plant cell, and plant tissue produced by the method, and the progeny of the plant. In the current situation there is no method of producing a plant having a desired morphology (particularly, short culm and/or verticality leading to improved light interception) and having substantially no adverse effect (e.g., reduction of yields) due to modification by controlling a character (e.g., a morphology) of plants.

According to previous findings, it was not believed that modification of a gene for a brassinosteroid synthesis system and/or signal transduction system allows for production of a useful plant variety having a useful character, such as a desired morphology. On the contrary, it is known that if a mutation is introduced into a gene for a brassinosteroid synthesis system and/or signal transduction system, a resultant mutant plant has a superdwarf morphology or an adversely affected yield. Such an adverse effect on yields has not been believed to be able to be removed. It was not believed that overexpression of a gene for a brassinosteroid synthesis system and/or signal transduction system allows for production of a plant having a useful character, such as an increase in yield.

Thus, it was not believed that modification and/or overexpression of a gene for a brassinosteroid synthesis system and/or signal transduction system allows for production of a plant having a useful character.

SUMMARY OF THE INVENTION

The present invention is partially based on a finding that modification of a cytochrome P450 monooxygenase gene involved in brassinosteroid biosynthesis allows for production of plants having a useful character (e.g., short culm and erected leaf) without an adverse effect (e.g., superdwarf morphology and a reduction in yield), contrary to the above-described recognition by those skilled in the art.

With a method of the present invention, a monocotyledonous plant having a desired morphology (e.g., short culm and/or verticality leading to improved light interception) can be produced. Further, with the method of the present invention, it is possible to avoid adverse effects, such as superdwarfism and a reduction in yield, and as a result, it is possible to confer a desired character to cereals or crops while maintaining the existing characters thereof.

Thus, the present invention provides the following.

1. A method of producing a modified monocotyledonous plant having a desired character, comprising:
   isolating a gene containing a nucleic acid hybridizable to a nucleic acid indicated by SEQ ID NO. 1 under stringent conditions; and
   inhibiting expression of the isolated gene.

2. A method according to item 1, wherein the desired character is short culm and/or erected leaf.

3. A method according to item 1, wherein the monocotyledonous plant is a poaceous plant.

4. A method according to item 3, wherein the poaceous plant is wheat.

5. A method according to item 3, wherein the poaceous plant is rice.

6. A method according to item 3, wherein the poaceous plant is maize.

7. A method according to item 1, wherein the expression inhibition is achieved by using an antisense nucleic acid or by homology dependent gene silencing.

8. A modified monocotyledonous plant according to item 1.

9. A seed of a monocotyledonous plant according to item 1.

10. A plant cell isolated from a monocotyledonous plant according to item 1.

11. Progeny of a monocotyledonous plant according to item 8.

12. A method of producing a modified monocotyledonous plant having a desired character, comprising:
    isolating the monocotyledonous plant having mutation in a gene containing a nucleic acid hybridizable to a nucleic acid having a sequence indicated by SEQ ID NO. 1 under stringent conditions.

13. A method according to item 12, wherein the desired character is short culm and/or erected leaf.

14. A method according to item 12, wherein the mutation is due to insertion of a transposon.

15. A method according to item 14, wherein the gene is disrupted by insertion of the transposon.

16. A method according to item 12, wherein the monocotyledonous plant is a poaceous plant.

17. A method according to item 16, wherein the poaceous plant is wheat.

18. A method according to item 16, wherein the poaceous plant is rice.

19. A method according to item 16, wherein the poaceous plant is maize.

20. A method according to item 12, further comprising inducing mutation in the gene.

21. A monocotyledonous plant according to item 12.

22. A seed of a monocotyledonous plant according to item 12.

23. A plant cell isolated from a monocotyledonous plant according to item 12.

24. Progeny of a monocotyledonous plant according to item 21.

25. Progeny of a monocotyledonous plant according to item 24, wherein both alleles of the gene are disrupted.

26. A method of producing a modified monocotyledonous plant having an increased yield, comprising:
   isolating a gene containing a nucleic acid hybridizable to a nucleic acid having a sequence indicated by SEQ ID NO. 1 under stringent conditions;
   constructing an expression vector for expressing the isolated gene in plants; and
   transforming monocotyledonous plants using the expression vector.

27. A method according to item 26, wherein the monocotyledonous plant is a poaceous plant.

28. A method according to item 27, wherein the poaceous plant is wheat.

29. A method according to item 27, wherein the poaceous plant is rice.

30. A method according to item 27, wherein the poaceous plant is maize.

31. A method according to item 26, wherein the expression vector includes a constitutive promoter, an inducible promoter, a site specific promoter, or a time specific promoter.

32. A method according to item 26, wherein the monocotyledonous plant to be transformed is a modified monocotyledonous plant according to item 8 or 21.

33. A modified monocotyledonous plant produced by a method according to item 26.

34. A seed of a modified monocotyledonous plant produced by a method according to item 26.

35. A plant cell isolated from a modified monocotyledonous plant produced by a method according to item 26.

36. Progeny of a modified monocotyledonous plant according to item 33.

37. A gene containing a nucleic acid hybridizable to a nucleic acid having a sequence indicated by SEQ ID NO. 1, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, or SEQ ID NO. 37 under stringent conditions, wherein when the gene is overexpressed in a monocotyledonous plant, a yield of the monocotyledonous plant can be increased.

38. A nucleic acid having a sequence indicated by SEQ ID NO. 1, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, or SEQ ID NO. 37.

39. A polypeptide having a sequence indicated by SEQ ID NO. 2, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, or SEQ ID NO. 38.

40. A nucleic acid encoding a polypeptide having a sequence indicated by SEQ ID NO. 2, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, or SEQ ID NO. 38.

41. An expression vector, comprising a gene according to item 37, a nucleic acid according to item 38 or 40, or a fragment thereof.

42. An expression vector according to item 41, further comprising a constitutive promoter, an inducible promoter, a site specific promoter, or a time specific promoter.

43. A polypeptide encoded by a gene according to item 37 or a nucleic acid according to item 38.

44. An antibody capable of binding to a polypeptide according to item 39 or 43.

45. An antibody according to item 44, wherein the antibody is a monoclonal antibody.

These and other advantages of the present invention will become apparent to those skilled in the art upon reading and understanding the following detailed description with reference to the accompanying figures.

BRIEF DESCRIPTION OF THE DRAWINGS

FIG. 1 shows photographs showing a difference in morphology phenotype between wild type rice (Nipponbare) and d61 mutant rice (Nipponbare). The d61 mutant has a useful character, such as erected leaf or semidwarf, unlike the wild type rice.

FIG. 4 shows the base sequence of the OsDWF4 gene and a putative amino acid sequence thereof.

FIG. 5 shows a comparison of base sequence between OsDWF4 and *Arabidopsis* DWF4.

FIG. 6 shows a comparison of putative amino acid sequence between OsDWF4 and *Arabidopsis* DWF4.

FIG. 9 shows a result of linkage analysis between phenotype and insertion of Tos17 by PCR for self-fertilized progeny of NE7040 which is one mutant line obtained by mutagenesis due to Tos17 insertion. +/+ indicates a plant without a Tos17 insertional mutation. +/− indicates a plant with heterozygous Tos17 insertional mutations. −/− indicates a plant with homozygous Tos17 insertional mutations. Any of plants showing the phenotypes of erected leaf and semidwarf had homozygous Tos17 insertional mutations. Plants showing the normal phenotype include plants with heterozygous Tos17 insertional mutations and plants without an insertional mutation at a ratio of 2 to 1.

DESCRIPTION OF THE PREFERRED EMBODIMENTS

Figure 2:
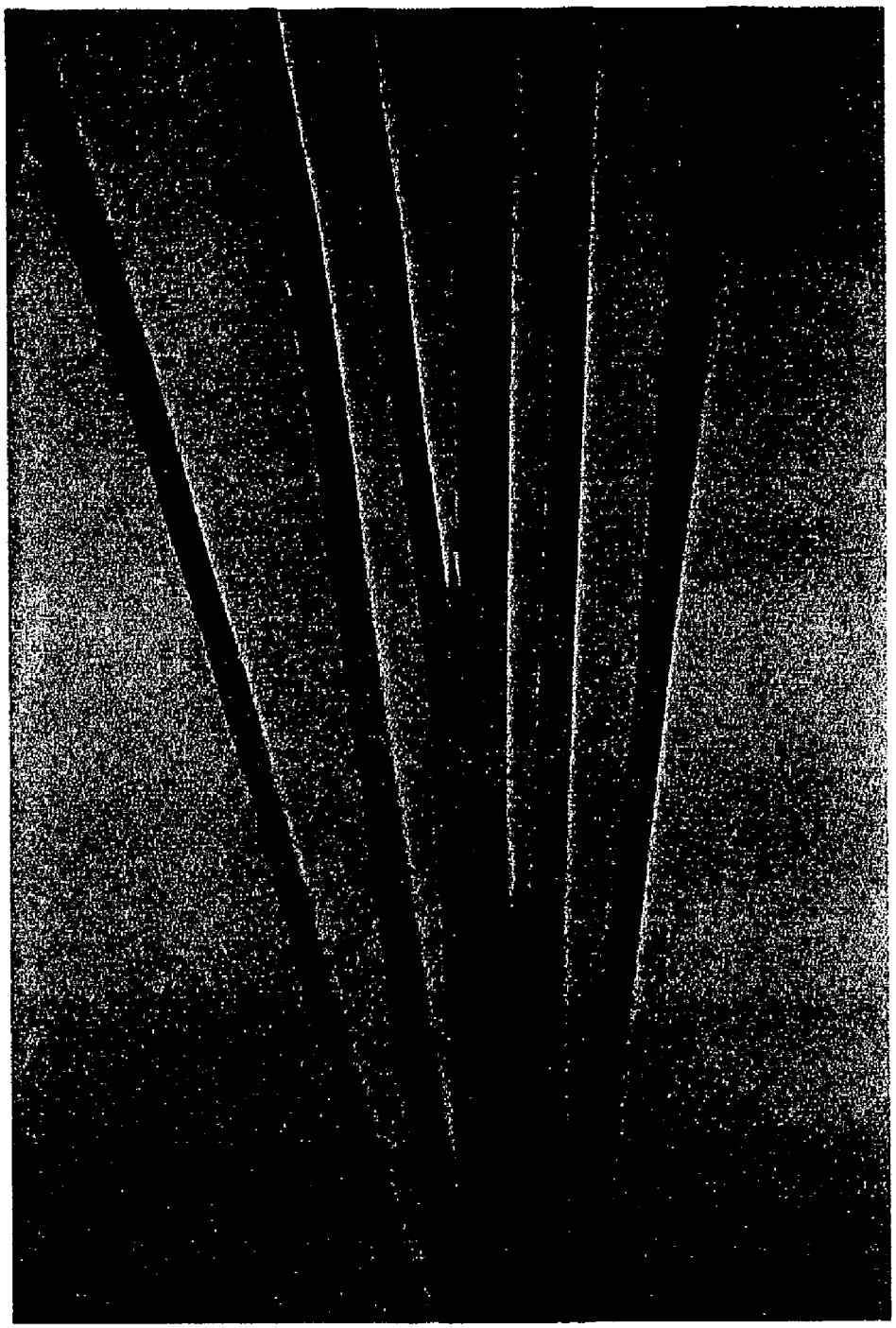
FIG. 2 shows that Tos2091 isolated in the present invention has a useful character, such as erected leaf or semidwarf.

It must be noted that, as used in the specification and the appended claims, the singular forms "a", "an" and "the" include plural referents unless the context clearly dictates otherwise. It must be also noted that, as used in the specification and the appended claims, the terms have definitions ordinarily used in the art unless the context clearly dictates otherwise.

The following terms as used herein have the meanings ascribed to them below.

As used herein, the term "plant" is a generic term encompassing organisms belonging to the plant kingdom, characteristically containing chlorophyll, having rigid cell walls, permanently producing abundant embryonic tissue, and lacking the power of locomotion. Representatively, a plant refers to a flowering plant which forms cell walls and has anabolism by chlorophyl. "Plant" includes any of monocotyledonous and dicotyledonous plants. Examples of monocotyledons include poaceous plants. Examples of preferable monocotyledons include, but are not limited to, maize, wheat, rice, oat, barley, Sorghum, rye, and millet, and more preferably maize, wheat, and rice. Examples of dicotyledons include, but are not limited to, brassicaceous plants, leguminous plants, solanaceous plants, cucurbitaceous plants, and convolvulaceous plants. A plant means any of whole plants, plant organs, plant tissues, plant cells and seeds unless otherwise specified. Examples of plant organs include root, leaf, stem, flower, and the like. Examples of plant cells include callus and a suspension of cultured cells. In a particular embodiment, a plant may refer to a whole plant.

Examples of poaceous plants include plants of the genera *Oryza, Triticum, Hordeum, Secale, Saccharum, Sorghum*, or *Zea* (e.g., rice, wheat, barley, rye, sugarcane, *Sorghum*, maize, and the like).

As used herein, the term "modified plant" refers to a plant in which at least a portion of the structures and/or functions of genomic information thereof is changed as compared to a naturally occurring plant. Such a modified plant may be produced, for example, by transformation of a wild type plant, crossbreed in with a transformed plant, suppression of gene expression with an antisense nucleic acid, suppression of gene expression by cosuppression, or the like. A method for producing a modified plant is not so limited.

As used herein, the term "transformation" and "gene introduction" are used interchangeably. "Transformation" indicates that an exogenous nucleic acid including a gene is introduced into plant cells or plant tissue, resulting in a change in the genotype of the plant cells or the plant tissue.

As used herein, the term "transformant" refers to the whole or a part of an organism, such as a cell, which is produced by transformation. Examples of a transformant include prokaryotic cells and plant cells. Transformants may be referred to as transformed cells, transformed tissue, transformed hosts, or the like, depending on the subject. As used herein, transformants encompass all of these forms, though a particular form may be intended in a particular context.

As used herein, the term "screening" refers to a step of distinguishing transformed plants having an introduced drug-resistance gene from untransformed plants by culturing and/or growing these plants in the presence of a drug.

Regarding genes, as used herein, the term "expression suppression" refers to a method of reducing the amount of products of transcription and/or translation of a gene of interest as compared to that of untreated plants. Examples of the "expression suppression" method include, but are not limited to, a method using an antisense nucleic acid technique, a homology dependent gene silencing technique, or the like; and mutagenesis.

As used herein, the term "antisense nucleic acid" refers to a nucleic acid molecule complementary to a messenger RNA (sense RNA) to be transcribed. Antisense nucleic acid may be obtained either by turning a fragment of a gene to be transcribed by 180 degrees, linking the fragment with a homologous or heterologous promoter/enhancer, and undergoing production of the fragment within cells or by synthesizing a nucleic acid having a sequence complementary to a sense RNA.

As used herein, the term "homology dependent gene silencing" refers to a phenomenon that causes a gene to be inactivated based on the homology of transgenes. Examples of gene silencing include cosuppression, paramutation, and promoter dependent silencing. A method using self-complementary "hairpin" RNA (hpRNA) described in Wesley et al. (Plant J., Sep. 27, 2001, 27(6):581-90) is also included in gene silencing.

Examples of a method of carrying out mutagenesis in a gene include, but are not limited to, a method using a mutagenic agent (e.g., alkylating agents, acridine dyes, and the like), a method of irradiating with ultraviolet light or radiation, and a method of introducing a transposon.

As used herein, the term "gene disruption" refers to a method of modifying a desired gene so that the gene cannot be expressed. A method of disrupting a plant gene is well known. Examples of such a method include, but are not limited to, a method of inserting a retrotransposon, and a method of using homologous recombination. Examples of retrotransposons include, but are not limited to, Tto1 and Tto2 (tobacco), Tos17 and Tos19 (rice), and Bs1 (maize).

As used herein, the term "transgenic plant" refers to a plant into which a particular gene is incorporated.

Plants can be herein cultivated by any known method in the art. Methods of cultivating plants are illustrated in, for example, "Moderu-shokubutsu-no-Jikken-Purotokoru, Ine・Shiroinunazuna: Saibo-kogaku Bessatsu-shokubutsu-saibo-kogakusirizu4; Ine-no-saibaiho [Experimental Protocol for Model Plants For Rice and *Arabidopsis thaliana*: Cellular Engineering, Special Issue, Plant Cellular Engineering Series 4; Rice Cultivating Methods]" (Kazutoshi Okuno) pp. 28-32, and "Arabidopushisu-no-saibaiho [Cultivating Methods for *Arabidopsis* ]" (Yasuo Tanba) pp. 33-40 (Supervised by Ko Shimamoto and Kiyotaka Okada), which are not herein described in detail.

As used herein, a gene to be introduced is a polynucleotide.

As used herein, the terms "polynucleotide", "oligonucleotide" and "nucleic acid" have the same meaning, referring to a polymer of nucleotides of any length. These terms also include "derivative oligonucleotide" or "derivative polynucleotide". The terms "derivative oligonucleotide" and "derivative polynucleotide" are interchangeably used to refer to oligonucleotides or polynucleotides containing a derivative of a nucleotide or having a different link between nucleotides from a normal link. Specifically, examples of such oligonucleotides include 2'-O-methyl-ribonucleotide, derivative oligonucleotides in which a phosphodiester linkage is converted to a phosphorothioate linkage, derivative oligonucleotides in which a phosphodiester linkage is converted to a N3'-P5' phosphoroamidate linkage, derivative oligonucleotides in which a ribose and a phosphodiester linkage are converted to a peptide nucleic acid linkage, derivative oligonucleotides in which uracil is substituted with C-5 propynyl uracil, derivative oligonucleotides in which uracil is substituted with C-5 thiazole uracil, derivative oligonucleotides in which cytosine is substituted with C-5 propynyl cytosine, derivative oligonucleotides in which cytosine is substituted with phenoxazine-modified cytosine, derivative oligonucleotides in which ribose is substituted with 2'-O-propylribose, and derivative oligonucleotides in which ribose is substituted with 2'-methoxyethoxyribose. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081(1991); Ohtsuka et al., J. Biol. Chem. 260:2605-2608(1985); Rossolini et al., Mol. Cell. Probes 8:91-98(1994)). The term "nucleic acid" is herein used interchangeably with "gene", "cDNA", "mRNA", "oligonucleotide", and "polynucleotide". A particular nucleic acid sequence also implicitly encompasses "splice variants". Similarly, a particular protein encoded by a nucleic acid implicitly encompasses any protein encoded by a splice variant of that nucleic acid. "Splice variants", as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

As used herein, "gene" refers to a factor defining a hereditary character. Genes are usually arranged in a predetermined order on a chromosome. A gene defining the primary structure of a protein is called a structural gene. A gene for controlling expression of a structural gene is called a regulatory gene. As used herein, "gene" also refers to "polynucleotide", "oligonucleotide", and "nucleic acid". As used herein, "homology" of a gene refers to the magnitude of identity between two or more gene sequences. Therefore, the greater the homology between two genes, the greater the identity or similarity between their sequences. Whether or not two genes have homology is determined by comparing their sequences directly or by a hybridization method under stringent conditions. When two gene sequences are directly compared with each other, the genes have homology if the DNA sequences of the genes have representatively at least 50%, preferably at least 70%, more preferably at least 80%, 90%, 95%, 96%, 97%, 98%, or 99% identity to each other.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, Molecular Cloning: A Laboratory Manual (2nd ed., Cold Spring Harbor Laboratory, 1989); Anderson et al., Nucleic Acid Hybridisation: A Practical Approach Ch. 4 (IRL Press Limited).

More stringent conditions (such as higher temperature, lower ionic strength, higher formamide, or other denaturing agents) may also be used, however, the rate of hybridization will be affected. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate, $NaDodSO_4$, (SDS), Ficoll, Denhardt's solution, sonicated salmon sperm DNA (or another noncomplementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridisation: A Practical Approach Ch. 4 (IRL Press Limited).

Factors affecting the stability of DNA duplex include base composition, length, and degree of base pair mismatch. Hybridization conditions can be adjusted by those skilled in the art in order to accommodate these variables and allow DNAs of different sequence relatedness to form hybrids. The melting temperature of a perfectly matched DNA duplex can be estimated by the following equation:

$$Tm(° C.)=81.5+16.6(\log [Na^+])+0.41(\% G+C)-600/N-0.72(\% \text{formamide})$$

where N is the length of the duplex formed, $[Na^+]$ is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions". For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, those skilled in the art can simply lower the temperature or raise the ionic strength.

A good estimate of the melting temperature in 1 M NaCl* for oligonucleotide probes up to about 20 nt is given by:

$$Tm=2° C. \text{ per } A\text{-}T \text{ base pair}+4° C. \text{ per } G\text{-}C \text{ base pair.}$$

* The sodium ion concentration in 6× salt sodium citrate (SSC) is 1 M. See Suggs et al., Developmental Biology Using Purified Genes 683 (Brown and Fox, eds., 1981).

High stringency washing conditions for oligonucleotides are usually at a temperature of 0-5° C. below the Tm of the oligonucleotide in 6×SSC, 0.1% SDS.

A comparison of identity between base sequences and a calculation of homology between sequences are calculated using a sequence analyzing tool BLAST with default parameters.

As used herein, "expression" of gene, polynucleotide, polypeptide, or the like, indicates that the gene or the like is subjected to a certain action in vivo and converted into another form. Preferably, a gene, a polynucleotide, or the like is subjected to transcription and translation into a polypeptide form, however, production of mRNA by transcription may be an embodiment of expression. More preferably, the form of such a polypeptide may be obtained by posttranslational processing.

As used herein, "nucleotide" may be naturally occurring or non-naturally occurring. "Derivative nucleotide" or "nucleotide analog" refers to a nucleotide which is different from a naturally-occurring nucleotide but has a function similar to that of the naturally-occurring nucleotide. Such a derivative nucleotide and nucleotide analog are well known in the art. Examples of such a derivative nucleotide and nucleotide analog include, but are not limited to, phosphorothioate, phosphoroamidate, methyl-phosphonate, chiral methyl-phosphonate, 2-O-methyl-ribonucleotide, and peptide nucleic acid (PNA).

As used herein, the term "fragment" refers to a polypeptide or polynucleotide having a sequence length of 1 to n−1 with respect to a full-length polypeptide or polynucleotide (its length is n). The length of a fragment may be appropriately changed depending on the purpose. For example, the lower limit of the length of a polypeptide is, for example, 3, 4, 5, 6, 7, 8, 9, 10, 15, 20, 25, 30, 40, 50 and more amino acids. Integers (e.g., 11 and the like), which are not herein illustrated, may also be appropriate as the lower limit. The lower limit of a polynucleotide is 5, 6, 7, 8, 9, 10, 15, 20, 25, 30, 40, 50, 75, 100 and more nucleotides. Integers (e.g., 11 and the like), which are not herein illustrated, may also be appropriate as the lower limit.

As used herein, the term "biological activity" refers to activity which a certain factor (e.g., polypeptides or proteins) may have in vivo, encompassing activity undergoing various functions. For example, when the certain factor is an enzyme, the biological activity thereof includes enzyme activity. Alternatively, when the certain factor is a ligand, the biological activity thereof includes binding of the ligand to a corresponding receptor. In the case of a protein having a function of binding to a heavy metal according to one embodiment of the present invention, the biological activity thereof includes at least activity to bind to a heavy metal. In another embodiment, biological activity includes both activity to bind to a heavy metal and ability to bind to a hydrophobic portion, such as plasma membrane.

As used herein, "variant polypeptide" or "variant polynucleotide" refers to such a substance as the original polypeptide or polynucleotide, a part of which is modified. Examples of such a variant include substitution variants, addition variants, deletion variants, truncated variants, and allelic variants. Allele refers to one member of a pair of distinct genetic variants located at the same gene locus on homologous chromosomes. Therefore, "allelic variant" refers to a variant allele of a certain gene. "Species homolog or homolog" refers to a gene which has homology (preferably at least 60% homology, and more preferably at least 80%, at least 85%, at least 90%, and at least 95%) to a predetermined gene in certain species at the amino acid or nucleotide level. A method for obtaining such a species homolog is clearly appreciated from the specification. "Ortholog" is also referred to as "orthologous gene". When two genes have similar or identical base sequences and are in different species derived from a common ancestor, the two genes are considered orthologs of each other. For example, in the case of the hemoglobin gene family having multigene structure, human and mouse α-hemoglobin genes are considered orthologs of each other, while human α-hemoglobin gene and human β-hemoglobin gene are considered paralogs of each other (due to gene duplication). Orthologs are useful for estimating the phylogenetic tree of molecules. An ortholog of the present invention may be useful in the present invention.

"Conservative (modified) variant" is applied to both an amino acid sequence and a nucleic acid sequence. For a particular nucleic acid sequence, a conservatively modified variant refers to a nucleic acid encoding the same or substantially the same amino acid sequence, or the substantially the same sequence if the nucleic acid does not encode an amino acid sequence. Due to degeneration of gene codes, a number of functionally identical nucleic acids encode a certain protein. For example, codons GCA, GCC, GCG, and GCU all encode amino acid alanine. Therefore, codons encoding alanine can be exchanged with other degenerate codons at their sites without changing a polypeptide sequence. Such a variation of a nucleic acid is referred to as "silent modification (mutation)" which is a type of conservatively modified mutation. All nucleic acid sequences encoding a polypeptide herein encompass all possible silent mutations of the nucleic acid. It should be appreciated that in the art, each codon in a nucleic acid may be modified while keeping a functionally identical molecule (except for AUG which is usually the unique codon for methionine and TGG which is usually the unique codon for tryptophan). Therefore, any nucleic acid sequence encoding a polypeptide herein implicitly includes a silent mutation thereof. Preferably, such modification may be performed while avoiding substitution of cysteine which is an amino acid having a large influence on the high-order structure of a polypeptide. More preferably, a polypeptide of the present invention may be modified such that cysteine is conserved in a heavy metal binding region and/or a farnesylated region.

In the specification, in order to produce a functionally equivalent polypeptide, an amino acid addition, a deletion, or a modification can be carried out in addition to an amino acid substitution. An amino acid substitution refers to replacement of an amino acid of an original peptide with one or more (e.g., 1 to 10, preferably 1 to 5, and more preferably 1 to 3) different amino acids. An amino acid addition refers to addition of one or more (e.g., 1 to 10, preferably 1 to 5, and more preferably 1 to 3) amino acids to an original peptide. An amino acid deletion refers to deletion of one or more (e.g., 1 to 10, preferably 1 to 5, and more preferably 1 to 3) amino acids from an original peptide chain. An amino acid modification includes, but is not limited to, amidation, carboxylation, sulfation, halogenation, alkylation, glycosylation, phosphorylation, hydroxylation, and acylation (e.g., acetylation). An amino acid to be substituted or added may be a naturally occurring amino acid, a non-naturally occurring amino acid, or an amino acid analog. A naturally occurring amino acid is preferable.

As used herein, the term "peptide analog" refers to a compound which is different from a peptide but equivalent to a peptide with respect to at least one chemical or biological function. Therefore, a peptide analog includes a peptide having addition or substitution of at least one amino acid analog. In a peptide analog, such an addition or substitution is made such that the function of the peptide analog is substantially the same as that of the original peptide (e.g., the similarity of a pKa value, the similarity of a functional group, the similarity of a binding form with other molecules, the similarity of solubility, and the like). Such a peptide analog can be produced using a well-known technique in the art. Therefore, a peptide analog may be a polymer including an amino acid analog.

As used herein, a nucleic acid form of a polypeptide refers to a nucleic acid molecule capable of expressing a protein form of the polypeptide. This nucleic acid molecule may have a nucleic acid sequence, a part of which is deleted or substituted with another base, or alternatively, into which another nucleic acid sequence is inserted, as long as an expressed polypeptide has substantially the same activity as that of a naturally occurring polypeptide (e.g., activity to bind to a heavy metal and activity to bind to a hydrophobic portion of membrane). Alternatively, another nucleic acid may be linked to the 5' end and/or the 3' end of the nucleic acid molecule. The nucleic acid molecule may be a nucleic acid molecule which is hybridizable to a gene encoding a polypeptide under stringent conditions and encodes a polypeptide having substantially the same function as that polypeptide. Such a gene is known in the art and is available in the present invention.

Such a nucleic acid can be obtained by a well known PCR technique, or alternatively, can be chemically synthesized. These methods may be combined with, for example, site-specific mutagenesis, hybridization, or the like.

As used herein, "substitution, addition, or deletion" of a polypeptide or a polynucleotide refers to replacement, addition, or removal of an amino acid or a substitute thereof, or a nucleotide or a substitute thereof, to an original polypeptide or polynucleotide. Such a substitution, addition, or deletion technique is well known in the art, including, for example, site specific mutagenesis. One or more substitutions, additions, or deletions may be introduced into a polypeptide or a polynucleotide as long as a resultant variant having the substitutions, additions, or deletions retains a function of interest (e.g., a cancer marker, a neurological disease marker, and the like). Preferably, for example, 20% or less, 10% or less of a full length variant may have substitutions, additions, or deletions, or there may be 100 or less, 50 or less, or 25 or less substitutions, additions, or deletions in a variant.

Polymer structure (e.g., polypeptide structure) may be described at various levels. General discussion of this structure is, for example, described in Alberts et al., Molecular Biology of the Cell (3rd Ed., 1994), and Cantor and Schimmel, Biophysical Chemistry Part I: The Conformation of Biological Macromolecules (1980). "Primary structure" refers to the amino acid sequence of a particular peptide. "Secondary structure" refers to local three-dimensional structures within a polypeptide. These structures are generally known as domains. A domain forms the packed unit of a polypeptide, representatively a portion of the polypeptide having 50 to 350 amino acids in length. A representative domain is made of portions, such as a β sheet (β strand or the like) and an α-helix stretch. "Tertiary structure" refers to the complete three-dimensional structure of a polypeptide monomer. "Quarternary structure" refers to a three-dimensional structure of independent tertiary units formed with noncovalent bonds. Terms relating to anisotropy are used in the same manner as for terms known in the energy field. Therefore, a polypeptide of the present invention may include a polypeptide having any amino acid sequence as long as it has high order structure having ability to bind to a heavy metal and ability to bind to a plasma membrane.

As used herein, "specific expression" of a gene indicates that the gene is expressed (preferably, at a higher level) at a specific site of a plant or a specific time different from other sites or times. Specific expression may be performed at a certain site (specific site) alone or along with other sites. Preferably, specific expression may be performed at a certain site alone.

General molecular biological techniques available in the present invention can be easily carried out by the those skilled in the art by referencing Ausubel F. A. et al. eds. (1988), Current Protocols in Molecular Biology, Wiley, New York, N.Y.; Sambrook J. et al., (1987) Molecular Cloning: A Laboratory Manual, 2nd Ed., Cold Spring Harbor Laboratory Press, Cold Spring Harbor, N.Y., or the like.

When mentioning genes in the present specification, "vector" refers to an agent which can transfer a polynucleotide sequence of interest to a target cell. Examples of such a vector include vectors which are capable of self replication or capable of being incorporated into a chromosome within host cells (e.g., prokaryotic cells, yeast, animal cells, plant cells, insect cells, whole animals, and whole plants, and preferably plant cells), and contain a promoter at a site suitable for transcription of a polynucleotide of the present invention.

"Expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes, and enhancers. It is well known to those skilled in the art that the type of an organism (e.g., a plant) expression vector and the type of a regulatory element may vary depending on the host cell. Examples of selectable markers for screening include, but are not limited to, drug-resistance genes, such as the neo gene encoding the enzyme neomycin phosphotransferase conferring resistance to the antibiotic kanamycin (Beck et al. (1982) Gene 19:327); the hyg gene encoding the enzyme hygromycin phosphotransferase conferring resistance to the antibiotic hygromycin (Gritz and Davies (1983) Gene 25:179); and the bar gene encoding phosphinothricin acetyl transferase conferring resistance to the herbicide phosphinothricin (EP 242236); the spt gene encoding streptomycin phosphotransferase; a streptomycin resistance gene; and a spectinomycin resistance gene (e.g., H. S. Chawla, 2002, Introduction to Plant Biotechnology 2nd, p. 363, Science Publishers, Inc. hardcover); and screenable marker genes, such as the gus gene encoding β-glucuronidase (Jefferson et al. (1986) Proc. Natl. Acad. Sci. USA 6:3901) and a luciferase gene (Ow et al. (1986) Science 234:856).

Examples of an agent used for screening in the present invention include, but are not limited to, kanamycin, hygromycin, geneticin, gentamicin, streptomycin, and spectinomycin.

"Recombinant vector" refers to a vector which can transfer a polynucleotide sequence of interest to a target cell. Examples of such a vector include vectors which are capable of self replication or capable of being incorporated into a chromosome within host cells (e.g., plant cells and whole plants), and contain a promoter at a site suitable for transcription of a polynucleotide of the present invention.

Examples of "recombinant vectors" for plant cells include Ti plasmid, tobacco mosaic virus vector, and Gemini virus vector.

A "terminator" is a sequence which is located downstream of a protein-encoding region of a gene and which is involved in the termination of transcription when DNA is transcribed into mRNA, and the addition of a poly A sequence. It is known that a terminator contributes to the stability of mRNA, and has an influence on the amount of gene expression. Examples of such a terminator include, but are not limited to, a CaMV35S terminator, a terminator for the nopaline synthetase gene (Tnos), and a terminator for the tobacco PR1a gene. As used herein, a "promoter" is a base sequence which determines the initiation site of transcription of a gene and is a DNA region which directly regulates the frequency of transcription. Transcription is started by RNA polymerase binding to a promoter. A promoter region is usually located within about 2 kbp upstream of the first exon of a putative protein coding region. Therefore, it is possible to estimate a promoter region by predicting a protein coding region in a genomic base sequence using a DNA analyzing software. A putative promoter region is usually located upstream of a structural gene. Preferably, a putative promoter region is located within about 2 kbp upstream of the translation initiation site of the first exon.

When mentioning gene expression in the present specification, "site specificity" generally refers to the expression specificity of a gene with respect to a site (e.g., in the case of plants; roots, stems, trunks, leaves, flowers, seeds, embryo buds, embryos, fruits, and the like) within an organism (e.g., plants). "Time specificity" refers to the expression specificity of a gene with respect to a developmental stage (e.g., in the case of plants, growth stage, and the number of days of a seedling after germination) of an organism (e.g., plants). Such specificity can be introduced into a desired organism using an appropriately selected promoter.

As used herein, the term "constitutive" for expression of a promoter of the present invention refers to a character of the promoter that the promoter is expressed in a substantially constant amount in all tissues of an organism no matter whether the growth stage of the organism is a juvenile phase or a mature phase. Specifically, when Northern blotting analysis is performed under the same conditions as those described in examples of the present specification, expression is considered to be constitutive according to the definition of the present invention if substantially the same amount of expression is observed at the same or corresponding site at any time (e.g., two or more time points (e.g., day 5 and day 15)), for example. Constitutive promoters are considered to play a role in maintaining the homeostasis of organisms in a normal growth environment. As used herein, "stress responsive" for promoter expression refers to a character of a promoter that when at least one stress is experienced by an organism, the expression amount of the promoter is changed. Particularly, a character of increasing an expression amount is referred to as "stress inducible". A character of reducing an expression amount is referred to as "stress suppressible". "Stress suppressible" expression is based on the premise that expression is observed in a normal situation. Therefore, this concept overlaps with "constitutive" expression. These characters can be determined by extracting RNA from any portion of an organism and analyzing the expression amount of the RNA by Northern blotting or quantitating expressed proteins by Western blotting. When a plant or a portion thereof (particular cells, tissue, or the like) is transformed with a vector comprising a stress inducible promoter and a nucleic acid encoding a polypeptide of the present invention, a stimulator having activity of inducing the promoter can be used to cause the particular gene to be expressed under predetermined conditions.

An "enhancer" may be used so as to enhance the expression efficiency of a gene of interest. As such an enhancer which is used in plants, an enhancer region containing an upstream sequence within the CaMV35S promoter is preferable. One or more enhancers may be used, or no enhancer may be used.

As used herein, the term "operatively linked" indicates that a desired sequence is located such that expression (operation) thereof is under control of a transcription and translation regulatory sequence (e.g., a promoter, an enhancer, and the like) or a translation regulatory sequence. In order for a promoter to be operatively linked to a gene, typically, the promoter is located immediately upstream of the gene. There may be an intervening sequence between a promoter and a structural gene. In other words, a promoter is not necessarily adjacent to a structural gene.

The presence of an introduced gene may be confirmed by Southern blotting. Expression of an introduced gene may be detected by Northern blotting or PCR. Expression of a protein, which is a gene product, may be confirmed by, for example, Western blotting.

Hereinafter, the present invention will be described by way of examples. Examples below are only for purposes of illustration. Therefore, the scope of the present invention is not limited to the above-described explanation or the examples below, except as by the appended claims.

EXAMPLES (Methods and Materials)

(Transformation)

Transformation is generally carried out by a method of directly introducing a gene into plants (direct gene introduction method), or a method of indirectly introducing a gene into plants (indirect gene introduction method).

To date, as an indirect gene introduction method, a method using *Agrobacterium* is widely used. For example, full mature seeds of rice are cultured; and after three weeks, callus obtained is infected with *Agrobacterium* (see Hiei et al., Plant Journal, 6:271-282, 1994), or seeds are infected with *Agrobacterium* 4-5 days after germination in order to quickly obtain transformants (Tanaka et al., JP No. 3141084).

As a direct gene introduction method, a particle gun method (see Christou, P. et al., Bio/Technology, 9:957-962, 1991), a polyethylene glycol method (Datta, S. K. et al., Bio/Technology, 8:736-740, 1990), an electroporation method (see Shimamoto, K. et al., Nature, 338:274-276, 1989), and the like are used for production of transformants. Electroporation refers to a method of introducing a gene into cells, in which a small hole is physically opened on a plant cell by applying direct current high voltage pulses, and a gene is introduced into the cell through the hole.

An advantage to these direct gene introduction methods is that culture and preparation of *Agrobacterium* are not required, as compared to indirect gene introduction methods. However, in the case of a particle gun method as a direct gene introduction method, there is a disadvantage that the efficiency of regeneration of transformed plants from transformed tissue is still low (Hagio, 1998, JARQ 32(4) 239-247).

When a gene is introduced into wheat, immature embryos are used (see J. T. Weeks et al., Plant. Physiol. 102:1077-1084, 1993). However, plants have to be grown in a field or a green house before obtaining immature embryos, and 6 to 7 months are required in fields and 3 to 5 months are required in green houses.

Example 1

Isolation of Rice Plants Having a Desired Character

Rice (Nipponbare) gene disruption lines (maintained and preserved in The Nagoya University Bioscience Center) having an insertional mutation of a retrotransposon Tos17 were searched for a mutated rice plant having desired characters, i.e. short culm and erected leaf. As a result, Tos2091 was identified (FIG. 2).

Example 2

Analysis of Tos2091

In the Tos2091 mutant, no linkage was recognized between the phenotype thereof (erected leaf or dwarfism) and the insertion of Tos17. Therefore, the Tos2091 mutant was considered to be derived from culture mutation. The Tos2091 mutant and indica rice Kasalath were crossbred to obtain an F2 isolation group, which was used to carry out mapping of a causative gene for the mutation.

(1: Mapping of a Causative Gene for the Tos2091 Mutant)

The chromosomal location of the Tos2091 mutation was identified using a progeny line of crossbred "Tos2091" (japonica) and "Kasalath" (indica). Linkage analysis was performed using a MAPMAKER program (Lander et al., 1987). The F2 isolation group was used for mapping of a causative gene for the mutation. As a result, it was demonstrated that the causative gene is located on the short arm of the third chromosome.

(2: Identification of a Causative Gene for the Tos2091 Mutant)

It is known that a brassinosteroid synthesis system involves several cytochrome P450 monooxygenases. Therefore, a plurality of cytochrome P450 monooxygenase-like gene fragments were isolated from rice and the chromosomal location of each fragment was analyzed as follows.

(2.1: Isolation of Rice Cytochrome P450 Monooxygenase-Like Genes)

Degenerate primers were designed based on the base sequence of a cytochrome P450 gene (Choe et al., 1998) isolated from *Arabidopsis thaliana*, which is involved in brassinosteroid biosynthesis: (5'-ACICARTGYGTIR-TIAAYGARACIYTIMG-3'; (SEQ ID NO. 39); and 5'-GCIARYTCIBWICCIGSRCAIARIC-3' SEQ ID NO. 40). PCR was carried out using the genomic DNA of rice "Nipponbare" as a template, and Pyrobest DNA polymerase (TaKaRa). Amplified fragments were cloned in a cloning vector pBluescript II (Clontech). Thereafter, the base sequence of the fragment was determined. The chromosomal location of each candidate gene was determined by the above-described method using a crossbred line of "Nipponbare" (japonica) and "Kasalath" (indica). Note that in the above-described nucleic acid sequences, I represents inosine, R represents adenine or guanine, Y represents cytosine, thymine or uracil, M represents adenine or cytosine, B represents cytosine, guanine, thymine or uracil, W represents adenine, thymine or uracil, and S represents cytosine or guanine.

(2.2: Identification of a Causative Gene for the Tos2091 Mutant)

As a result of analysis of the chromosomal location of each candidate gene, a cytochrome P450 monooxygenase-like gene was identified at substantially the same site as that of a Tos2091 causative gene. A BAC clone containing the candidate gene was obtained by screening using PCR. A specific primer used was designed based on the base sequences of the above-described PCR amplified fragments: (5'-GAAACGTGGTCAGGTTCCTGCA-3' SEQ ID NO. 3); and 5'-TGAAGCTGCTGCTCTGAGCCAA-3' SEQ ID NO. 4). The base sequence of the obtained BAC clone was determined, and the full length genomic sequence of the candidate gene was determined.

This candidate gene had 51.5% homology to the *Arabidopsis* DWARF4 (DWF4) gene with respect to the base sequence, and had 65.8% homology with respect to the amino acid sequence. Thus, the candidate gene of rice was inferred to be the counterpart of DWF4. This gene was designated OsDWF4.

It is known that DWF4 of *Arabidopsis* encodes cytochrome P450 monooxygenase involved in brassinosteroid biosynthesis. The open reading frame (ORF) of OsDWF4 has a length of 1518 bases (SEQ ID NO. 1), encoding a protein of 506 amino acids (SEQ ID NO. 2) (FIG. 4). The base sequence of OsDWF4 had 51% homology to the ORF of *Arabidopsis* (FIG. 5), and the putative amino acid sequence of OsDWF4 had 65.8% homology to an amino acid sequence of DWF4 (FIG. 6). Six characteristic domain structures of cytochrome P450 monooxygenase were all conserved in OsDWF4 (FIG. 5). According to these results, it was concluded that OsDWF4 of rice was the counterpart gene of the *Arabidopsis thaliana* DWF4 gene.

Figure 3:
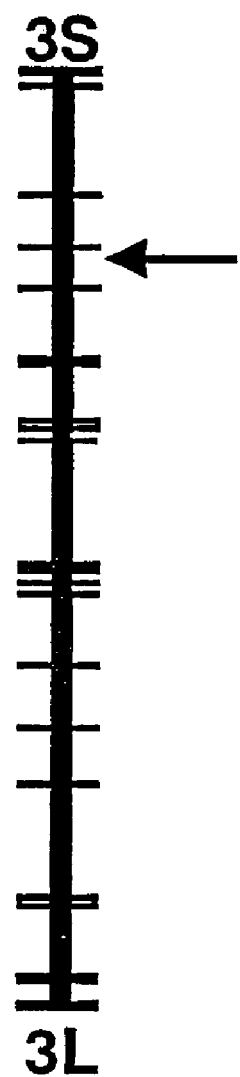
FIG. 3 shows a result of mapping of the OsDWF4 gene. It was demonstrated that the OsDWF4 gene is located on the short arm of the third chromosome as is the Tos2091 mutant causative gene.

Further, an F2 isolation group was used to carry out mapping of the OsDWF4 gene. It was demonstrated that the OsDWF4 gene is located on the short arm of the third chromosome, as is the Tos2091 mutant causative gene (FIG. 3).

In order to confirm that this gene is the Tos2091 mutant causative gene, a complementation test of Tos2091 was carried out based on the genomic sequence of OsDWF4.

An about 10 kbp genomic DNA sequence containing a coding region of OsDWF4 was obtained from the above-described BAC clone. This about 10 kbp genomic DNA sequence was cloned in a binary vector pCAMBIA 1300 (CAMBIA), which was introduced into the Tos2091 mutant using the Agrobacterium method. The gene introduction was carried out in accordance with a method described in Tanaka et al. (JP No. 3141084) using a bacterium strain *Agrobacterium tumefaciens* EHA105.

The phenotype of Tos2091 was restored in plants into which the about 10 kb genomic DNA containing a coding region of OsDWF4 had been introduced. Therefore, it was confirmed that the causative gene for the Tos2091 mutant is OsDWF4.

(3: Analysis of Expression of OsDWF4)

Total RNA extracted from each organ of rice "Nipponbare" was treated with DNase (NipponGene). Template cDNA for RT-PCR was produced using Advantage RT-for-PCR Kit (Clontech). TaKaRa Taq polymerase (TaKaRa) was used for PCR. As primers, (5'-GGTGTATAGCTAGCTTGCTTG-CAG-3'(SEQ ID NO. 5); and 5'-GAGAGCCTTCCAG-TAGGGCG-3' (SEQ ID NO. 6)were used.

Figure 7:
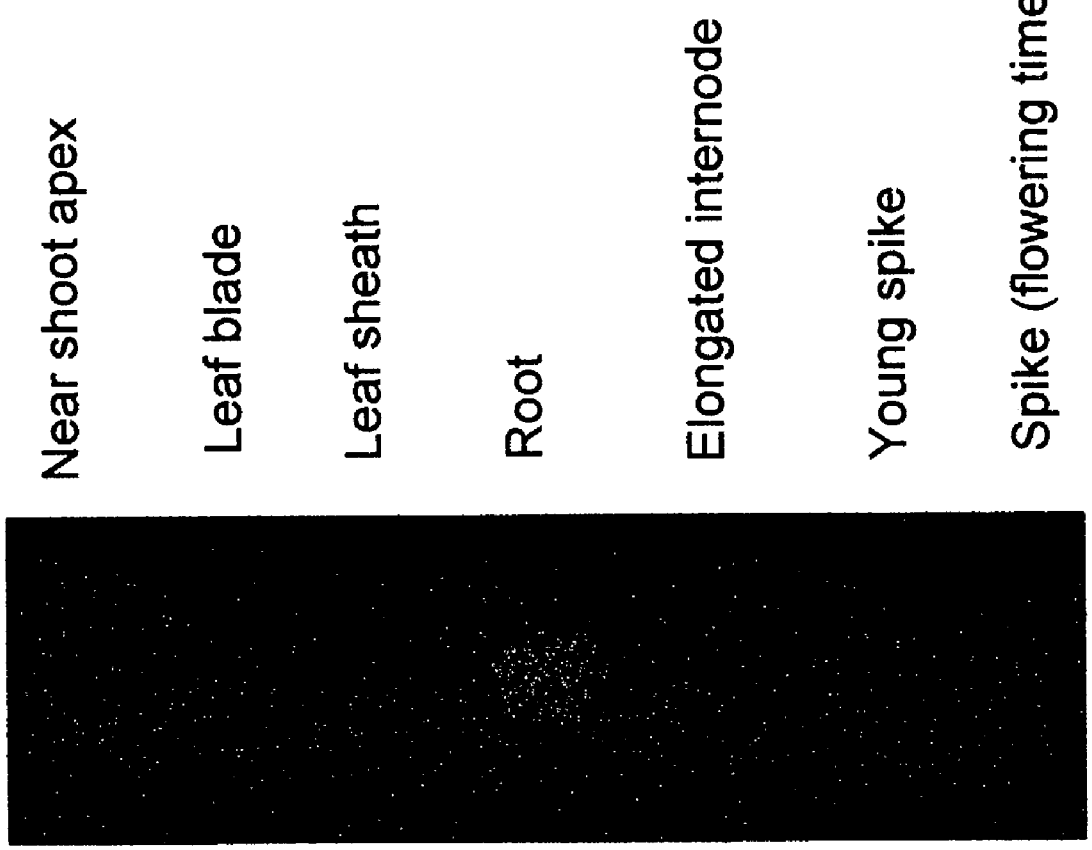
FIG. 7 shows the result of an investigation of tissue specificity of OsDWF4 expression by quantitative RT-PCR.

The tissue specificity of OsDWF4 expression was investigated by quantitative RT-PCR. As a result, it was found that OsDWF4 was expressed strongly in roots and slightly in the vicinity of shoot apex meristematic tissue. Expression was not recognized in leaf blades, leaf sheaths, elongated internodes, young spikes, and spikes in flowering time (FIG. 7).

(4: Obtaining of Another Mutant Line Lacking the Function of OsDWF4)

Figure 8:
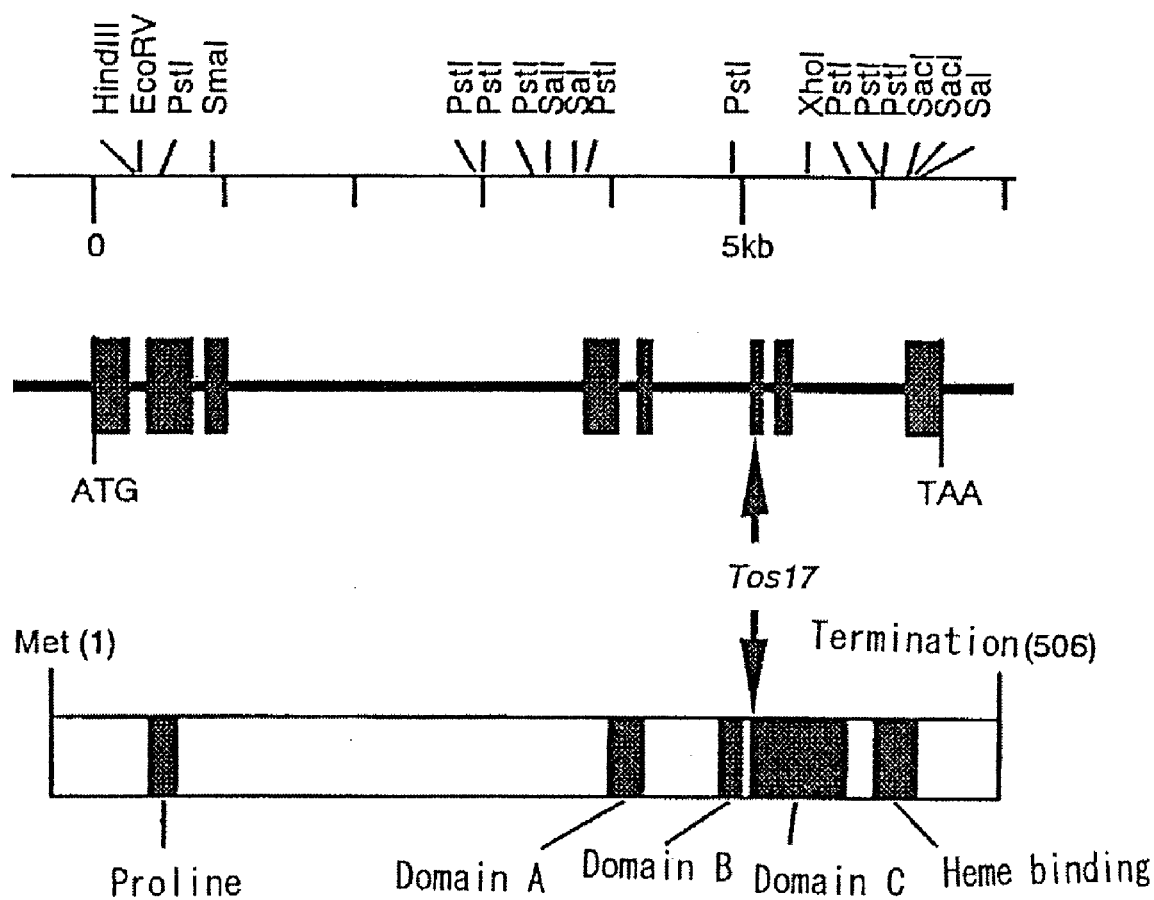
FIG. 8 shows that in a rice gene disruption line (NE7040) obtained by mutagenesis due to insertion of a retrotransposon Tos17 into the OsDWF4 gene, Tos17 was inserted into domain C which is one of six conserved domains characteristic to cytochrome P450 monooxygenase encoded by OsDWF4.

In order to obtain another mutant line lacking the function of OsDWF4, the full length genomic base sequence of OsDWF4 and a putative amino acid sequence thereof were used to carry out screening of a Tos17 mutant panel (National Institute of Agrobiological Science pc7080.abr.affrc.go.jp/~miyao/pub/tos17/). Insertion was detected using a primer pair: (5'-ACTGTATAGTTGGCCCATGTCCAG-3' SEQ ID NO. 7); and 5'-TAATCCTACTGCGACTGACCTTCC-3' SEQ ID NO. 8). Non-insertion was detected using a primer pair: (5'-TGTGGTGGTATCAGATAAAGGAGC-3'SEQ ID NO. 9); and 5'-TAATCCTACTGCGACTGACCTTCC-3' SEQ ID NO. 10). As a result, a rice gene disruption line (NE7040) was obtained, in which insertional mutation by the retrotransposon Tos17 was generated in domain C which is one of the six conservative characteristic domains of cytochrome P450 monooxygenase (FIG. 8).

Self-fertilized progeny of the obtained mutant line NE7040 were investigated for segregation of Tos17 insertional mutation. In a segregation generation, a homozygous wild type, a heterozygous insertional mutation type, and a homozygous insertional mutation type were segregated at a ratio of about 1:2:1.

Specifically, in the segregation generation, about 25% of plants showed the phenotypes of erected leaf and semidwarf, and the other plants showed a phenotype which was not distinguished from the phenotype of the wild type. The genotype of each plant was investigated. As a result, the plants showing the phenotypes of erected leaf and semidwarf all have homozygous Tos17 insertional mutation. Plants having the normal phenotype included plants having heterozygous Tos17 insertional mutation and plants without an insertional mutation at a ratio of about 2:1. Therefore, there was a correlation between the phenotype and genotype of the mutant. It was demonstrated that when Tos17 insertional mutation occurred homozygously so that the function of OsDWF4 was completely lost, the phenotypes of erected leaf and semidwarf were exhibited (FIG. 9). In the homozygous mutant, no undesired character, such as significant inhibition of the development of spikes or superdwarfism, was observed in contrast to d61.

While not wishing to be bound by theory, it is inferred that in monocotyledonous plants, enzyme reactions due to cytochrome P450 monooxygenase involved in brassinosteroid biosynthesis are catalyzed by enzymes encoded by a plurality of genes including the DWF4 gene.

There is a difference in the biological function of brassinosteroid between *Arabidopsis* and rice (e.g., Steven D. Clouse et al., Plant Physiol. (1996)111:671-678; Jianming Li and Joanne Chory, Cell, vol. 90, 929-938, Sep. 5, 1997; and Chizuko Yamamuro et al., The Plant Cell, vol. 12, 1591-1605, September 2000). There is also generally a difference in a biosynthesis pathway for a hormone or the like between dicotyledonous and monocotyledonous plants. Therefore, it is considered that in monocotyledonous plants, DWF4 mutants did not show such a character as superdwarfism, as they were different from dicotyledonous plants. It is also considered that the reason superdwarfism was shown when mutation was introduced into a receptor for brassinosteroid is that no gene substituting for the brassinosteroid receptor is present. According to these findings, it is expected that when mutation is introduced into the DWF4 gene, all monocotyledonous plants (of course, including rice) show preferable characters, such as short culm (semidwarf) and erected leaf, without an undesired character, such as superdwarfism.

Example 3

Production of DWF4 Gene Disruption Plants Using a Retrotransposon

A method of disrupting a gene on a plant chromosome is well known. Examples of such a gene disruption method include, but are not limited to, a method using a retrotransposon and a method using homologous recombination. Therefore, if OsDWF4 or the counterpart of a desired species is isolated, it is possible for those skilled in the art to easily obtain a DWF4 gene disruption plant in view of examples below and technical common knowledge.

(1: Production of Gene Disruption Plants)

A method of producing a gene disruption plant using a retrotransposon is well known as described in, for example, Hirohiko Hirochika et al., Proc. Natl. Acad. Sci. USA, vol. 93, 7783-7788 (July, 1996).

(2: Screening for a Gene Disruption Plant)

A method using PCR for easily determining whether or not a retrotransposon is inserted in a desired gene (three-dimensional screening using PCR) has been established (Akio Miyao and Hirohiko Hirotika, "Ine-no-Tos17-niyoru-Idenshihakaiho", Saibo-kogaku Bessatsu, Shokubutsu-saibo-kogaku sirizu 14; Shokubutsu-no-Genomu-Kenkyu-Purotokoru Saishin-no-Genomu-Jhoho-to-sono-Riyoho ["Gene Disruption Method using Rice Tos17", Cellular Engineering, Special Issue, Plant Cellular Engineering Series 14; Protocols for Plant Genome Research, Up-to-date Genome Information and its Applications], Shujyunsha, PP. 73-81, (2001)). A specific procedure will be described below.

```
(2.1.: Reagents)
1. Tos17 terminal primers for first screening:
T17F-1      ACCACTTCAGAGATTGTGTGGTTGC;  (SEQ ID NO.
            and                          11)

T17R-1      CAGCAACGATGTAGATGGTCAAGC.   (SEQ ID NO.
                                         12)

2. For (Nested) PCR:
T17F-2      GACAACACCGGAGCTATACAAATCG;  (SEQ ID NO.
                                         13)
```

```
                    -continued
T17R-2      AGGAGGTTGCTTAGCAGTGAAACG;   (SEQ ID NO.
                                         14)

T17LTRN6F   CTGTATAGTTGGCCCATGTCC; and  (SEQ ID NO.
                                         15)

T17LTR7R    ATGGACTGGACATCCGATGG.       (SEQ ID NO.
                                         16)
```

3. Taq polymerase (Expand Long Template PCR System, Boehringer-Mannheim, 3.5 u/μl).

(2.2: Confirmation by PCR)

A method for screening by PCR for a plant in which a retrotransposon is inserted into a desired gene is well known as disclosed in, for example, Ronald Koes et al., (Proc. Natl. Acad. Sci. USA, Vol. 92, August 1995, pp. 8149-8153).

Specifically, a plant in which a retrotransposon is inserted into a desired gene can be screened for using the following PCR.

1. Reaction mixture for PCR
Template DNA (10 ng/μl) 5 μl
(genomic DNA prepared from a plant to be subjected to screening)
10×PCR buffer 2 μl
2 mM dNTP 2 μl
2.5 mM MgCl$_2$ 2 μl
10 μM Tos17 primer 2 μl
10 μM optional primer 2 μl
Taq polymerase 0.5 μl
Distilled water is added to 20 μl.

2. PCR cycles
1 cycle of:
   94° C., 3 min,
10 cycles of:
   94° C., 30 sec;
   62° C., 30 sec; and
   68° C., 2 min,
20 cycles of:
   94° C., 30 sec;
   62° C., 30 sec; and
   68° C., 2 min (a 20-sec extension cycle is added to each cycle), and
1 cycle of:
   68° C., 10 min.

3. The reaction mixture was analyzed by 1% agarose gel electrophoresis. When amplification efficiency is poor, LA-Taq is used for PCR.

4. A base sequence located further inside of a gene of interest is used to produce a primer. PCR was performed again using this primer where 1 μl of a 20-fold dilute of the initial reaction solution is used as a template (final volume: 20 μl). When T17F-1 is used in the first PCR, two reactions are performed using T17F-2 and T17LTRN6F, respectively, in the second PCR. When T17R-1 is used, two R primers are similarly used. When a set of these primers are used, products having different sizes can be obtained, thereby making it possible to determine whether or not an amplification product is correct.

5. Southern analysis is performed to confirm that an amplification band is derived from a gene of interest.

(3: Screening for a Homozygous Mutant Plant)

A method of crossbreeding mutant plants is well known (e.g., Itsuro Takamure and Yoshio Sano, "Ine-no-Totsuzen-henitai-Yuhatsu, Senbatsu-to-Kohaiho", Saibo-kogaku Bessatsu, Shokubutsu-saibo-kogaku sirizu 4, Moderu-Shokubutsu-no-Jikken-Purotokoru, Ine Shiroinazuna-hen ["Mutagenesis, Screening, and Crossbreeding for Rice", Cellular Engineering, Special Issue, Plant Cellular Engineering Series 14; Experimental Protocols for Model Plants, For Rice• *Arabidopsis thaliana*], Shujunsha, pp. 44-48 (1996)).

Whether or not a progeny obtained by crossbreeding is a homozygous mutant plant is determined by Southern analysis as follows.

(3.1: Extraction of Genomic DNA)

Genomic DNA is extracted from a small scale CTAB method (M. G. Murray and W. F. Thompson (1980) Rapid isolation of high molecular weight plant DNA, Nucleic Acids Res. 8:4321-4325).

(3.1.1: Reagents)
1. 1.5×CTAB solution
   Cetyl trimethyl ammonium bromide 10 g
   1M Tris-HCl, pH 8.0 50 ml
   0.5M EDTA 20 ml
   NaCl 41 g
   polyvinyl pyrrolidone 5 g
   $H_2O$ is added to 750 ml.
2. Precipitation buffer
   Cetyl trimethyl ammonium bromide 10 g
   1M Tris-HCl, pH 8.0 50 ml
   0.5M EDTA 20 ml
   $H_2O$ is added to 1000 ml.
3. 1M NaCl-TE
   NaCl 58.4 g
   1M Tris-HCl, pH 8.0 10 ml
   0.5 M EDTA 2 ml
   $H_2O$ is added to 1000 ml.
4. Chloroform
5. Ethanol
6. TE (1 µg/ml RNase is added)

(3.1.2: Method)
1. Freeze about a leaf of rice with liquid nitrogen and pulverize with a mortar.
2. Transfer the pulverized leaf to an Eppendorf tube containing 0.7 ml of 1.5×CTAB solution using a spatula. (A transferred amount is such that when the tube falls down, the suspension is slowly moved.)
3. Add 0.5 ml of chloroform, followed by shaking for about 20 min at room temperature.
4. Centrifuge at 14,000 rpm for 5 min.
5. Transfer 0.5 ml of supernatant to a new tube and add 0.5 ml of precipitation buffer, followed by mixing.
6. Place the tube in a water bath at 55° C. for 30 min. (Precipitation occurs.)
7. Centrifuge at 14,000 rpm for 5 min.
8. Remove supernatant completely and add 0.5 ml of 1M NaCl-TE.
9. Place the tube in a water bath at 55° C. for 2 hours while mixing by inversion from time to time to dissolve precipitates.
10. Centrifuge at 14,000 rpm for 5 min to precipitate insolubles after DNA is completely dissolved.
11. Transfer supernatant to a new tube, and add 1 ml of ethanol, followed by thorough mixing.
12. Centrifuge at 14,000 rpm for 5 min.
13. Remove supernatant and add 1 ml of 70% ethanol to rinse precipitate and the wall of the tube.
14. Centrifuge at 14,000 rpm for 2 min.
15. Remove supernatant.
16. Centrifuge lightly again to collect remaining ethanol at the bottom of the tube, and remove the remaining ethanol completely with a pipetteman.
17. After the white precipitate is turned transparent in about 10 min by air drying, dissolve the precipitate in 50 µl of TE (+RNase). (The precipitate is difficult to dissolve. Stir patiently until the precipitate is dissolved.)
18. Take a sample of 2 µl and measure the concentration thereof using a fluorometer.
19. Dilute with TE to 50 ng/µl and preserve at −20° C. Amount of TE added=(concentration ng/50)×48−48.

(3.2: Agarose Gel Electrophoresis)
1. Digest 500 ng per lane with XbaI.
2. Electrophorese in 0.8% agarose gel, where 1.5 to 2 kb band will appear at the bottom of the gel. As a marker, λ/HindIII is used. As a control, Nipponbare/XbaI is electrophoresed in a lane. In order to obtain a clear electrophoretic image, the 2 kb band of λ needs to be electrophoresed at a distance of 18 to 20 cm from the well.
3. After electrophoresis, DNA is blotted onto nylon membrane (Hybond N+). Subject DNA transferred to the filter to alkaline denaturation for 5 min. Immerse the filter in a neutralization solution, followed by thorough shaking in 2×SSC. Remove excess SSC by sandwiching the filter with paper towel.
4. Irradiate the wet filter with UV, followed by baking at 80° C. for 2 to 3 hours in an oven to fix DNA onto the membrane which is used for hybridization.

(3.3: Selection of a Probe)

A probe suitable for Southern hybridization may be easily selected by those skilled in the art. For example, a primer is produced based on a base sequence obtained by BLAST search, followed by PCR amplification. A resultant It is assumed that Tos17 is used as a probe to carry our Southern hybridization. Tos17 is a retrotransposon. If a portion of Tos17 which is generally conserved in retrotransposons is used as a probe, the probe hybridizes to retrotransposons other than Tos17, resulting in difficulty in identifying a band. In this regard, when a first half portion of Tos17 containing a gag region (XbaI-BamHi fragment) is used as a probe, a clear band specific to Tos17 is obtained. When Nipponbare genomic DNA is amplified using the following primers, a probe specific to Tos17 is obtained.

| Name of Primer | Base sequence | |
|---|---|---|
| PA0131 | TGAAGCATCGGTCTCAGCTA | (SEQ ID NO. 17) |
| PA0132 | GTAGGTTGGGAGGGTTGTGA | (SEQ ID NO. 18) |

(3.4.1.: Preparation of a Probe for Hybridization)

A probe for hybridization is prepared using $^{32}P$ or GeneImage (Amersham).

(3.4.2: Composition of Hybridization Solution and a Preparation Method Thereof)

(Composition)
0.5M Sodium phosphate, pH 7.2
7% SDS
1 mM EDTA-2Na
200 µg/ml denatured calf thymus DNA (Production Method)
1. A bin of calf thymus DNA (SIGMA D-1501, 1 g) is weighted. Assuming that the weight is 1.1 g, DNA is placed in a flask containing 110 ml of TE10-1, followed by autoclaving. After the DNA is dissolved, sonication is performed at the maximum power for about one minute to obtain short fragments of the DNA. This solution is preserved at −20° C. as 10 mg/ml stock solution.

2. About 600 ml of MilliQ water is placed in a 600 ml beaker. 78 g of NaH$_2$PO$_4$.2H$_2$O (FW=156.01) is transferred to the beaker and is dissolved.

3. About 100 ml of MilliQ water is placed in another beaker. 25 g of sodium hydroxide is dissolved in the beaker.

4. The sodium hydroxide solution is added to the sodium phosphate solution to an extent that the pH of the sodium phosphate solution is 7.

5. 70 g of SDS is added to the sodium phosphate solution in 2-3 divided amounts, and is dissolved.

6. 372 mg of EDTA-2Na is weighed and is added to the sodium phosphate solution.

7. 20 ml of denatured calf thymus DNA is added.

8. The remaining sodium hydroxide solution is added to a volume of 1 l while adjusting to pH 7.2.

9. The solution is preserved at room temperature or at 42° C. in an incubator. No sterilization is required.

(3.4.3: Hybridization)

1. The DNA solution for a Tos17 probe is adjusted to 25 ng/µl to prepare a stock solution.

2. λ/HindIII solution is adjusted to 0.5 ng/µl to prepare a stock solution.

3. Megaprime DNA Labeling System, dCTP (Amersham, RPN1606) and α-$^{32}$P dCTP (Amersham, AA0005, 3000 Ci/mmol) are used for labeling.

Tos17 solution 1 to 2 µl
λ/HindIII solution 1 µl
Primer solution 5 µl
H$_2$O 28 µl 4. The above-described solutions are mixed together. The mixture is subjected to denaturation for 1 to 2 minutes in a boiling water bath. Thereafter, the tube is placed back on ice.

5. 10 µl of buffer solution for labeling and 1 µl of Klenow fragment solution are placed into a tube. α-$^{32}$P dCTP is added to the tube, followed by a labeling reaction at 37° C.

6. 20 to 30 ml of hybridization solution per membrane is placed in a polyseal bag, followed by prehybridization at 65° C. for one hour.

7. After the labeling reaction, unreacted labels are removed using MicroSpin S-200 HR Columns, pre-equilibrated in TE buffer (Amersham, 27-5120-01). (3000 rpm, 1 min)

8. The probe solution is subjected to thermal denaturation for one minute in a boiling water bath, and is added to hybridization solution. Hybridization solution exchange is not required.

9. Hybridization is carried out at 65° C. overnight.

10. The membrane is washed twice with 2×SSC at 55° C. for 30 minutes to 1 hour.

11. Finally, the membrane is rinsed with 2×SSC and is sandwiched with SARAN wrap.

12. Autoradiography is carried out at −80° C. for 1 to 2 days using an intensifying screen.

Example 4

Production of a DWF4 Gene Disruption Plant Using Homologous Recombination

A method of disrupting a plant gene using plant homologous recombination is well known as described in, for example, Rie Terada et al., Nature Biotechnology, Published on line; 9.

Example 5

Production of a Modified Plant by Overexpression of OsDWF4

Figure 10:
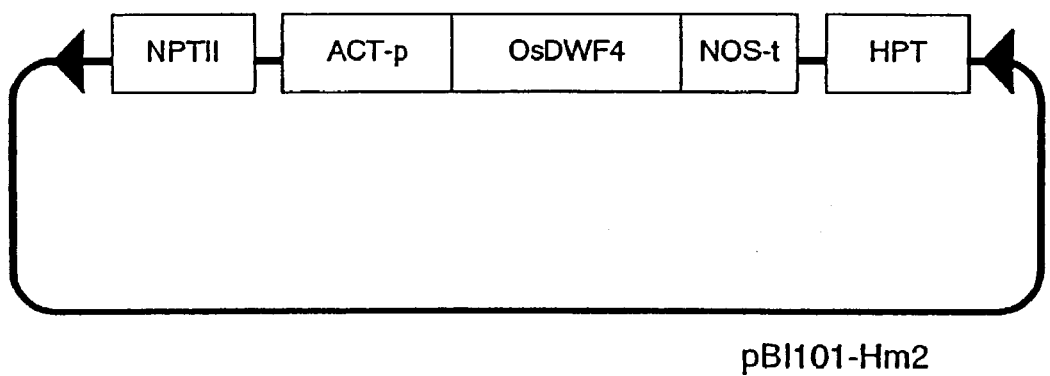
FIG. 10 shows the structure of an expression vector for overexpressing OsDWF4.

In order to increase the content of endogenous brassinosteroid, a vector which overexpresses OsDWF4 cDNA under control of a rice actin promoter (indicated by ACT-p in FIG. 10) was constructed. This vector contains a kanamycin and gentamicin resistance gene (indicated by NPTII), a terminator for nopaline synthase (indicated by NOS-t), and a hygromycin resistance gene (indicated by HPT). According to a method described in Tanaka et al. (supra), this expression vector was used to transform rice (Nipponbare) and investigate a character of the modified plant.

Among 36 lines obtained, 14 lines showed an increased number of grains per spike as compared to wild type (non-transformant) Nipponbare (Table 1).

TABLE 1

Morphology of transformed rice with overexpression of OsDWF4

|  | Spike length (mm) | 1st internode length (mm) | 2nd internode length (mm) | 3rd internode length (mm) | 4th internode length (mm) | 5th internode length (mm) | Full length (mm) | Number of grains per spike |
|---|---|---|---|---|---|---|---|---|
| T. 1 | 149 | 176 | 113 | 63 | 55 | 17 | 573 | 15 |
| T. 2 | 166 | 343 | 110 | 66 | 19 |  | 704 | 41 |
| T. 3 | 157 | 212 | 104 | 68 | 37 |  | 578 | 29 |
| T. 4 | 118 | 173 | 81 | 64 | 34 |  | 470 | 30 |
| T. 6 | 143 | 203 | 126 | 69 | 60 | 8 | 609 | 14 |
| T. 7 | 151 | 310 | 153 | 80 | 56 | 6 | 756 | 39 |
| T. 8 | 148 | 256 | 123 | 77 | 60 |  | 664 | 37 |
| T. 9 | 159 | 280 | 149 | 70 | 59 |  | 717 | 41 |
| T. 10 | 154 | 231 | 127 | 86 | 53 | 10 | 641 | 38 |
| T. 11 | 137 | 168 | 112 | 80 | 55 |  | 552 | 12 |
| T. 12 | 158 | 256 | 128 | 68 | 29 |  | 639 | 29 |
| T. 13 | 174 | 305 | 143 | 78 | 58 |  | 758 | 49 |
| T. 14 | 144 | 167 | 92 | 62 | 58 |  | 523 | 40 |
| T. 15 | 154 | 215 | 127 | 72 | 58 |  | 626 | 44 |
| T. 16 | 157 | 301 | 139 | 67 | 72 | 19 | 755 | 31 |
| T. 17 | 142 | 190 | 136 | 92 | 78 | 59 | 697 | 12 |
| T. 18 | 150 | 256 | 143 | 92 | 55 | 40 | 736 | 22 |
| T. 19 | 146 | 150 | 111 | 67 | 57 | 22 | 553 | 10 |
| T. 20 | 163 | 282 | 151 | 85 | 55 |  | 736 | 26 |

TABLE 1-continued

Morphology of transformed rice with overexpression of OsDWF4

| | Spike length (mm) | 1st internode length (mm) | 2nd internode length (mm) | 3rd internode length (mm) | 4th internode length (mm) | 5th internode length (mm) | Full length (mm) | Number of grains per spike |
|---|---|---|---|---|---|---|---|---|
| T. 21 | 151 | 202 | 130 | 62 | 48 | | 593 | 14 |
| T. 22 | 163 | 290 | 135 | 58 | 40 | | 686 | 38 |
| T. 23 | 165 | 338 | 132 | 62 | 11 | | 708 | 42 |
| T. 24 | 134 | 142 | 97 | 62 | 49 | 30 | 514 | 9 |
| T. 25 | 152 | 240 | 126 | 69 | 58 | 33 | 718 | 24 |
| T. 26 | 151 | 282 | 145 | 74 | 74 | 53 | 779 | 49 |
| T. 27 | 156 | 254 | 128 | 73 | 58 | | 669 | 44 |
| T. 28 | 190 | 350 | 157 | 58 | 33 | | 788 | 24 |
| T. 29 | 163 | 293 | 135 | 69 | 47 | | 707 | 15 |
| T. 30 | 149 | 164 | 125 | 77 | 64 | 30 | 609 | 40 |
| T. 31 | 179 | 332 | 174 | 69 | 53 | 10 | 817 | 61 |
| T. 32 | 125 | 128 | 79 | 64 | 63 | | 459 | 19 |
| T. 33 | 169 | 319 | 136 | 84 | 57 | | 765 | 18 |
| T. 34 | 151 | 113 | 75 | 63 | 56 | | 458 | 3 |
| T. 35 | 188 | 322 | 141 | 68 | 47 | | 766 | 50 |
| T. 36 | 159 | 209 | 146 | 75 | 65 | 9 | 663 | 30 |
| T. 37 | 159 | 293 | 99 | 75 | 47 | | 673 | 16 |
| NT. 1 | 155 | 257 | 143 | 95 | 62 | | 712 | 36 |
| NT. 2 | 162 | 241 | 144 | 91 | 32 | | 670 | 30 |
| NT. 3 | 157 | 235 | 143 | 85 | 20 | | 640 | 37 |
| NT. 4 | 155 | 242 | 128 | 89 | 32 | | 646 | 35 |
| NT. 5 | 131 | 193 | 120 | 84 | 88 | | 616 | 27 |

T.: Transformant, NT.: Non-transformant

TABLE 2

Test of significance difference of grain weight of transformed rice with overexpression of OsDWF4

| | Weight of 10 grains (Number of replications) | Weight of 10 grains (average) | Weight of 10 grains (standard deviation) | Weight of 10 grains (standard error) | Total number of grains | Total weight of grains |
|---|---|---|---|---|---|---|
| wt-4 | 5 | 0.252 | 0.015 | 0.007 | 56 | 1.33 |
| 13 | 6 | 0.271 | 0.026 | 0.011 | 69 | 1.78 |
| 26 | 8 | 0.262 | 0.013 | 0.005 | 88 | 2.23 |
| 31 | 10 | 0.270 | 0.012 | 0.004 | 109 | 2.84 |
| 35 | 4 | 0.265 | 0.006 | 0.003 | 45 | 1.17 |

| Source | df | Sum of Squares | Mean Square | F-Value | P-Value |
|---|---|---|---|---|---|
| Line | 4 | .001 | 3.527E−4 | 1.450 | .244D |
| Residual | 28 | .007 | 2.433E−4 | | |

Dependent: Wt. per 10

Among the selected 14 lines, 3 lines which had a particularly large increase in the number of grains were further selected (13, 26, and 31). The grain weight of the 3 lines was compared with that of wild type (non-transformant) Nipponbare. No significant difference was found between each line ("Weight of 10 grains (average)" in Table 2). In contrast, the total number of grains in the modified plant was significantly increased as compared to that of the wild type (non-transformant) Nipponbare. Therefore, the total weight of grains was also increased ("Total number of grains" and "Total weight of grains" in Table 2).

According to this result, it was demonstrated that by overexpressing DWF4 (e.g., OsDWF4) in monocotyledonous plants, modified plants having an increased yield can be obtained, contrary to the prediction based on conventional findings of dicotyledonous plants (*Arabidopsis*).

Example 6

Measurement of Activity of an Isolated OsDWF4 Homolog or OsDWF4 Variant

Whether or not a protein encoded by an isolated OsDWF4 homolog or OsDWF4 variant has an activity of a wild type OsDWF4 protein can be determined as follows.

After an OsDWF4 homolog or OsDWF4 variant is isolated, this isolated gene is linked to a promoter for OsDWF4 such that it is placed under control of the promoter in accordance with the method described in Example 5, thereby constructing a vector for expressing the isolated gene.

This vector is introduced into plants having a mutation in OsDWF4 within the genome (plants having a mutant phenotype, such as dwarfism and/or erected leaf, including, for example, a rice Tos2091 mutant). When the gene introduction complements for a mutant phenotype, such as dwarfism and/or erected leaf, in the obtained transformant, it is meant that the isolated OsDWF4 homolog or OsDWF4 variant has an activity of OsDWF4.

Therefore, whether or not the isolated OsDWF4 homolog or OsDWF4 variant has an activity of OsDWF4 can be determined by a complementation test using plants having mutation in OsDWF4.

Example 7

Application of Brassinosteroid to OsDWF4 Mutant Plants

By applying brassinosteroid to NE7040 obtained in Example 1 or a modified plant produced in Example 4 as a host (e.g., by spraying or coating), a plant having a desired character, such as short culm and erected leaf can be produced without reducing a yield.

As a method of applying brassinosteroid, for example, 1 μM aqueous solution is sprayed throughout plants before and after the differentiation period of the primary panicle branch. The present invention is not so limited.

The timing, concentration, site, and method of applying brassinosteroid are well known to those skilled in the art and may be appropriately selected by those skilled in the art.

Example 8

Production of a Desired Character Plant by Overexpressing OsDWF4 in an OsDWF4 Mutant Plant By overexpressing OsDWF4 in NE7040 obtained in Example 1 or a modified plant produced in Example 4 as a host, a plant having a desired character, such as short culm and erected leaf can be produced without reducing a yield.

In this method, OsDWF4 is operatively linked to an inducible promoter, a tissue specific promoter and/or a developmental stage specific promoter or the like to construct an expression vector containing the OsDWF4 gene, and the vector is introduced into plants as hosts.

As a promoter used, a spike specific promoter is preferable. Specifically, an example of such a promoter is a promoter for the MADS box gene of rice. The present invention is not so limited.

Example 9

Isolation of Rice Brassinosteroid Synthesis System Genes other than OsDWF4

The following genes involved in the brassinosteroid synthesis system of *Arabidopsis* are known other than DWF4:

DIM (DIMINUTO/DWARF1): C-24 Reductase: Klahre, U. et al., (1998). The *Arabidopsis* DIMINUTO/DWARF1 gene encodes a protein involved in steroid synthesis. Plant Cell 10:1677-1690;

DET2 (DE-ETIOLATED2): C-5α Reductase: Fujioka, S. et al., (1997) The *Arabidopsis* de-etiolated2 mutant is blocked early in brassinosteroid biosynthesis. Plant Cell 9:1951-1962.

CPD (CONSTITUTIVE PHOTOMORPHOGENESIS AND DWARFISM1): C-23α Hydroxylase: Szekeres, M. et al., (1996). Brassinosteroids rescue the deficiency of CYP90, a cytochrome P450, controlling cell elongation and de-etiolation in *Arabidopsis*. Cell 85:171-182;

DWF (DWARF): C-6 oxidase: Shimada, Y. et al., (2001) Brassinosteroid-6-oxidases from *Arabidopsis* and tomato catalyze multiple C-6 oxidations in brassinosteroid biosynthesis. Plant Physiol. 126: 770-779;

DWF5 (DWARF5): δ7 Sterol C-7 reductase: Choe, S. et al., (2000). Lesions in the sterol delta reductase gene of *Arabidopsis* cause dwarfism due to a block in brassinosteroid biosynthesis. Plant J. 21:431-443;

DWF7 (DWARF7): δ7 Sterol C-5 reductase: Choe, S. et al., (1999). The *Arabidopsis* dwf7/ste1 mutant is defective in the delta7 sterol C-5 desaturation step leading to brassinosteroid biosynthesis. Plant Cell 11: 207-221;

ROT3 (ROTUNDIFOLIA3): Cytochrome P450: Kim, G. T et al., (1998). The ROTUNDIFOLIA3 gene of *Arabidopsis thaliana* encodes a new member of the cytochrome P-450 family that is required for the regulated polar elongation of leaf cells. Genes Dev. 12:2381-2391; and FACKEL: C-14 Sterol reductase: Jang, J. C. et al., (2000). A critical role of sterols in embryonic patterning and meristem programming revealed by the fackel mutants of *Arabidopsis thaliana*. Genes Dev. 14:1485-1497.

However, rice genes corresponding to these genes have not been substantially isolated. Therefore, such rice genes were isolated as follows.

Probes were prepared from genes which had already been isolated from *Arabidopsis*. Using these probes, screening was carried out by hybridization under stringent conditions. As a result, the following genes involved in the brassinosteroid synthesis system were isolated from a rice cDNA library:

OsDIM (DIMINUTO/DWARF1): C-24 Reductase, SEQ ID NOS. 19 and 20;

OsDET2 (DE-ETIOLATED2): C-5α Reductase, SEQ ID NOS. 21 and 22;

OsCPD1 (CONSTITUTIVE PHOTOMORPHOGENESIS AND DWARFISM1): C-23α Hydroxylase, SEQ ID NOS. 23 and 24;

OsCPD2 (CONSTITUTIVE PHOTOMORPHOGENESIS AND DWARFISM2): C-23α Hydroxylase, SEQ ID NOS. 25 and 26;

OsCPD3 (CONSTITUTIVE PHOTOMORPHOGENESIS AND DWARFISM3): C-23α Hydroxylase, SEQ ID NOS. 27 and 28;

OsDWF (DWARF): C-6 oxidase, SEQ ID NOS. 29 and 30;

OsDWF5 (DWARF5): δ7 Sterol C-7 reductase, SEQ ID NOS. 31 and 32;

OsDWF7 (DWARF7): δ7 Sterol C-5 reductase, SEQ ID NOS. 33 and 34;

OsROT3 (ROTUNDIFOLIA3): Cytochrome P450, SEQ ID NOS. 35 and 36; and

OsFACKEL: C-14 Sterol reductase, SEQ ID NOS. 37 and 38.

Example 10

Production of a Rice Plant Having a Disrupted Brassinosteroid Synthesis System Gene Other than OsDWF4

According to a method described in Example 3, a rice plant having a disrupted brassinosteroid synthesis system gene other than OsDWF4 is produced below.

A PCR primer is designed based on the sequence of a gene isolated in Example 9. This PCR primer is used to determine whether or not a retrotransposon is introduced into a gene of interest. Next, a plant in which the retrotransposon is inserted in the gene of interest is isolated to confirm a phenotype specific to mutation of the brassinosteroid synthesis system gene (e.g., dwarfism, erected leaf, and the like).

In order to confirm that this phenotype is a result of disruption of the gene of interest, a complementation test is carried out as follows.

The gene of interest is operatively linked to a corresponding native promoter to construct an expression vector for the gene of interest. This expression vector is transferred to a gene disruption plant. Whether or not a phenotype (particularly, a phenotype relating to a brassinosteroid synthesis system gene) of the resultant gene disruption plant is complemented for by the introduction of the expression vector is determined. When a mutant phenotype is complemented for, it is meant that the gene of interest is disrupted in the gene disruption plant.

Example 11

Measurement of Activity of an Isolated Homolog Gene or Variant Gene

For genes involved in a brassinosteroid synthesis system other than OsDWF4, whether or not a protein encoded by an isolated homolog gene or variant gene has an activity of a wild type rice protein can be determined as follows.

After isolation of a homolog gene or a variant gene, this isolated gene is linked to a native promoter such that it is placed under control of the promoter for the gene in accordance with a method described in Example 5, thereby constructing a vector for expressing the isolated gene.

This vector is introduced into a plant having a mutation in a gene of interest within the genome (a plant having a mutant phenotype, such as dwarfism and/or erected leaf; for example, a rice mutant). When the gene introduction complements for a mutant phenotype, such as dwarfism and/or erected leaf, in this obtained transformant, it is meant that the isolated homolog gene or variant gene has an activity of a wild type rice gene.

Therefore, by a complementation test using a plant having a mutation in a gene of interest, it is possible to determine whether or not this isolated homolog gene or variant gene has an activity.

Example 12

Production of a Modified Plant by Overexpression of a Brassinosteroid Synthesis System Gene Other than OsDWF4

In order to increase the content of endogenous brassinosteroid, a vector which overexpresses cDNA of a brassinosteroid synthesis system gene other than OsDWF4 under control of a rice actin promoter is constructed.

This vector may contain a kanamycin and gentamicin resistance gene (indicated by NPTII), a terminator for nopaline synthase (indicated by NOS-t), and a hygromycin resistance gene (indicated by HPT), for example. According to a method described in Tanaka et al. (supra), this expression vector is used to transform rice (Nipponbare) and investigate a character of the modified plant.

Lines which have an increase in the number of grains per spike are selected as compared to wild type (non-transformant) Nipponbare. The selected lines are compared with wild type (non-transformant) rice in terms of the total number of grains and the total weight of grains. As a result, by overexpressing a gene of interest, a modified plant having an increased yield can be obtained.

Example 13

Production of a Modified Plant by Overexpression of a Brassinostecoid Synthesis System Gene in a Plant Having Mutation in a Brassinosteroid Synthesis System Gene According to the above-described examples, it is possible for those skilled in the art to produce plants having a mutation in any brassinosteroid synthesis system gene. By crossbreeding such mutant plants, it is possible to easily produce a mutant plant which has homozygous or heterozygous mutation in at least any two brassinosteroid synthesis system genes.

Further, it is possible for those skilled in the art to construct an expression vector for all brassinosteroid synthesis system genes. This expression vector may undergo overexpression, time specific expression, tissue specific expression, constitutive expression, and expression responsive to a stimulus, such as hormone.

By combining the above-described mutant plants and expression vectors, plants having a desired character can be produced by those skilled in the art.

Accordingly, the present invention provides a method of producing a plant having a desired morphology (particularly, short culm (semidwarf), verticality leading to improved light interception, and/or an increase in yield) by controlling a character, such as a morphology, of the plant without an undesired character, such as superdwarfism. The present invention also provides plants produced by the method, seeds and progeny thereof, and plant cells and whole plants thereof.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method of producing a modified rice plant having a short culm, erected leaf, or both, comprising:

modifying a rice plant so as to inhibit expression of a gene consisting of the nucleic acid sequence of SEQ ID NO:1, wherein yield of said modified rice plant is not reduced as compared to a wild type plant, and wherein the expression inhibition is achieved by using an antisense nucleic acid or by homology dependent gene silencing.

2. A modified rice plant produced by the method according to claim 1.

3. A seed of the modified rice plant produced by the method according to claim 2, wherein expression of SEQ ID NO:1 is inhibited.

4. A plant cell isolated from the modified rice plant produced by the method according to claim 1.

5. A progeny of the modified rice plant produced according to claim 2, wherein expression of SEQ ID NO:1 is inhibited.

* * * * *